(12) United States Patent
Wang et al.

(10) Patent No.: US 7,902,361 B2
(45) Date of Patent: *Mar. 8, 2011

(54) PYRIMIDIN-4-YL-3, 4-THIONE COMPOUNDS AND THEIR USE IN THERAPY

(75) Inventors: Shudong Wang, Nottingham (GB); Gavin Wood, Fife (GB); Kenneth Duncan, Cambusbarron (GB); Christopher Meades, Dundee (GB); Darren Gibson, Dundee (GB); Janice McLachlan, Dundee (GB); Alex Perry, Dundee (GB); David Blake, Angus (GB); Daniella I. Zheleva, Fife (GB); Peter Martin Fischer, Nottingham (GB)

(73) Assignee: Cyclacel Limited, Dundee (GB)

( * ) Notice: Subject to any disclaimer, the term of this patent is extended or adjusted under 35 U.S.C. 154(b) by 1030 days.

This patent is subject to a terminal disclaimer.

(21) Appl. No.: 11/408,463

(22) Filed: Apr. 21, 2006

(65) Prior Publication Data
US 2007/0021452 A1 Jan. 25, 2007

Related U.S. Application Data

(63) Continuation of application No. PCT/GB2004/004465, filed on Oct. 21, 2004.

(30) Foreign Application Priority Data

Oct. 21, 2003 (GB) .................................. 0324599.0
Dec. 23, 2003 (GB) .................................. 0330013.4

(51) Int. Cl.
| | |
|---|---|
| C07D 403/04 | (2006.01) |
| C07D 403/14 | (2006.01) |
| C07D 417/04 | (2006.01) |
| C07D 417/14 | (2006.01) |
| A61K 31/506 | (2006.01) |
| A61P 3/10 | (2006.01) |
| A61P 19/02 | (2006.01) |
| A61P 35/02 | (2006.01) |

(52) U.S. Cl. ...................... 544/331; 514/275; 514/235.8; 514/252.14; 544/295; 544/122

(58) Field of Classification Search .................. 544/331; 514/275
See application file for complete search history.

(56) References Cited

U.S. PATENT DOCUMENTS

| | | | |
|---|---|---|---|
| 6,221,873 B1 | 4/2001 | Havlicek et al. | |
| 6,531,479 B2 | 3/2003 | Wang | |
| 6,569,833 B1 | 5/2003 | Fahraeus | |
| 6,699,854 B2 | 3/2004 | Wang | |
| 6,703,395 B2 | 3/2004 | Havlicek | |
| 6,962,792 B1 | 11/2005 | Ball | |
| 7,045,519 B2 | 5/2006 | Nuss et al. | |
| 7,427,627 B2 * | 9/2008 | Wang et al. .................. | 514/275 |
| 7,432,260 B2 * | 10/2008 | Wang et al. ................. | 514/235.8 |

FOREIGN PATENT DOCUMENTS

| | | | |
|---|---|---|---|
| WO | WO-97/19065 A1 | 5/1997 | |
| WO | WO-03/029248 A1 | 4/2003 | |
| WO | WO-2004/043467 A1 | 5/2004 | |
| WO | WO-2004/043953 A1 | 5/2004 | |

(Continued)

OTHER PUBLICATIONS

Cecil Textbook of Medicine, edited by Bennet, J.C., and Plum F., 20th edition, vol. 1, 1004-1010, 1996.*

(Continued)

*Primary Examiner* — Venkataraman Balasubramanian
(74) *Attorney, Agent, or Firm* — Nelson Mullins Riley & Scarborough LLP; Cynthia L. Kanik; Brian C. Trinque

(57) ABSTRACT

The present invention relates to compounds of formula I, or pharmaceutically acceptable salts thereof,

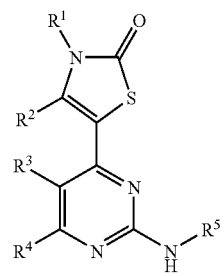

wherein $R^1$ and $R^5$ are each independently H, $C(OR^{j'})$ or a hydrocarbyl group optionally substituted by one or more $R^6$ groups;
$R^2$, $R^3$, and $R^4$ are each independently H, alkyl or alkenyl, each of which may be optionally substituted with one or more $R^7$ groups;
$R^6$ and $R^7$ are each independently halogen, $NO_2$, CN, $(CH_2)_mOR^a$, $O(CH_2)_nOR^b$, $(CH_2)_pNR^cR^d$, $CF_3$, $COOR^e$, $CONR^fR^g$, $COR^h$, $SO_3H$, $SO_2R^i$, $SO_2NR^jR^k$, $(CH_2)_q NR^{a'}COR^{g'}$, $R^{f'}$, $(CH_2)_rNR^{b'}SO_2R^{h'}$, $SO_2NR^{d'}R^{i'}$, $SO_2NR^{e'}(CH_2)_sOR^{c'}$, heterocycloalkyl or heteroaryl, wherein said heterocycloalkyl and heteroaryl may be optionally substituted by one or more substituents selected from aralkyl, sulfonyl, $R^m$ and $COR^n$;
$R^{g'}$, $R^{h'}$, $R^{i'}$ and $R^{j'}$ are each independently selected from alkyl, aryl, aralkyl and heteroaryl, each of which may be optionally substituted with one or more substituents selected from halogen, OH, $NO_2$, $NH_2$ $CF_3$ and COOH;
m, p, q and r are each independently 0, 1, 2 or 3;
n and s are each independently 1, 2, or 3; and
$R^{a-n}$ and $R^{a'-j'}$ are each independently H or alkyl.
Further aspects of the invention relate to pharmaceutical compositions comprising such compounds, and their use in the preparation of a medicament for treating one or more of the following: a proliferative disorder, a viral disorder, a CNS disorder, a stroke, alopecia and diabetes.

28 Claims, 2 Drawing Sheets

FOREIGN PATENT DOCUMENTS

WO WO-2004/056368 A1 7/2004

OTHER PUBLICATIONS

Malumbres et al., Trends in Biochemical Sciences, 30(11), 630-641, 2005.*
Lolli et al., Cell Cycle 4:4,572-577, 2005.*
Sherr et al., Genes & Development 18, 2699-2711,2004.*
Fischer Cell Cycle 3:6, 742-746, 2004.*
Blain et al., The Journal of Biological Chemistry, 272(41), 25863-25872, 1997.*
LuValle et al., Frontiers in Bioscience, 5, d493-503,2000.*
Patel et al. Biochem. Soc. Trans. 32(5), 803-808,2004.*
Jope et al., Trends in Biochemical Sciences 29(2), 95-102, 2004.*
Mass, R. D., Int. J. Radiation Oncology Bio. Phys.vol. 58(3): 932-940, 2004.*
Fabbro et al. Pharmacology & therapeutics 93, 79-98, 2002.*
U.S. Appl. No. 10/646,267, filed Aug. 22, 2003.
U.S. Appl. No. 10/153,441, filed May 21, 2002.
U.S. Appl. No. 10/671,747, filed Sep. 26, 2003.
U.S. Appl. No. 11/507,929, filed Aug. 21, 2006.
U.S. Appl. No. 10/671,747, filed Sep. 24, 2003.
U.S. Appl. No. 10/742,237, filed Dec. 18, 2003.
U.S. Appl. No. 10/810,767, filed Mar. 26, 2004.
U.S. Appl. No. 11/433,312, filed May 11, 2006.
U.S. Appl. No. 10/846,217, filed May 14, 2004.
U.S. Appl. No. 10/914,842, filed Aug. 10, 2004.
U.S. Appl. No. 10/991,942, filed Nov. 17, 2004.
U.S. Appl. No. 10/507,883, filed Sep. 15, 2004.
U.S. Appl. No. 10/952,575, filed Sep. 27, 2004.
U.S. Appl. No. 11/033,692, filed Jan. 11, 2005.
U.S. Appl. No. 11/238,533, filed Sep. 28, 2005.
U.S. Appl. No. 11/051,059, filed Feb. 4, 2005.
U.S. Appl. No. 11/124,636, filed May 5, 2005.
U.S. Appl. No. 11/122,331, filed May 3, 2005.
U.S. Appl. No. 11/121,753, filed May 3, 2005.
U.S. Appl. No. 11/124,622, filed May 5, 2005.
U.S. Appl. No. 11/140,136, filed May 26, 2005.
U.S. Appl. No. 11/129,198, filed May 13, 2005.
U.S. Appl. No. 11/192,893, filed Jul. 28, 2005.
U.S. Appl. No. 11/301,070, filed Dec. 9, 2005.
U.S. Appl. No. 11/326,805, filed Jan. 6, 2006.
U.S. Appl. No. 11/339,058, filed Jan. 25, 2006.
U.S. Appl. No. 11/339,059, filed Jan. 25, 2006.
U.S. Appl. No. 10/588,372, filed Aug. 3, 2006.
International Search Report for PCT/GB2004/004465, dated Apr. 24, 2006.

* cited by examiner

PYRIMIDIN-4-YL-3, 4-THIONE COMPOUNDS AND THEIR USE IN THERAPY

RELATED APPLICATIONS

This application is a continuation of PCT/GB2004/004465, filed on Oct. 21, 2004, which claims priority to GB 0324599.0, filed on Oct. 21, 2003 and GB 0330013.4, filed on Dec. 24, 2003. The entire contents of each of these applications are hereby incorporated herein by reference in their entirety.

BACKGROUND TO THE INVENTION

In eukaryotes, all biological functions, including DNA replication, cell cycle progression, energy metabolism, and cell growth and differentiation, are regulated through the reversible phosphorylation of proteins. The phosphorylation state of a protein determines not only its function, subcellular distribution, and stability, but also what other proteins or cellular components it associates with. The balance of specific phosphorylation in the proteome as a whole, as well as of individual members in a biochemical pathway, is thus used by organisms as a strategy to maintain homeostasis in response to an ever-changing environment. The enzymes that carry out these phosphorylation and dephosphorylation steps are protein kinases and phosphatases, respectively.

The eukaryotic protein kinase family is one of the largest in the human genome, comprising some 500 genes [1,2]. The majority of kinases contain a 250-300 amino acid residue catalytic domain with a conserved core structure. This domain comprises a binding pocket for ATP (less frequently GTP), whose terminal phosphate group the kinase transfers covalently to its macromolecular substrates. The phosphate donor is always bound as a complex with a divalent ion (usually $Mg^{2+}$ or $Mn^{2+}$). Another important function of the catalytic domain is the binding and orientation for phosphotransfer of the macromolecular substrate. The catalytic domains present in most kinases are more or less homologous.

A wide variety of molecules capable of inhibiting protein kinase function through antagonising ATP binding are known in the art [3-7]. By way of example, the applicant has previously disclosed 2-anilino-4-heteroaryl-pyrimidine compounds with kinase inhibitory properties, particularly against cyclin-dependent kinases (CDKs) [8-12]. CDKs are serine/threonine protein kinases that associate with various cyclin subunits. These complexes are important for the regulation of eukaryotic cell cycle progression, but also for the regulation of transcription [13, 14].

The present invention seeks to provide further 2-substituted-4-heteroaryl-pyrimidines. More specifically, the invention relates to compounds that have broad therapeutic applications in the treatment of a number of different diseases and/or that are capable of inhibiting one or more protein kinases.

STATEMENT OF INVENTION

A first aspect of the invention relates to a compound of formula I, or a pharmaceutically acceptable salt thereof,

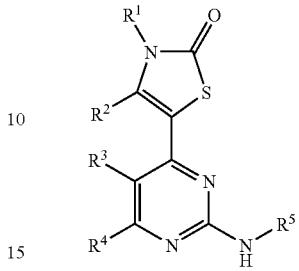

wherein
$R^1$ and $R^5$ are each independently H, $C(OR^j)$ or a hydrocarbyl group optionally substituted by one or more $R^6$ groups;
$R^2$, $R^3$, and $R^4$ are each independently H, alkyl or alkenyl, each of which may be optionally substituted with one or more $R^7$ groups;
$R^6$ and $R^7$ are each independently halogen, $NO_2$, CN, $(CH_2)_mOR^a$, $O(CH_2)_nOR^b$, $(CH_2)_pNR^cR^d$, $CF_3$, $COOR^e$, $CONR^fR^g$, $COR^h$, $SO_3H$, $SO_2R^i$, $SO_2NR^jR^k$, $(CH_2)_qNR^{a\prime}COR^{g\prime}$, $R^{f\prime}$, $(CH_2)_rNR^{b\prime}SO_2R^{h\prime}$, $SO_2NR^{d\prime}R^{i\prime}$, $SO_2NR^{e\prime}(CH_2)_sOR^{c\prime}$, heterocycloalkyl or heteroaryl, wherein said heterocycloalkyl and heteroaryl may be optionally substituted by one or more substituents selected from aralkyl, sulfonyl, $R^m$ and $COR^n$;
$R^{g\prime}$, $R^{h\prime}$, $R^{i\prime}$ and $R^{j\prime}$ are each independently selected from alkyl, aryl, aralkyl and heteroaryl, each of which may be optionally substituted with one or more substituents selected from halogen, OH, $NO_2$, $NH_2$ $CF_3$ and COOH;
m, p, q and r are each independently 0, 1, 2 or 3;
n and s are each independently 1, 2, or 3; and
$R^{a-n}$ and $R^{a\prime-f\prime}$ are each independently H or alkyl.

A second aspect of the invention relates to a pharmaceutical composition comprising a compound of formula I as defined above admixed with a suitable pharmaceutically acceptable carrier, excipient or diluent.

A third aspect of the invention relates to the use of a compound of formula I as defined above in the preparation of a medicament for treating one or more disorders selected from the following: a proliferative disorder, a viral disorder, a CNS disorder, a stroke, alopecia and diabetes.

A fourth aspect of the invention relates to the use of a compound of formula I as defined above in an assay for identifying further compounds capable of inhibiting one or more of a cyclin dependent kinase, GSK, aurora kinase and a PLK enzyme.

Previous studies by the applicant disclosed novel 2-anilino-4-(thiazol-5-yl)-pyrimidine compounds as ATP-competitive inhibitors of various protein kinases (S. Y. Wu et al., 2003, Structure, 11, 399; WO 2001072745, WO 2002079193, and WO 2003029248). Recent studies have now revealed that corresponding compounds containing a 3H-thiazol-2-one-5-yl group are also biologically active as kinase inhibitors.

BRIEF DESCRIPTION OF THE DRAWINGS

The present invention is further described by way of example, and with reference to the following figures, wherein.

DETAILED DESCRIPTION

Figure 1:
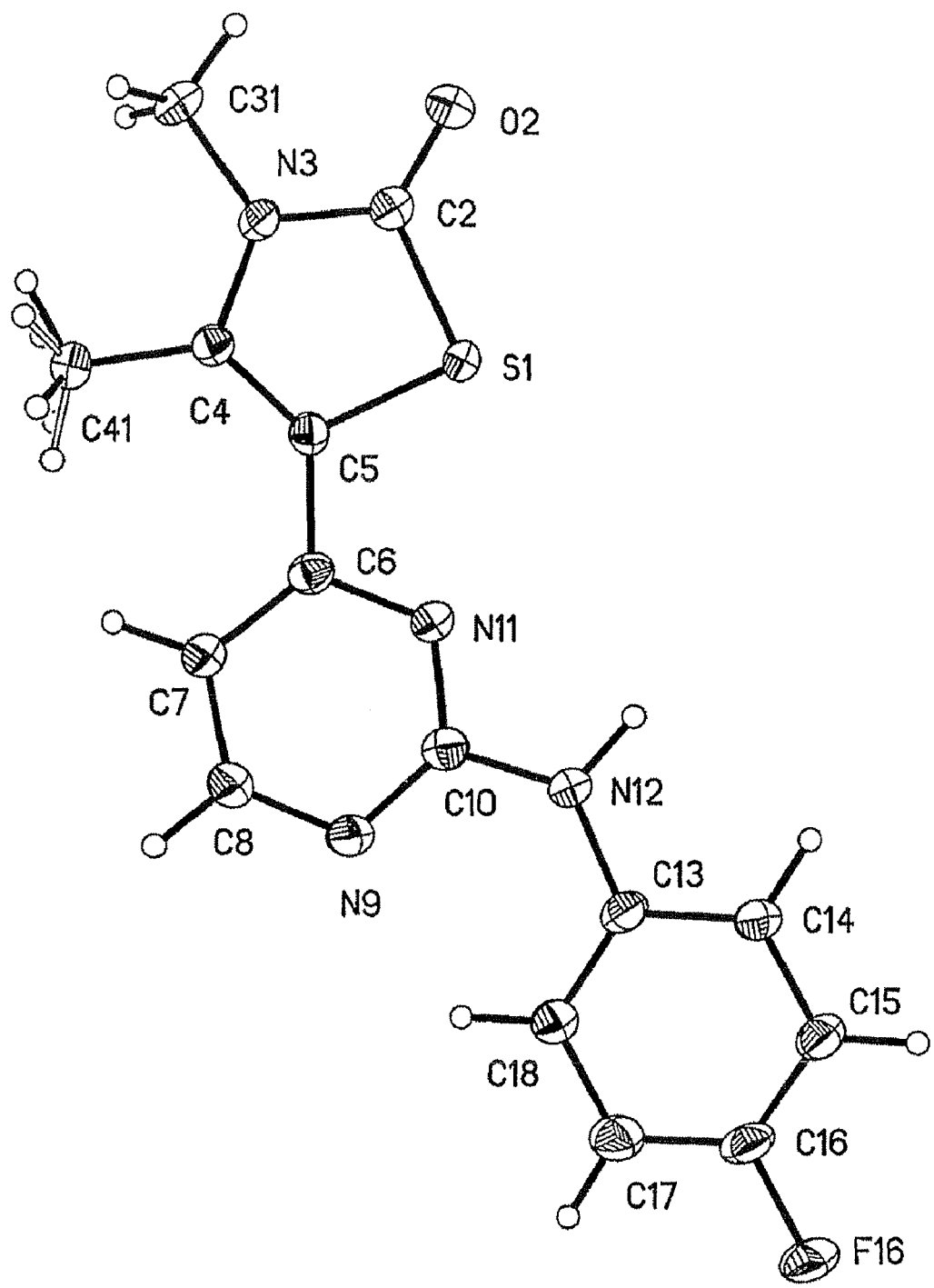
FIG. 1 shows the molecular structure of compound 2 in the crystal. Ellipsoids enclose 50% probability surfaces and H-atoms are drawn as circles of arbitrary radius. Figure produced with SHELXTL.
Figure 2:
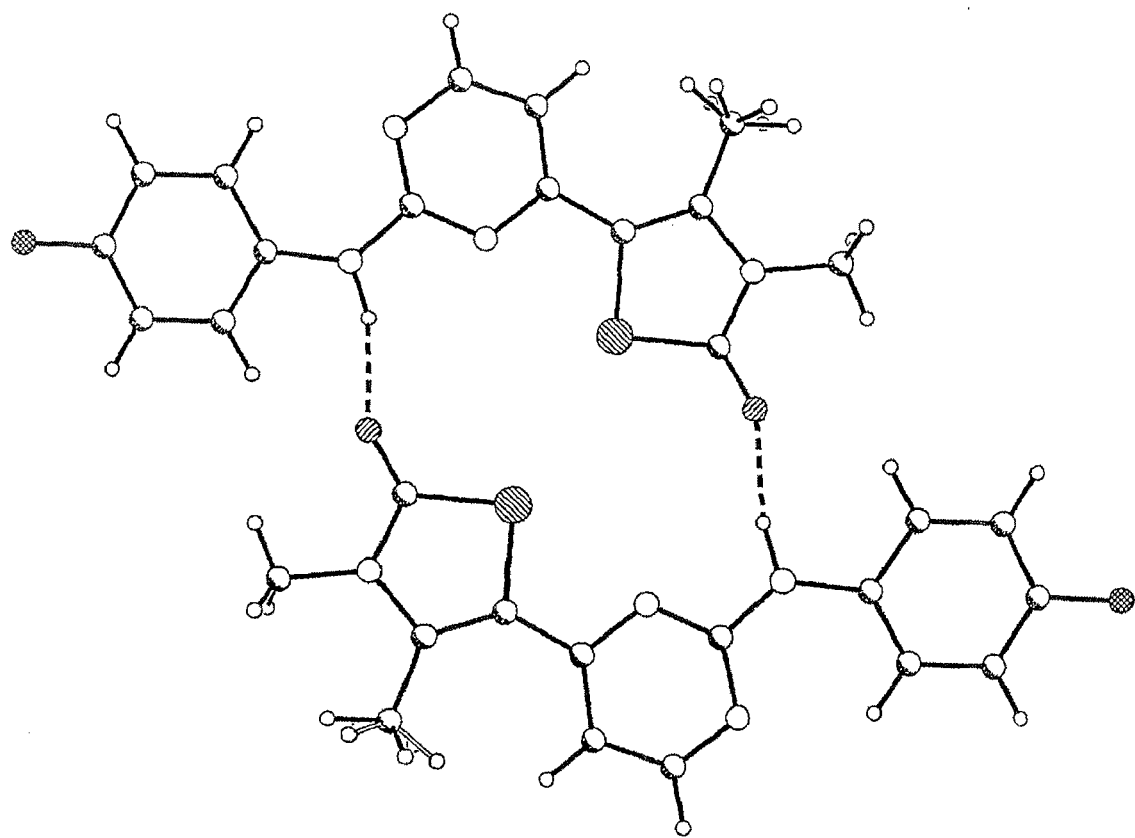
FIG. 2 shows H-bond formation in the crystal structure of compound 2.

One aspect of the invention relates to a compound of formula Ia, or a pharmaceutically acceptable salt thereof,

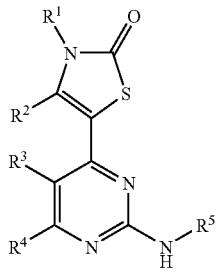

Ia wherein
$R^1$ and $R^5$ are each independently H or a hydrocarbyl group optionally substituted by one or more $R^6$ groups;
$R^2$, $R^3$, and $R^4$ are each independently H, alkyl or alkenyl, each of which may be optionally substituted with one or more $R^7$ groups;
$R^6$ and $R^7$ are each independently halogen, $NO_2$, CN, $(CH_2)_mOR^a$ where m is 0, 1, 2 or 3, $O(CH_2)_nOR^b$, where n is 1, 2, or 3, $NR^cR^d$, $CF_3$, $COOR^e$, $CONR^fR^g$, $COR^h$, $SO_3H$, $SO_2R^i$, $SO_2NR^jR^k$, heterocycloalkyl or heteroaryl, wherein said heterocycloalkyl and heteroaryl may be optionally substituted by one or more substituents selected from $R^m$ and $COR^n$; and
$R^{a-n}$ are each independently H or alkyl.

One aspect of the invention relates to a compound of formula I or Ia as defined above, or a pharmaceutically acceptable salt thereof, with the proviso that the compound is other than compounds I-XVII.

One aspect of the invention relates to a compound of formula I or Ia as defined above, or a pharmaceutically acceptable salt thereof, with the proviso that the compound is other than compounds I-XIII.

One aspect of the invention relates to a compound of formula I or Ia as defined above, or a pharmaceutically acceptable salt thereof, with the proviso that the compound is other than compounds XIV or XV.

One aspect of the invention relates to a compound of formula I or Ia as defined above, or a pharmaceutically acceptable salt thereof, with the proviso that the compound is other than compounds XVI or XVII.

As used herein, compound I is a compound prepared in accordance with Example 9 of WO 03/029248.

As used herein, compounds II-XIII are compounds prepared in accordance with Example 10 of WO 03/029248 (PCT/GB2002/004383).

As used herein, compounds XIV and XV are compounds prepared in accordance with the method set forth for the preparation of compounds 92 and 93 respectively of WO 2004/043953 (PCT/GB2003/004973).

As used herein, compounds XVI and XVII are compounds prepared in accordance with the method set forth for the preparation of compounds 4 and 11 respectively of PCT/GB2004/003282.

Another aspect of the invention relates to a compound of formula I or Ia as defined above, or a pharmaceutically acceptable salt thereof, with the proviso that the compound is other than:
3,4-Dimethyl-5-[2-(3-nitro-phenylamino)-pyrimidin-4-yl]-3H-thiazol-2-one;
5-[2-(4-Fluoro-phenylamino)-pyrimidin-4-yl]-3,4-dimethyl-3H-thiazol-2-one;
5-[2-(4-Hydroxy-phenylamino)-pyrimidin-4-yl]-3,4-dimethyl-3H-thiazol-2-one;
5-[2-(4-Chloro-phenylamino)-pyrimidin-4-yl]-3,4-dimethyl-3H-thiazol-2-one;
5-[2-(4-Methoxy-phenylamino)-pyrimidin-4-yl]-3,4-dimethyl-3H-thiazol-2-one;
5-[2-(3-Hydroxy-phenylamino)-pyrimidin-4-yl]-3,4-dimethyl-3H-thiazol-2-one;
5-[2-(4-Dimethylamino-phenylamino)-pyrimidin-4-yl]-3,4-dimethyl-3H-thiazol-2-one;
3,4-Dimethyl-5-[2-(4-morpholin-4-yl-phenylamino)-pyrimidin-4-yl]-3H-thiazol-2-one;
5-[2-(4-Fluoro-3-nitro-phenylamino)-pyrimidin-4-yl]-3,4-dimethyl-3H-thiazol-2-one
3,4-Dimethyl-5-[2-(4-methyl-3-nitro-phenylamino)-pyrimidin-4-yl]-3H-thiazol-2-one;
5-[2-(4-Fluoro-3-methyl-phenylamino)-pyrimidin-4-yl]-3,4-dimethyl-3H-thiazol-2-one;
3,4-Dimethyl-5-{2-[4-(4-methyl-piperazin-1-yl)-phenylamino]-pyrimidin-4-yl}-3H-thiazol-2-one;
5-[2-(3-Iodo-4-methyl-phenylamino)-pyrimidin-4-yl]-3,4-dimethyl-3H-thiazol-2-one;
5-[2-(4-Chloro-3-methyl-phenylamino)-pyrimidin-4-yl]-3,4-dimethyl-3H-thiazol-2-one;
5-[2-(6-Chloro-pyridin-3-ylamino)-pyrimidin-4-yl]-3,4-dimethyl-3H-thiazol-2-one;
3-Ethyl-5-[2-(6-methoxy-pyridin-3-ylamino)-pyrimidin-4-yl]-4-methyl-3H-thiazol-2-one;
5-[2-(4-Iodo-phenylamino)-pyrimidin-4-yl]-3,4-dimethyl-3H-thiazol-2-one.

As used herein, the term "hydrocarbyl" refers to a group comprising at least C and H. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, phosphorus and silicon. Preferably, the hydrocarbyl group is an aryl, heteroaryl, alkyl, cycloalkyl, aralkyl or alkenyl group.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Suitable substituents include, for example, one or more $R^6$ groups.

As used herein, the term "cycloalkyl" refers to a cyclic alkyl group which may be substituted (mono- or poly-) or unsubstituted. Preferably, the cycloalkyl group is a $C_{3-12}$ cycloalkyl group. Suitable substituents include, for example, one or more $R^6$ groups.

The term "heterocycloalkyl" refers to a cycloalkyl group containing one or more heteroatoms selected from O, N and S. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, pyrrolidinyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin- 2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, piperazinyl, chromanyl, etc. Additionally, for heterocycloalkyl, a heteroatom can occupy the position at which the heterocycle is attached to the remainder of the molecule. Thus, one of ordinary skill in the art will understand that the connection of said heterocycloalkyl rings is through a carbon or a sp$^3$ hybridized nitrogen heteroatom. Preferred heterocycloalkyl groups include piperazine, morpholine, piperidine and pyrrolidine.

As used herein, the term "alkenyl" refers to a group containing one or more carbon-carbon double bonds, which may be branched or unbranched, substituted (mono- or poly-) or unsubstituted. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, more preferably a $C_{2-3}$ alkenyl group. Suitable substituents include, for example, one or more $R^6$ groups as defined above.

As used herein, the term "aryl" refers to a $C_{6-12}$ aromatic group which may be substituted (mono- or poly-) or unsubstituted. Typical examples include phenyl and naphthyl etc. Suitable substituents include, for example, one or more $R^6$ groups.

As used herein, the term "heteroaryl" refers to a $C_{4-12}$ aromatic, substituted (mono- or poly-) or unsubstituted group, which comprises one or more heteroatoms. Preferred heteroaryl groups include pyrrole, pyrazole, pyrimidine, pyrazine, pyridine, quinoline, triazole, tetrazole, thiophene and furan. Again, suitable substituents include, for example, one or more $R^6$ groups.

Preferably, $R^{g'}$, $R^{h'}$, $R^{i'}$ and $R^{j'}$ are each independently selected from alkyl, phenyl, benzyl and pyridyl, each of which may be optionally substituted with one or more substituents selected from halogen, OH, $NO_2$, $NH_2$ $CF_3$ and COOH;

Preferably, $R^{a-n}$ and $R^{a'-f'}$ are each independently H, methyl, ethyl or isopropyl.

In one preferred embodiment of the invention, $R^1$ and $R^5$ are each independently H or a $C_{1-20}$ hydrocarbyl group optionally comprising up to six heteroatoms selected from from N, O, and S, and which is optionally substituted by one, two or three $R^6$ groups;

In another preferred embodiment, $R^5$ is aryl or heteroaryl, each of which may be optionally substituted by one or more $R^6$ groups.

In another preferred embodiment, $R^5$ is H, CO($R^{j'}$), aryl or heteroaryl, wherein said aryl or heteroaryl groups may be optionally substituted by one or more $R^6$ groups.

More preferably, $R^5$ is H, COMe, phenyl or pyridyl, wherein said phenyl or pyridyl groups may be optionally substituted by one or more $R^6$ groups.

More preferably still, $R^5$ is phenyl or pyridinyl, each of which may be optionally substituted by one or more $R^6$ groups.

In a preferred embodiment, $R^1$ is H or alkyl. More preferably, $R^1$ is H, methyl, ethyl or 3-methylbutyl.

Preferably, $R^2$, $R^3$, and $R^4$ are each independently H, $C_1$-$C_6$ alkyl or $C_2$-$C_6$ alkenyl, each of which may be optionally substituted with one, two or three $R^7$ groups.

More preferably, $R^2$ is $C_{1-6}$ alkyl. More preferably still, $R^2$ is methyl.

Preferably, $R^3$ and $R^4$ are both H.

Preferably, $R^6$ and $R^7$ are each independently F, Cl, Br, I, $NO_2$, CN, OH, OMe, OEt, $CH_2OH$, $O(CH_2)_2OMe$, $NH_2$, NHMe, $NMe_2$, $CF_3$, COOH, $CONH_2$, CONHMe, $CONMe_2$, COMe, $SO_3H$, $SO_2Me$, $SO_2NH_2$, $SO_2NHMe$, $SO_2NMe_2$, morpholine, piperidine, piperazine, N-acetylpiperazine, N-methylpiperazine, triazole, or tetrazole.

In one preferred embodiment, $R^3$ and $R^4$ are both H and $R^2$ is Me.

In one particularly preferred embodiment, the compound of the invention is of formula II, or a pharmaceutically acceptable salt thereof,

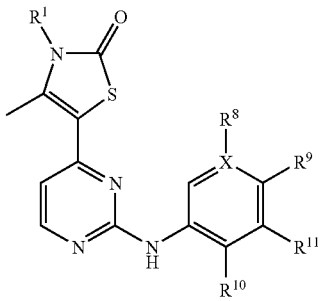

II wherein
$R^1$ is as defined above;
X is C; or X is N and $R^8$ is absent;
$R^8$, $R^9$, $R^{10}$ and $R^{11}$ are each independently H or as defined above for $R^6$ and $R^7$.

More preferably, for said compound of formula II,
$R^1$ is H or alkyl;
$R^8$ is H, $NO_2$, $OR^p$, halogen, $CF_3$, CN, $COR^q$, alkyl, $NR^rR^s$, $O(CH_2)_tOR^t$;
$R^9$ is H, $OR^u$, halogen, alkyl, $NR^vR^w$, or a heterocycloalkyl optionally substituted with one or more substituents selected from $R^m$ and $COR^n$;
t is 0, 1, 2 or 3;
$R^{10}$ is H, alkyl or $NR^xR^y$; and
$R^{p-y}$ are each independently H or alkyl.

In one particularly preferred, $R^1$ is H, Me, Et or 3-methylbutyl.

More preferably still, for said compound of formula II, $R^8$ is H, $NO_2$, OH, Me, I, $CF_3$, CN, $CH_2OH$, $CO_2H$, $CO_2Me$ or $NH_2$;
$R^9$ is H, F, OH, I, Cl, Br, OMe, $NMe_2$, morpholine, Me, N-methylpiperazine, N-acetylpiperazine or piperazine; and
$R^{10}$ is H, Me or $NMe_2$.

In one preferred embodiment, for said compound of formula II, $R^8$ is selected from H, $NO_2$, halogen, CN, $CF_3$, $SO_3H$, $(CH_2)_mOR^a$, $COOR^e$, $(CH_2)_pNR^cR^d$, $(CH_2)_rNR^{b'}SO_2R^h$, $(CH_2)_qNR^{a'}COR^{g'}$, $SO_2NR^jR^k$, $CONR^fR^g$, $SO_2NR^{e'}(CH_2)_sOR^{c'}$, $SO_2NR^{d'}R^{i'}$ and heterocycloalkyl optionally substituted by one or more $COR^n$ or sulfonyl groups.

More preferably, $R^8$ is selected from H, $NO_2$, OH, Me, I, CN, $CH_2OH$, $CF_3$, $CO_2H$, $CO_2Me$, $NH_2$, Cl, 4-acetylpiperazin-1-yl, OMe, $SO_3H$, $CH_2NHSO_2Me$, $CH_2NHCOPh$, $CH_2NHSO_2CF_3$, $SO_2NH_2$, $CONH^iPr$, $SO_2NHEt$, $SO_2NH(CH_2)_2OMe$, $SO_2NH^iPr$, $SO_2NH(CH_2)_2OH$, NHMe, $SO_2NH$-benzyl and morpholin-4-sulfonyl.

In one preferred embodiment, for said compound of formula II, $R^9$ is selected from H, $NO_2$, $SO_3H$, halogen, $(CH_2)_mOR^a$, $(CH_2)_pNR^cR^d$, $(CH_2)_qNR^{a'}COR^{g'}$, $SO_2NR^{e'}(CH_2)_sOR^{c'}$, $SO_2NR^{d'}R^{i'}$ and heterocycloalkyl optionally substituted by one or more $COR^n$, $R^m$ or aralkyl groups.

More preferably, $R^9$ is selected from H, F, OH, Cl, Br, OMe, $NMe_2$, morpholin-4-yl, 4-methylpiperazin-1-yl, Me, 4-acetyl-piperazin-1-yl, I, CH$_2$NHCOMe, NO$_2$, SO$_3$H, SO$_2$NH(CH$_2$)$_2$OMe, 4-benzylpiperazin-1-yl, SO$_2$NH (CH$_2$)$_2$OH, SO$_2$NH-benzyl, CH$_2$NH$_2$, CH$_2$NHCO-(pyrid-2-yl) and piperazin-1-yl.

In one preferred embodiment, for said compound of formula II, R$^{10}$ is selected from H, R$^{f'}$ and (CH$_2$)$_p$NR$^c$R$^d$.

More preferably, R$^{10}$ is selected from H, Me and NMe$_2$.

In one preferred embodiment, for said compound of formula II, R$^{11}$ is selected from H, R$^{f'}$, CF$_3$, halogen and (CH$_2$)$_q$NR$^{a'}$COR$^{g'}$.

More preferably, R$^{11}$ is selected from H, NHCOMe, CF$_3$, Br and Me.

In one preferred embodiment, X is N and R$^8$ is absent.

In another preferred embodiment, X is C.

In one preferred embodiment of the invention, the compound is selected from the following:

3,4-Dimethyl-5-[2-(3-nitro-phenylamino)-pyrimidin-4-yl]-3H-thiazol-2-one;
5-[2-(4-Fluoro-phenylamino)-pyrimidin-4-yl]-3,4-dimethyl-3H-thiazol-2-one;
5-[2-(4-Hydroxy-phenylamino)-pyrimidin-4-yl]-3,4-dimethyl-3H-thiazol-2-one;
5-[2-(4-Chloro-phenylamino)-pyrimidin-4-yl]-3,4-dimethyl-3H-thiazol-2-one;
5-[2-(4-Bromo-phenylamino)-pyrimidin-4-yl]-3,4-dimethyl-3H-thiazol-2-one;
5-[2-(4-Methoxy-phenylamino)-pyrimidin-4-yl]-3,4-dimethyl-3H-thiazol-2-one;
5-[2-(3-Hydroxy-phenylamino)-pyrimidin-4-yl]-3,4-dimethyl-3H-thiazol-2-one;
5-[2-(4-Dimethylamino-phenylamino)-pyrimidin-4-yl]-3,4-dimethyl-3H-thiazol-2-one;
3,4-Dimethyl-5-[2-(4-morpholin-4-yl-phenylamino)-pyrimidin-4-yl]-3H-thiazol-2-one;
5-[2-(4-Fluoro-3-nitro-phenylamino)-pyrimidin-4-yl]-3,4-dimethyl-3H-thiazol-2-one;
3,4-Dimethyl-5-[2-(4-methyl-3-nitro-phenylamino)-pyrimidin-4-yl]-3H-thiazol-2-one;
5-[2-(4-Fluoro-3-methyl-phenylamino)-pyrimidin-4-yl]-3,4-dimethyl-3H-thiazol-2-one;
3,4-Dimethyl-5-{2-[4-(4-methyl-piperazin-1-yl)-phenylamino]-pyrimidin-4-yl}-3H-thiazol-2-one;
5-[2-(3-Iodo-4-methyl-phenylamino)-pyrimidin-4-yl]-3,4-dimethyl-3H-thiazol-2-one;
5-[2-(4-Chloro-3-methyl-phenylamino)-pyrimidin-4-yl]-3,4-dimethyl-3H-thiazol-2-one;
3-[4-(3,4-Dimethyl-2-oxo-2,3-dihydro-thiazol-5-yl)-pyrimidin-2-ylamino]-benzonitrile;
5-{2-[4-(4-Acetyl-piperazin-1-yl)-phenylamino]-pyrimidin-4-yl}-3,4-dimethyl-3H-thiazol-2-one;
5-[2-(4-Chloro-3-hydroxymethyl-phenylamino)-pyrimidin-4-yl]-3,4-dimethyl-3H-thiazol-2-one;
3,4-Dimethyl-5-[2-(3-trifluoromethyl-phenylamino)-pyrimidin-4-yl]-3H-thiazol-2-one;
3,4-Dimethyl-5-[2-(2-methyl-5-nitro-phenylamino)-pyrimidin-4-yl]-3H-thiazol-2-one;
3,4-Dimethyl-5-[2-(4-methyl-3-trifluoromethyl-phenylamino)-pyrimidin-4-yl]-3H-thiazol-2-one;
5-[2-(4-Dimethylamino-3-nitro-phenylamino)-pyrimidin-4-yl]-3,4-dimethyl-3H-thiazol-2-one;
3-Ethyl-4-methyl-5-[2-(3-nitro-phenylamino)-pyrimidin-4-yl]-3H-thiazol-2-one;
2-Chloro-5-[4-(3-ethyl-4-methyl-2-oxo-2,3-dihydro-thiazol-5-yl)-pyrimidin-2-ylamino]-benzoic acid;
2-Chloro-5-[4-(3-ethyl-4-methyl-2-oxo-2,3-dihydro-thiazol-5-yl)-pyrimidin-2-ylamino]-benzoic acid methyl ester;
5-[2-(4-Dimethylamino-phenylamino)-pyrimidin-4-yl]-3-ethyl-4-methyl-3H-thiazol-2-one;
3-Ethyl-4-methyl-5-[2-(4-morpholin-4-yl-phenylamino)-pyrimidin-4-yl]-3H-thiazol-2-one;
3-Ethyl-4-methyl-5-[2-(4-methyl-3-nitro-phenylamino)-pyrimidin-4-yl]-3H-thiazol-2-one;
5-[2-(4-Dimethylamino-3-nitro-phenylamino)-pyrimidin-4-yl]-3-ethyl-4-methyl-3H-thiazol-2-one;
4-Methyl-3-(3-methyl-butyl)-5-[2-(3-nitro-phenylamino)-pyrimidin-4-yl]-3H-thiazol-2-one;
5-[2-(4-Chloro-phenylamino)-pyrimidin-4-yl]-4-methyl-3-(3-methyl-butyl)-3H-thiazol-2-one;
5-[2-(6-Chloro-pyridin-3-ylamino)-pyrimidin-4-yl]-3,4-dimethyl-3H-thiazol-2-one;
3-Ethyl-5-[2-(6-methoxy-pyridin-3-ylamino)-pyrimidin-4-yl]-4-methyl-3H-thiazol-2-one;
5-[2-(6-Chloro-pyridin-3-ylamino)-pyrimidin-4-yl]-4-methyl-3-(3-methyl-butyl)-3H-thiazol-2-one;
5-[2-(6-Methoxy-pyridin-3-ylamino)-pyrimidin-4-yl]-4-methyl-3-(3-methyl-butyl)-3H-thiazol-2-one;
5-[2-(4-Iodo-phenylamino)-pyrimidin-4-yl]-3,4-dimethyl-3H-thiazol-2-one;
5-[2-(2-Dimethylamino-5-nitro-phenylamino)-pyrimidin-4-yl]-3,4-dimethyl-3H-thiazol-2-one;
3,4-Dimethyl-5-[2-(4-piperazin-1-yl-phenylamino)-pyrimidin-4-yl]-3H-thiazol-2-one;
5-[2-(3-Amino-4-methyl-phenylamino)-pyrimidin-4-yl]-3,4-dimethyl-3H-thiazol-2-one;
4-Methyl-5-[2-(3-nitro-phenylamino)-pyrimidin-4-yl]-3H-thiazol-2-one;
4-Methyl-5-[2-(4-methyl-3-nitro-phenylamino)-pyrimidin-4-yl]-3H-thiazol-2-one;
N-{3-[4-(3,4-Dimethyl-2-oxo-2,3-dihydro-thiazol-5-yl)-pyrimidin-2-ylamino]-benzyl}-acetamide;
3-Ethyl-5-[2-(3-hydroxy-phenylamino)-pyrimidin-4-yl]-4-methyl-3H-thiazol-2-one;
5-[2-(3-Chloro-4-piperazin-1-yl-phenylamino)-pyrimidin-4-yl]-3,4-dimethyl-3H-thiazol-2-one;
3-Ethyl-5-[2-(4-fluoro-phenylamino)-pyrimidin-4-yl]-4-methyl-3H-thiazol-2-one;
5-[2-(4-Chloro-phenylamino)-pyrimidin-4-yl]-3-ethyl-4-methyl-3H-thiazol-2-one;
3-Ethyl-5-[2-(3-hydroxy-4-methyl-phenylamino)-pyrimidin-4-yl]-4-methyl-3H-thiazol-2-one;
5-[2-(4-Chloro-3-trifluoromethyl-phenylamino)-pyrimidin-4-yl]-3-ethyl-4-methyl-3H-thiazol-2-one;
5-{2-[3-(4-Acetyl-piperazin-1-yl)-phenylamino]-pyrimidin-4-yl}-3,4-dimethyl-3H-thiazol-2-one;
3-Ethyl-5-[2-(3-methoxy-phenylamino)-pyrimidin-4-yl]-4-methyl-3H-thiazol-2-one;
5-[2-(4-Chloro-3-methyl-phenylamino)-pyrimidin-4-yl]-3-ethyl-4-methyl-3H-thiazol-2-one;
3-Ethyl-4-methyl-5-[2-(4-nitro-phenylamino)-pyrimidin-4-yl]-3H-thiazol-2-one;
4-[4-(3-Ethyl-4-methyl-2-oxo-2,3-dihydro-thiazol-5-yl)-pyrimidin-2-ylamino]-benzenesulfonic acid;
3-[4-(3-Ethyl-4-methyl-2-oxo-2,3-dihydro-thiazol-5-yl)-pyrimidin-2-ylamino]-benzenesulfonic acid;
N-{3-[4-(3,4-Dimethyl-2-oxo-2,3-dihydro-thiazol-5-yl)-pyrimidin-2-ylamino]-benzyl}-methane-sulfonamide;
5-[2-(5-Methoxy-2-methyl-phenylamino)-pyrimidin-4-yl]-3,4-dimethyl-3H-thiazol-2-one
N-{3-[4-(3,4-Dimethyl-2-oxo-2,3-dihydro-thiazol-5-yl)-pyrimidin-2-ylamino]-benzyl}-benzamide;
N-{3-[4-(3,4-Dimethyl-2-oxo-2,3-dihydro-thiazol-5-yl)-pyrimidin-2-ylamino]-benzyl}-C,C,C-trifluoro-methane-sulfonamide;

N-{4-[4-(3,4-Dimethyl-2-oxo-2,3-dihydro-thiazol-5-yl)-pyrimidin-2-ylamino]-benzyl}-acetamide;
3-[4-(3,4-Dimethyl-2-oxo-2,3-dihydro-thiazol-5-yl)-pyrimidin-2-ylamino]-benzenesulfonamide;
3-[4-(3,4-Dimethyl-2-oxo-2,3-dihydro-thiazol-5-yl)-pyrimidin-2-ylamino]-N-isopropyl-4-methyl-benzamide;
3-[4-(3,4-Dimethyl-2-oxo-2,3-dihydro-thiazol-5-yl)-pyrimidin-2-ylamino]-N-ethyl-benzenesulfonamide;
5-[2-(5-Hydroxymethyl-2-methyl-phenylamino)-pyrimidin-4-yl]-3,4-dimethyl-3H-thiazol-2-one;
N-{3-[4-(3,4-Dimethyl-2-oxo-2,3-dihydro-thiazol-5-yl)-pyrimidin-2-ylamino]-5-trifluoromethyl-phenyl}-acetamide;
4-[4-(3,4-Dimethyl-2-oxo-2,3-dihydro-thiazol-5-yl)-pyrimidin-2-ylamino]-N-(2-methoxy-ethyl)-benzenesulfonamide;
5-[2-(4-Chloro-3-trifluoromethyl-phenylamino)-pyrimidin-4-yl]-3,4-dimethyl-3H-thiazol-2-one;
3-[4-(3,4-Dimethyl-2-oxo-2,3-dihydro-thiazol-5-yl)-pyrimidin-2-ylamino]-N-(2-methoxy-ethyl)-benzenesulfonamide;
5-[2-(3-Bromo-5-trifluoromethyl-phenylamino)-pyrimidin-4-yl]-3,4-dimethyl-3H-thiazol-2-one;
5-{2-[4-(4-Benzyl-piperazin-1-yl)-phenylamino]-pyrimidin-4-yl}-3,4-dimethyl-3H-thiazol-2-one;
4-[4-(3,4-Dimethyl-2-oxo-2,3-dihydro-thiazol-5-yl)-pyrimidin-2-ylamino]-2-trifluoromethyl-benzonitrile;
5-[2-(3-Amino-5-trifluoromethyl-phenylamino)-pyrimidin-4-yl]-3,4-dimethyl-3H-thiazol-2-one;
4-[4-(3,4-Dimethyl-2-oxo-2,3-dihydro-thiazol-5-yl)-pyrimidin-2-ylamino]-N-(2-hydroxy-ethyl)-benzenesulfonamide;
N-Benzyl-4-[4-(3,4-dimethyl-2-oxo-2,3-dihydro-thiazol-5-yl)-pyrimidin-2-ylamino]-benzenesulfonamide;
3-[4-(3,4-Dimethyl-2-oxo-2,3-dihydro-thiazol-5-yl)-pyrimidin-2-ylamino]-N-isopropyl-benzenesulfonamide;
3-[4-(3,4-Dimethyl-2-oxo-2,3-dihydro-thiazol-5-yl)-pyrimidin-2-ylamino]-N-(2-hydroxy-ethyl)-benzenesulfonamide;
3,4-Dimethyl-5-[2-(3-methylamino-5-trifluoromethyl-phenylamino)-pyrimidin-4-yl]-3H-thiazol-2-one;
N-Benzyl-3-[4-(3,4-dimethyl-2-oxo-2,3-dihydro-thiazol-5-yl)-pyrimidin-2-ylamino]-benzenesulfonamide;
3,4-Dimethyl-5-{2-[4-methyl-3-(morpholine-4-sulfonyl)-phenylamino]-pyrimidin-4-yl}-3H-thiazol-2-one;
3,4-Dimethyl-5-{2-[3-(morpholine-4-sulfonyl)-phenylamino]-pyrimidin-4-yl}-3H-thiazol-2-one;
5-[2-(4-Aminomethyl-phenylamino)-pyrimidin-4-yl]-3,4-dimethyl-3H-thiazol-2-one;
5-[2-(6-Chloro-5-methyl-pyridin-3-ylamino)-pyrimidin-4-yl]-3,4-dimethyl-3H-thiazol-2-one;
Pyridine-2-carboxylic acid 4-[4-(3,4-dimethyl-2-oxo-2,3-dihydro-thiazol-5-yl)-pyrimidin-2-ylamino]-benzylamide;
3,4-Dimethyl-5-{2-[(pyridin-3-ylmethyl)-amino]-pyrimidin-4-yl}-3H-thiazol-2-one;
5-(2-Amino-pyrimidin-4-yl)-3,4-dimethyl-3H-thiazol-2-one;
N-[4-(3,4-Dimethyl-2-oxo-2,3-dihydro-thiazol-5-yl)-pyrimidin-2-yl]-acetamide;

In one especially preferred embodiment, the compound of the invention is selected from the following:
3,4-Dimethyl-5-[2-(3-nitro-phenylamino)-pyrimidin-4-yl]-3H-thiazol-2-one [1];
5-[2-(4-Fluoro-phenylamino)-pyrimidin-4-yl]-3,4-dimethyl-3H-thiazol-2-one [2];
5-[2-(4-Hydroxy-phenylamino)-pyrimidin-4-yl]-3,4-dimethyl-3H-thiazol-2-one [3];
5-[2-(4-Chloro-phenylamino)-pyrimidin-4-yl]-3,4-dimethyl-3H-thiazol-2-one [4];
5-[2-(4-Bromo-phenylamino)-pyrimidin-4-yl]-3,4-dimethyl-3H-thiazol-2-one [5];
5-[2-(4-Methoxy-phenylamino)-pyrimidin-4-yl]-3,4-dimethyl-3H-thiazol-2-one [6];
5-[2-(3-Hydroxy-phenylamino)-pyrimidin-4-yl]-3,4-dimethyl-3H-thiazol-2-one [7];
5-[2-(4-Dimethylamino-phenylamino)-pyrimidin-4-yl]-3,4-dimethyl-3H-thiazol-2-one [8];
3,4-Dimethyl-5-[2-(4-morpholin-4-yl-phenylamino)-pyrimidin-4-yl]-3H-thiazol-2-one [9];
5-[2-(4-Fluoro-3-nitro-phenylamino)-pyrimidin-4-yl]-3,4-dimethyl-3H-thiazol-2-one [10];
3,4-Dimethyl-5-[2-(4-methyl-3-nitro-phenylamino)-pyrimidin-4-yl]-3H-thiazol-2-one [11];
5-[2-(4-Fluoro-3-methyl-phenylamino)-pyrimidin-4-yl]-3,4-dimethyl-3H-thiazol-2-one [12];
3,4-Dimethyl-5-{2-[4-(4-methyl-piperazin-1-yl)-phenylamino]-pyrimidin-4-yl}-3H-thiazol-2-one [13];
5-[2-(3-Iodo-4-methyl-phenylamino)-pyrimidin-4-yl]-3,4-dimethyl-3H-thiazol-2-one [14];
5-[2-(4-Chloro-3-methyl-phenylamino)-pyrimidin-4-yl]-3,4-dimethyl-3H-thiazol-2-one [15];
3-[4-(3,4-Dimethyl-2-oxo-2,3-dihydro-thiazol-5-yl)-pyrimidin-2-ylamino]-benzonitrile [16];
5-{2-[4-(4-Acetyl-piperazin-1-yl)-phenylamino]-pyrimidin-4-yl}-3,4-dimethyl-3H-thiazol-2-one [17];
5-[2-(4-Chloro-3-hydroxymethyl-phenylamino)-pyrimidin-4-yl]-3,4-dimethyl-3H-thiazol-2-one [18];
3,4-Dimethyl-5-[2-(3-trifluoromethyl-phenylamino)-pyrimidin-4-yl]-3H-thiazol-2-one [19];
3,4-Dimethyl-5-[2-(2-methyl-5-nitro-phenylamino)-pyrimidin-4-yl]-3H-thiazol-2-one [20];
3,4-Dimethyl-5-[2-(4-methyl-3-trifluoromethyl-phenylamino)-pyrimidin-4-yl]-3H-thiazol-2-one [21];
5-[2-(4-Dimethylamino-3-nitro-phenylamino)-pyrimidin-4-yl]-3,4-dimethyl-3H-thiazol-2-one [22];
3-Ethyl-4-methyl-5-[2-(3-nitro-phenylamino)-pyrimidin-4-yl]-3H-thiazol-2-one [23];
2-Chloro-5-[4-(3-ethyl-4-methyl-2-oxo-2,3-dihydro-thiazol-5-yl)-pyrimidin-2-ylamino]-benzoic acid [24];
2-Chloro-5-[4-(3-ethyl-4-methyl-2-oxo-2,3-dihydro-thiazol-5-yl)-pyrimidin-2-ylamino]-benzoic acid methyl ester [25];
5-[2-(4-Dimethylamino-phenylamino)-pyrimidin-4-yl]-3-ethyl-4-methyl-3H-thiazol-2-one [26];
3-Ethyl-4-methyl-5-[2-(4-morpholin-4-yl-phenylamino)-pyrimidin-4-yl]-3H-thiazol-2-one [27];
3-Ethyl-4-methyl-5-[2-(4-methyl-3-nitro-phenylamino)-pyrimidin-4-yl]-3H-thiazol-2-one [28];
5-[2-(4-Dimethylamino-3-nitro-phenylamino)-pyrimidin-4-yl]-3-ethyl-4-methyl-3H-thiazol-2-one [29];
4-Methyl-3-(3-methyl-butyl)-5-[2-(3-nitro-phenylamino)-pyrimidin-4-yl]-3H-thiazol-2-one [30];
5-[2-(4-Chloro-phenylamino)-pyrimidin-4-yl]-4-methyl-3-(3-methyl-butyl)-3H-thiazol-2-one [31];
5-[2-(6-Chloro-pyridin-3-ylamino)-pyrimidin-4-yl]-3,4-dimethyl-3H-thiazol-2-one [32];
3-Ethyl-5-[2-(6-methoxy-pyridin-3-ylamino)-pyrimidin-4-yl]-4-methyl-3H-thiazol-2-one [33];
5-[2-(6-Chloro-pyridin-3-ylamino)-pyrimidin-4-yl]-4-methyl-3-(3-methyl-butyl)-3H-thiazol-2-one [34];
5-[2-(6-Methoxy-pyridin-3-ylamino)-pyrimidin-4-yl]-4-methyl-3-(3-methyl-butyl)-3H-thiazol-2-one [35];
5-[2-(4-Iodo-phenylamino)-pyrimidin-4-yl]-3,4-dimethyl-3H-thiazol-2-one [36];

5-[2-(2-Dimethylamino-5-nitro-phenylamino)-pyrimidin-4-yl]-3,4-dimethyl-3H-thiazol-2-one [37];

3,4-Dimethyl-5-[2-(4-piperazin-1-yl-phenylamino)-pyrimidin-4-yl]-3H-thiazol-2-one [38];

5-[2-(3-Amino-4-methyl-phenylamino)-pyrimidin-4-yl]-3,4-dimethyl-3H-thiazol-2-one [39];

4-Methyl-5-[2-(3-nitro-phenylamino)-pyrimidin-4-yl]-3H-thiazol-2-one [40]; and

4-Methyl-5-[2-(4-methyl-3-nitro-phenylamino)-pyrimidin-4-yl]-3H-thiazol-2-one [41].

In one particularly preferred embodiment, the compound of the invention is capable of inhibiting one or more protein kinases, as measured by the appropriate assay. Preferably, the protein kinase is selected from CDK1/cyclin B, CDK2/cyclin E, CDK2/cyclin A, CDK4/cyclin D1, CDK7/cyclin H, CDK9/cyclin T1, GSK-3β, GSK-3α, DYRK1A and aurora kinase.

More preferably, the compound exhibits an $IC_{50}$ value (for kinase inhibition of one or more of the above-mentioned kinases) of less than 1 µM, preferably less than 0.1 µM, more preferably less than 0.01 µM, more preferably still, less than 0.002 µM, and even more preferably still, less than 0.001 µM.

Kinase activities (CDK1/cyclin B, CDK2/cyclin E, CDK2/cyclin A, CDK4/cyclin D1, CDK7/cyclin H, CDK9/cyclin T1 and aurora A) for selected compounds of the invention are shown in Table 8.

In vitro GSK3α, GSK3β and DYRK1A inhibitory activity of selected compounds of the invention are shown in Table 9. In the context of GSK3 and DYRK inhibitory activity, preferred compounds of the invention include those listed in Table 9.

Glycogen synthase activation in HEK293 cell mouse adipocytes and rat myotubes is shown in Table 10. Preferred compounds in this respect include compounds [62], [64], [67], [68], [75] and [76].

In one preferred embodiment, the compound is selected from the following: [1], [2], [3], [10], [11], [16], [18], [22], [23], [28], [38] and [41].

More preferably still, the compound is selected from the following: [11], [16], [23] and [28].

In another preferred embodiment, the compound of the invention is selected from [76], [64], [67], [62], [66], [68] and [75].

In another preferred embodiment, the compound of the invention is selected from [76], [64], [67], [62], [68] and [75].

In another preferred embodiment, the compound of the invention is selected from [64], [67], [68] and [75].

Therapeutic Use

The compounds of formula I have been found to possess anti-proliferative activity and are therefore believed to be of use in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29 or Saos-2 Using such assays it may be determined whether a compound is anti-proliferative in the context of the present invention.

On preferred embodiment of the present invention therefore relates to the use of one or more compounds of formula I in the preparation of a medicament for treating a proliferative disorder.

As used herein the phrase "preparation of a medicament" includes the use of a compound of formula Ia directly as the medicament in addition to its use in a screening programme for further therapeutic agents or in any stage of the manufacture of such a medicament.

Preferably, the proliferative disorder is a cancer or leukaemia. The term proliferative disorder is used herein in a broad sense to include any disorder that requires control of the cell cycle, for example cardiovascular disorders such as restenosis, cardiomyopathy and myocardial infarction, auto-immune disorders such as glomerulonephritis and rheumatoid arthritis, dermatological disorders such as psoriasis, anti-inflammatory, anti-fungal, antiparasitic disorders such as malaria, emphysema, alopecia, and chronic obstructive pulmonary disorder. In these disorders, the compounds of the present invention may induce apoptosis or maintain stasis within the desired cells as required.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

In one embodiment of the invention, the compound of formula I is administered in an amount sufficient to inhibit at least one CDK enzyme.

Preferably, the compound of formula I is administered in an amount sufficient to inhibit at least one of CDK2 and/or CDK4.

Another aspect of the invention relates to the use of a compound of formula I in the preparation of a medicament for treating a viral disorder, such as human cytomegalovirus (HCMV), herpes simplex virus type 1 (HSV-1), human immunodeficiency virus type 1 (HIV-1), and *varicella zoster* virus (VZV).

In a more preferred embodiment of the invention, the compound of formula I is administered in an amount sufficient to inhibit one or more of the host cell CDKs involved in viral replication, i.e. CDK2, CDK7, CDK8, and CDK9 [23].

As defined herein, an anti-viral effect within the scope of the present invention may be demonstrated by the ability to inhibit CDK2, CDK7, CDK8 or CDK9.

In a particularly preferred embodiment, the invention relates to the use of one or more compounds of formula Ia in the treatment of a viral disorder which is CDK dependent or sensitive. CDK dependent disorders are associated with an above normal level of activity of one or more CDK enzymes. Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

Selected compounds of the invention were found to possess anti-HIV activity as measured by the assays described in the accompanying examples.

In the context of anti-HIV activity, highly preferred compounds include the following:
5-[2-(3-Iodo-4-methyl-phenylamino)-pyrimidin-4-yl]-3,4-dimethyl-3H-thiazol-2-one (14),
3,4-Dimethyl-5-[2-(3-trifluoromethyl-phenylamino)-pyrimidin-4-yl]-3H-thiazol-2-one (19),
5-[2-(4-Dimethylamino-3-nitro-phenylamino)-pyrimidin-4-yl]-3,4-dimethyl-3H-thiazol-2-one (22),
5-[2-(4-Dimethylamino-3-nitro-phenylamino)-pyrimidin-4-yl]-3-ethyl-4-methyl-3H-thiazol-2-one (29),
5-[2-(6-Chloro-pyridin-3-ylamino)-pyrimidin-4-yl]-3,4-dimethyl-3H-thiazol-2-one (32),
N-{3-[4-(3,4-Dimethyl-2-oxo-2,3-dihydro-thiazol-5-yl)-pyrimidin-2-ylamino]-benzyl}-methane-sulfonamide (55),
N-{3-[4-(3,4-Dimethyl-2-oxo-2,3-dihydro-thiazol-5-yl)-pyrimidin-2-ylamino]-benzyl}-C,C,C-trifluoro-methane-sulfonamide (58),
5-[2-(4-Fluoro-phenylamino)-pyrimidin-4-yl]-3,4-dimethyl-3H-thiazol-2-one (2),
3,4-Dimethyl-5-[2-(4-methyl-3-nitro-phenylamino)-pyrimidin-4-yl]-3H-thiazol-2-one (11),
5-[2-(4-Chloro-3-methyl-phenylamino)-pyrimidin-4-yl]-3,4-dimethyl-3H-thiazol-2-one (15),
3-[4-(3,4-Dimethyl-2-oxo-2,3-dihydro-thiazol-5-yl)-pyrimidin-2-ylamino]-benzonitrile (16),
3,4-Dimethyl-5-[2-(4-methyl-3-trifluoromethyl-phenylamino)-pyrimidin-4-yl]-3H-thiazol-2-one (21),
3-Ethyl-4-methyl-5-[2-(3-nitro-phenylamino)-pyrimidin-4-yl]-3H-thiazol-2-one (23),
3-Ethyl-5-[2-(6-methoxy-pyridin-3-ylamino)-pyrimidin-4-yl]-4-methyl-3H-thiazol-2-one (33),
3,4-Dimethyl-5-[2-(4-piperazin-1-yl-phenylamino)-pyrimidin-4-yl]-3H-thiazol-2-one (38),
N-{4-[4-(3,4-Dimethyl-2-oxo-2,3-dihydro-thiazol-5-yl)-pyrimidin-2-ylamino]-benzyl}-acetamide (59),
3-[4-(3,4-Dimethyl-2-oxo-2,3-dihydro-thiazol-5-yl)-pyrimidin-2-ylamino]-benzenesulfonamide (60),
N-{3-[4-(3,4-Dimethyl-2-oxo-2,3-dihydro-thiazol-5-yl)-pyrimidin-2-ylamino]-5-trifluoromethyl-phenyl}-acetamide (64), and
4-[4-(3,4-Dimethyl-2-oxo-2,3-dihydro-thiazol-5-yl)-pyrimidin-2-ylamino]-N-(2-methoxy-ethyl)-benzenesulfonamide (65).

In the context of anti-HIV activity, highly preferred compounds include the following:
5-[2-(3-Iodo-4-methyl-phenylamino)-pyrimidin-4-yl]-3,4-dimethyl-3H-thiazol-2-one (14),
3,4-Dimethyl-5-[2-(3-trifluoromethyl-phenylamino)-pyrimidin-4-yl]-3H-thiazol-2-one (19),
5-[2-(4-Dimethylamino-3-nitro-phenylamino)-pyrimidin-4-yl]-3,4-dimethyl-3H-thiazol-2-one (22),
5-[2-(4-Dimethylamino-3-nitro-phenylamino)-pyrimidin-4-yl]-3-ethyl-4-methyl-3H-thiazol-2-one (29),
5-[2-(6-Chloro-pyridin-3-ylamino)-pyrimidin-4-yl]-3,4-dimethyl-3H-thiazol-2-one (32),
N-{3-[4-(3,4-Dimethyl-2-oxo-2,3-dihydro-thiazol-5-yl)-pyrimidin-2-ylamino]-benzyl}-methane-sulfonamide (55),
N-{3-[4-(3,4-Dimethyl-2-oxo-2,3-dihydro-thiazol-5-yl)-pyrimidin-2-ylamino]-benzyl}-C,C,C-trifluoro-methane-sulfonamide (58), and
N-{3-[4-(3,4-Dimethyl-2-oxo-2,3-dihydro-thiazol-5-yl)-pyrimidin-2-ylamino]-5-trifluoromethyl-phenyl}-acetamide (64).

Another aspect of the invention relates to the use of compounds of formula I, or pharmaceutically acceptable salts thereof, in the preparation of a medicament for treating diabetes.

In a particularly preferred embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in the latter's deactivation and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type-II diabetes [24]. Furthermore, it has been demonstrated that GSK3 is over-expressed in muscle cells of type II diabetics and that an inverse correlation exists between skeletal muscle GSK3 activity and insulin action [25].

GSK3 inhibition is therefore of therapeutic significance in the treatment of diabetes, particularly type II, and diabetic neuropathy.

It is notable that GSK3 is known to phosphorylate many substrates other than GS, and is thus involved in the regulation of multiple biochemical pathways. For example, GSK is highly expressed in the central and peripheral nervous systems.

Another aspect of the invention therefore relates to the use of compounds of formula I, or pharmaceutically acceptable salts thereof, in the preparation of a medicament for treating a CNS disorders, for example neurodegenerative disorders.

Preferably, the CNS disorder is Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages.

Without wishing to be bound by theory, it is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process [26].

Another aspect of the invention relates to the use of compounds of formula I, or pharmaceutically acceptable salts thereof, in the preparation of a medicament for treating bipolar disorder.

Yet another aspect of the invention relates to the use of compounds of formula I, or pharmaceutically acceptable salts thereof, in the preparation of a medicament for treating a stroke.

Reducing neuronal apoptosis is an important therapeutic goal in the context of head trauma, stroke, epilepsy, and motor neuron disease [27]. Therefore, GSK3 as a pro-apoptotic factor in neuronal cells makes this protein kinase an attractive therapeutic target for the design of inhibitory drugs to treat these diseases.

Yet another aspect of the invention relates to the use of compounds of formula Ia, or pharmaceutically acceptable salts thereof, in the preparation of a medicament for treating alopecia.

Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential [28]. This population of stem cells expresses a higher level of non-cadherin-associated β-catenin [29], which may contribute to their high proliferative potential. Moreover, transgenic mice overexpressing a truncated β-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia.

A further aspect of the invention relates to a method of treating a GSK3-dependent disorder, said method comprising administering to a subject in need thereof, a compound of formula Ia, or a pharmaceutically acceptable salt thereof, as defined above in an amount sufficient to inhibit GSK3.

Preferably, the compound of formula I, or pharmaceutically acceptable salt thereof, is administered in an amount sufficient to inhibit GSK3β.

In one embodiment of the invention, the compound of formula I is administered in an amount sufficient to inhibit at least one PLK enzyme.

The polo-like kinases (PLKs) constitute a family of serine/threonine protein kinases. Mitotic *Drosophila melanogaster* mutants at the polo locus display spindle abnormalities [30] and polo was found to encode a mitotic kinase [31]. In humans, there exist three closely related PLKs [32]. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments [33, 34], mediation of interactions with other proteins [35], or may constitute part of an autoregulatory domain [36]. Furthermore, the polo box-dependent PLK1 activity is required for proper metaphase/anaphase transition and cytokinesis [37, 38].

Studies have shown that human PLKs regulate some fundamental aspects of mitosis [39, 40]. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis [41].

In a more preferred embodiment of the invention, the compound of formula I is administered in an amount sufficient to inhibit PLK1.

Of the three human PLKs, PLK1 is the best characterized; it regulates a number of cell division cycle effects, including the onset of mitosis [42, 43], DNA-damage checkpoint activation [44, 45], regulation of the anaphase promoting complex [46-48], phosphorylation of the proteasome [49], and centrosome duplication and maturation [50].

Specifically, initiation of mitosis requires activation of M-phase promoting factor (MPF), the complex between the cyclin dependent kinase CDK1 and B-type cyclins [51]. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF [52]. In interphase, cyclin B localizes to the cytoplasm [53], it then becomes phosphorylated during prophase and this event causes nuclear translocation [54, 55]. The nuclear accumulation of active MPF during prophase is thought to be important for initiating M-phase events [56]. However, nuclear MPF is kept inactive by WEE1 unless counteracted by CDC25C. The phosphatase CDC25C itself, localized to the cytoplasm during interphase, accumulates in the nucleus in prophase [57-59]. The nuclear entry of both cyclin B [60] and CDC25 [61] are promoted through phosphorylation by PLK1 [43]. This kinase is an important regulator of M-phase initiation.

In one particularly preferred embodiment, the compounds of formula I are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of formula I is administered in an amount sufficient to inhibit PLK2 and/or PLK3.

Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis [62]. PLK2 is the least well understood homologue of the three PLKs. Both PLK2 and PLK3 may have additional important post-mitotic functions [35].

Pharmaceutical Compositions

Another aspect of the invention relates to a pharmaceutical composition comprising a compound of formula I as defined above admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of formula I can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of compounds of formula I. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes the use of solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of formula I wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient.

Combinations

In a particularly preferred embodiment, the one or more compounds of the invention are administered in combination with one or more other therapeutically active agents, for example, existing drugs available on the market. In such cases, the compounds of the invention may be administered consecutively, simultaneously or sequentially with the one or more other active agents.

By way of example, it is known that anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Assays

Another aspect of the invention relates to the use of a compound of the invention in an assay for identifying further candidate compounds capable of inhibiting one or more protein kinases.

Preferably, the assay is a competitive binding assay.

More preferably, the competitive binding assay comprises contacting a compound of the invention with a protein kinase and a candidate compound and detecting any change in the interaction between the compound of the invention and the protein kinase.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove. Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of proliferative disorders, viral disorders, a CNS disorder, stroke, alopecia and diabetes.

Preferably, said candidate compound is generated by conventional SAR modification of a compound of the invention.

As used herein, the term "conventional SAR modification" refers to standard methods known in the art for varying a given compound by way of chemical derivatisation.

The above methods may be used to screen for a ligand useful as an inhibitor of one or more protein kinases.

Synthesis

Thiazole amines, alcohols, and thiols (Scheme 1, IIa, X=NH, O, and S, respectively) can exist in different tautomeric forms (D. Kikelj et al., 2002, *Science of Synthesis*, 11, 630). In all three cases the mesoionic form IIc is generally unimportant. Thiazole-2-amines (X=NH) in solution exist exclusively in the amino form Ia rather than the imino form IIb. Thiazole-2-ols (X=O) (S. P. Cornwell et al., 1981, *J. Chem. Soc. Perkin Trans.* 1, 2340) and thiazole-2-thiols (X=S), on the other hand, favour the 2-oxo and 2-thione forms IIb.

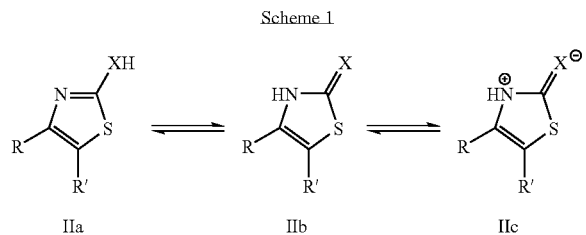

Scheme 1

5-(2-Amino-pyrimidin-4-yl)-3H-thiazol-2-ones I of the present invention can be prepared by any method known in the art. Some suitable methods are shown in Scheme 2.

*Heterocycl. Chem.* 23, 641). Alkylation of 3H-thiazol-2-ones VI can give rise to either the N-alkylated product VIII or the O-alkylated thiazole IX, depending on reaction conditions. Thus methylation of e.g. 3H-thiazol-2-one with diazomethane affords a mixture of N-methylated (i.e. 3-methyl-3H-thiazol-2-one) and O-methylated (i.e. 2-methoxy-thiazole) products (G. Klein et al., 1954, *Helv. Chim. Acta*, 37, 2057). On the other hand, methylation of 3H-thiazol-2-ones with trimethyloxonium tetrafluoroborate furnishes the O-methylated thiazole products exclusively (E. F. Atkins et al., 1994, *Tetrahedron*, 50, 7253). O-Alkylation of N-unsubstituted 3H-thiazol-2-ones is the exception rather than rule (T. Nishiwaki et al., 1981, *Heterocycles*, 16, 595), however, and treatment of 3H-thiazol-2-ones with alkyl halides under basic conditions usually affords the N-alkylated products only (R. Dahlbom, 1960, *Acta Chem. Scand.*, 14, 211). N-Alkylated product VIII can also be prepared unambiguously and directly from halo-diketone III by reaction with N-substituted-thiocarbamates VII (S. P. Cornwell et al., 1981, *J.*

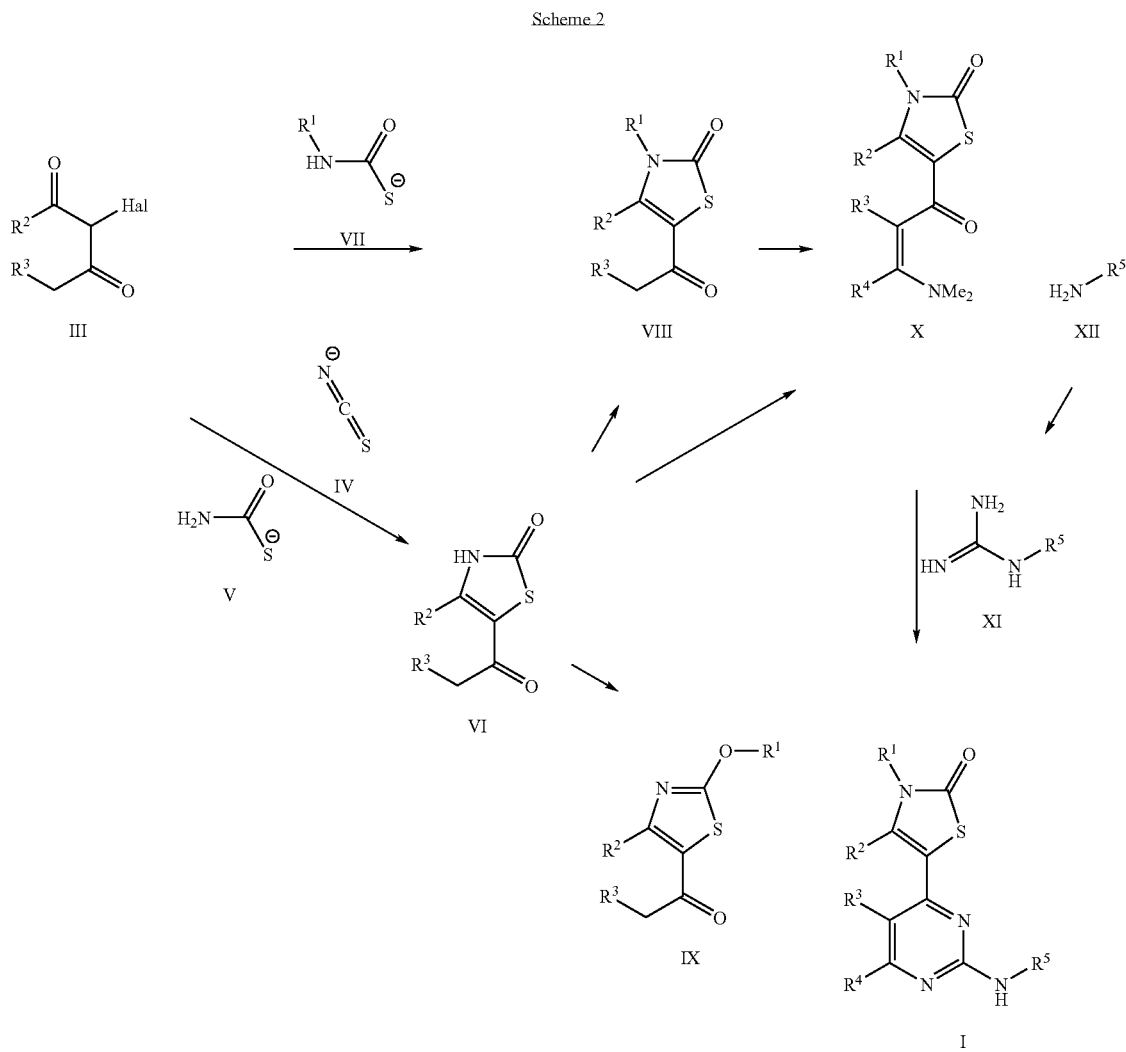

Scheme 2

Halo-diketones III can be converted to N-unsubstituted 5-acyl-thiazolones VI, either indirectly with thiocyanate IV (R. G. Guy, 1977, In *Chem. Cyanates Their Thio Deriv.*, Vol. 2, S. Patai, ed., pp. 819-886, Wiley, Chichester, Engl.) or directly with thiocarbamate V (J. J. D'Amico et al., 1986, *J.*

*Chem. Soc. Perkin Trans.* 1, 2340). The latter can be prepared e.g. by thiocarbamoylation of amines with carbonyl sulfide (Y. Gelernt et al., 1974, *J. Chem. Soc. Perkin Trans.* 1, 2610).

Conversion of ketones VIII to enaminones, e.g. with N,N'-dimethylformamide dimethylacetal to X, affords intermediates that are suitable for the following pyrimidine ring condensation reaction with guanidines XI (J. Zimmermann et al., 1996, *Arch. Pharm. Pharm. Med. Chem.*, 329, 371). Enaminone X (R¹=Me) can also be obtained by direct treatment of VI with N,N'-dimethylformamide dimethylacetal, which reagent also effects N-methylation. Alternatively, N-unsubstituted enaminone X (R¹=H) is obtained when VI is treated with tert-butoxy-bis(dimethylamino)methane (H. Bredereck et al., 1964, *Chem. Ber.*, 97, 3397). Guanidines XI can be prepared by reaction of cyanamide or certain of its derivatives (A. R. Katritzky et al., 1995, *Synth. Commun.*, 25, 1173).

The compounds shown in Table I were prepared using the procedures described above and detailed in the accompanying examples.

A further aspect of the invention relates to a process for preparing a compound of formula I as defined in claim 1, said process comprising reacting a compound of formula X with a compound of formula XI to form a compound of formula I.

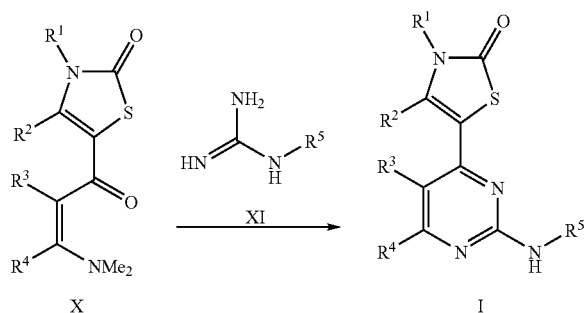

Preferably, said compound of formula X is prepared by the steps of:
(A) (i) reacting a compound of formula III with a compound of formula VII to form a compound of formula VIII;
  (ii) converting said compound of formula VIII to a compound of formula X;

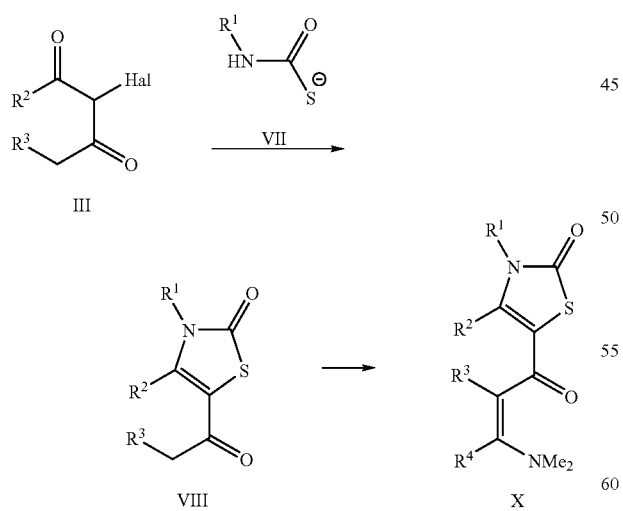

or
(B) (i) reacting a compound of formula III with a compound of formula IV to form a compound of formula VI;
  (ii) converting said compound of formula VI to a compound of formula VIII; and
  (iii) converting said compound of formula VIII into a compound of formula X;

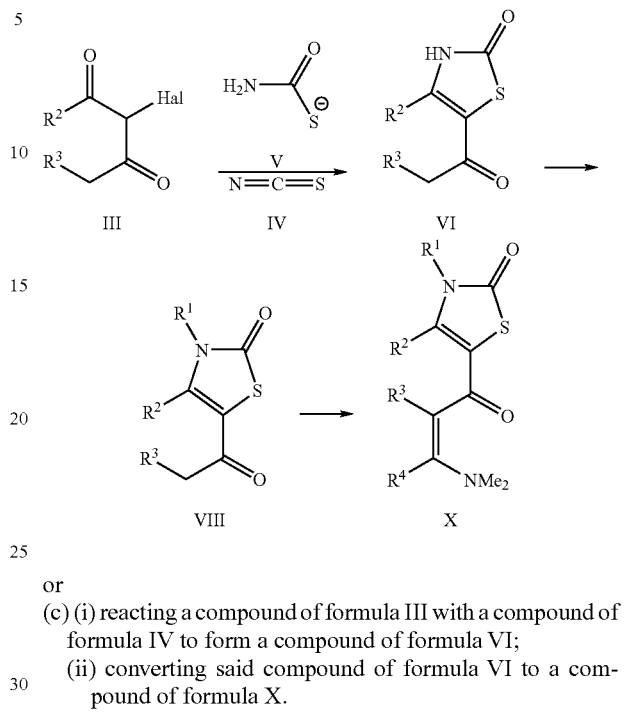

or
(c) (i) reacting a compound of formula III with a compound of formula IV to form a compound of formula VI;
  (ii) converting said compound of formula VI to a compound of formula X.

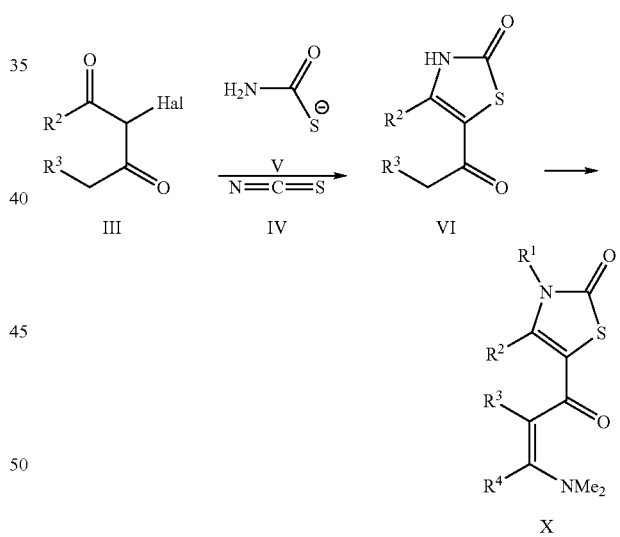

EXAMPLES

General

NMR spectra were obtained using a Varian INOVA-500 instrument. Chemical shifts are reported in parts per million relative to internal tetramethylsilane standard. Mass spectra were obtained using a Waters ZQ2000 single quadrupole mass spectrometer with electrospray ionization (ESI). Analytical and preparative RP-HPLC was performed using Vydac 218TP54 (250×4.6 mm) and 218TP1022 (250×22 mm) columns, respectively. Linear gradient elution using $H_2O$/MeCN

Example 1

5-Acetyl-3,4-dimethyl-3H-thiazol-2-one

Methylammonium N-methylthio-carbamate (13.1 g, 0.105 mol; prepared from methylamine and carbonyl sulfide as described, Y. Gelernt et al. 1974, *J. Chem. Soc. Perkin Trans. 1*, 2610) was partially dissolved in MeOH (150 mL). 3-Chloro-pentane-2,4-dione (14.9 mL, 0.125 mol) was added drop-wise at room temperature, producing a gradual exotherm to 40° C. After stirring at room temperature for 1 h, the solvent was removed in vacuo. The residue was treated with $H_2O$ (50 mL) and was extracted with $CH_2Cl_2$ (3×50 mL). The combined organic fractions were washed (brine), dried ($Na_2SO_4$), filtered, and evaporated in vacuo to an amber-coloured oil. This was purified by chromatography (300 g $SiO_2$, eluting with 1:1 heptane/$Et_2O$ to obtain non-cyclized adduct, then $Et_2O$ to obtain the title product, which was recrystallized from EtOH as colourless needles (14.2 g). $^1$H-NMR ($CDCl_3$): δ2.34 (s, 3H), 2.59 (s, 3H), 3.33 (s, 3H). IR (ATR): 1655 and 1621 $cm^{-1}$ (CO str).

5-(3-Dimethylamino-acryloyl)-3,4-dim ethyl-3H-thiazol-2-one

5-Acetyl-3,4-dimethyl-3H-thiazol-2-one (4.64 g, 27.10 mmol) and dimethylformamide dimethyl acetal (8.4 mL, 59.62 mmol) were mixed in a dry, argon-flushed flask, and heated at 100° C. for 3 h. The mixture was cooled, producing some precipitation, which was enhanced by the addition of an equal volume of $Et_2O$. The resulting orange solid was filtered and washed with $Et_2O$ to give 2.73 g of the title product. $^1$H-NMR ($d_6$-DMSO): δ2.52 (s, 3H), 2.82 (bs, 3H), 3.11 (bs, 3H), 3.22 (s, 3H), 5.10 (d, 1H, J=12.2 Hz), 7.61 (d, 1H, J=11.7 Hz). IR (ATR): 1669 and 1630 $cm^{-1}$ (CO str).

Example 2

5-Acetyl-4-methyl-3H-thiazol-2-one

A solution of potassium thiocyanate (5.67 g, 58 mmol) in $Me_2CO$ (45 mL) was cooled on an ice bath and 3-chloro-pentane-2,4-dione (6.95 mL, 58 mmol) was added drop-wise. The mixture was warmed to room temperature and stirred for 6 h. After evaporation to dryness the residue was dissolved in EtOH (30 mL) and concentrated aq HCl (15 mL) was added. This mixture was heated to reflux for 14 h. After cooling it was concentrated and the resulting precipitates were filtered and washed successively with cold MeOH and $Et_2O$ to afford the title compound as a tan solid (9.1 g, 100%): mp 208-211° C. Anal. RP-HPLC: $t_R$ 6.5 min (10-70% MeCN over 20 min, purity 100%). $^1$H-NMR ($CDCl_3$): δ2.33 (s, 3H, $CH_3$), 2.38 (s, 3H, $CH_3$), 11.9 (s, 1H, NH). $^{13}$C-NMR (DMSO-$d_6$): δ15.06, 29.94, 115.53, 142.99, 170.92, 189.91. FTIR: 3094, 2850, 1669, 1622, 1579 $cm^{-1}$. MS ($ESI^+$) m/z 155.77 $(M+H)^+$. Anal. ($C_6H_7NO_2S$) C, H, N.

5-Acetyl-3-ethyl-4-methyl-3H-thiazol-2-one

KOH (1.476 g, 26.31 mmol) was added to a solution of 5-acetyl-4-methyl-3H-thiazol-2-one (4.134 g, 26.31 mmol) in DMSO (10 mL), and stirred at room temperature for 30 min. Iodoethane (2.525 mL, 31.57 mmol) was added and the resulting mixture stirred for 72 h. The reaction mixture was extracted into $CH_2Cl_2$ (5×30 mL) from $H_2O$ (30 mL) and the combined organic layers were dried over $MgSO_4$, before passing through a short $SiO_2$ gel column. Pooling of the desired fractions yielded the title compound (3.104 g, 64%).

5-(3-Dimethylamino-acryloyl)-3-ethyl-4-methyl-3H-thiazol-2-one

5-Acetyl-3-ethyl-4-methyl-3H-thiazol-2-one (3.10 g, 16.75 mmol) and dimethylfomamide dimethylacetal (2.226 mL) were combined and heated at 85° C. for 8 h. Removal of the excess acetal under vacuum left a dark residue. Treatment of this residue with $Et_2O$ containing 1% MeOH afforded the title compound as a yellow crystalline solid (1.131 g, 30%).

Example 3

5-(3-Dimethylamino-acryloyl)-4-methyl-3H-thiazol-2-one

5-Acetyl-4-methyl-3H-thiazol-2-one (0.5 g, 3.18 mmol) and tert-butoxy-bis(dimethylamino)methane (Bredereck's reagent; 2.226 mL, 0.477 mmol) were combined and heated at 80° C. for 4 h. Removal of the excess solvent under reduced pressure gave a dark residue. Treatment of this residue with EtOAc afforded the title compound as a solid product, which was collected by filtration (0.074 g, 11%). Anal. RP-HPLC: $t_R$ 10.5 min (0-60% MeCN over 20 min). $^1$H-NMR (DMSO-$d_6$): δ2.33 (3H, s, $CH_3$), 2.70 (3H, s, $NCH_3$), 3.09 (3H, s, $NCH_3$), 5.07 (1H, d, CH, J=12.0), 7.55 (1H, d, J=12.0, CH), 11.23 (1H, s, NH). MS ($ESI^+$) m/z 213.44 $(M+H)^+$.

Example 4

3-Ethyl-5-[2-(6-methoxy-pyridin-3-ylamino)-pyrimidin-4-yl]-4-methyl-3H-thiazol-2-one (33). 5-(3-Dimethylamino-acryloyl)-3-ethyl-4-methyl-3H-thiazol-2-one (80 mg, 0.333 mmol), N-(6-methoxy-pyridin-3-yl)-guanidine nitrate (76 mg, 0.333 mmol) and $K_2CO_3$ (185 mg, 1.332 mmol) were combined in of 2-methoxyethanol (4 mL) and the mixture was heated at 120° C. for 22 h. After cooling, the inorganics were filtered off and the filtrate was concentrated to dryness. The crude product was purified by $SiO_2$ gel chromatography. Pooling of the desired fractions afforded the title compound (45 mg, 39%). $^{13}$C-NMR ($d_6$-DMSO) δ: 14.5, 14.7, 37.3, 53.7, 109.0, 110.3, 128.4, 131.82, 132.4, 137.8, 138.4, 152.7, 159.5, 160.3, 164.7, 170.1. Remaining analytical data in Table 2.

The remaining compounds in Table I were prepared similarly through condensation of enaminones, prepared as described in Examples 1-4, with the appropriate aromatic guanidine salts, prepared by guanylation of the corresponding aromatic amines in the usual manner. Analytical data for the example compounds prepared are collected in Table 2.

Example 5

A typical procedure for the formation of acid addition salts of the compounds in Table 1 is as follows:

A suspension of the pyrimidine base (3 mmol) in n-butanol (100 mL) was heated at 120° C. and acid was added. A clear solution was formed, followed by formation of precipitation within ~10 minutes. The reaction mixture was then allowed to cool to room temperature. Diethyl ether (100 mL) was added and the precipitates were filtered. Recrystallisation from hot methanol afforded the desired salt.

Bis(methanesulfonic acid) salt of 3,4-dimethyl-5-[2-(4-piperazin-1-yl-phenylamino)-pyrimidin-4-yl]-3H-thiazol-2-one (38)

Yellow Solid. Anal. RP-HPLC: $t_R$=11.4 min (0-60% MeCN, purity 100%). $^1$H-NMR (D$_2$O) δ: 2.09 (s, 3H, CH$_3$), 2.69 (s, 6H, CH$_3$), 2.87 (s, 3H, CH$_3$), 3.28-3.32 (m, 8H, CH$_2$), 6.58 (m, 1H, pyrimidinyl-H), 6.85 (d, 2H, J=8.0 Hz, Ph-H), 7.14 (d, 2H, J=8.5 Hz, Ph-H), 7.74 (d, 1H, J=6.5 Hz, pyrimidinyl-H). $^{13}$C-NMR (D$_2$O) δ: 15.28, 30.46, 43.44, 46.83, 108.06, 110.17, 117.39, 122.51, 132.30, 141.99, 146.53, 154.51, 157.02, 160.79 and 170.40. Elemental analysis found C, 43.55; H, 5.26; N, 14.50. (C$_{19}$H$_{22}$N$_6$OS.2CH$_4$O$_3$S requires C, 43.89; H, 5.26; N, 14.62).

Bis(oxalic acid) salt of 3,4-dimethyl-5-[2-(4-piperazin-1-yl-phenylamino)-pyrimidin-4-yl]-3H-thiazol-2-one (38)

Yellow Solid. Anal. RP-HPLC: $t_R$=11.6 min (0-60% MeCN, purity 100%). $^1$H-NMR (DMSO-D$_6$) δ: 2.54 (s, 3H, CH$_3$), 3.16 (s, 3H, CH$_3$), 3.27-3.29 (m, 8H, CH$_2$), 6.88 (d, 1H, J=5.5 Hz, pyrimidinyl-H), 6.95 (d, 2H, J=9.0 Hz, Ph-H), 7.64 (d, 2H, J=9.0 Hz, Ph-H), 8.38 (d, 1H, J=5.0 Hz, pyrimidinyl-H), 9.42 (s, 1H, NH). $^{13}$C-NMR (D$_2$O) δ: 14.91, 30.25, 43.68, 47.37, 108.40, 110.71, 117.18, 121.02, 133.99, 138.31, 145.96, 158.38, 159.20, 160.28, 165.37, 170.48. C$_{19}$H$_{22}$N$_6$OS.2C$_2$H$_4$O$_8$ requires C, 19.11; H, 4.66; N, 14.94. found C, 49.91; H, 5.14; N, 15.49.

Example 6

Crystallization

Compound 2 (Table 1) was dissolved in a minimum volume of boiling 2-methoxyethanol. The hot solution was filtered and the filtrate was allowed to cool and stand at room temperature for 3 days. Crystal needles were formed and submitted to X-ray structure determination.

X-Ray Structure Determination

A crystal was cut from one of the clumps in the crystallization mother liquor under inert perfluoropolyether oil, and mounted on a Bruker Smart Apex diffractometer equipped with an Oxford Cryosystems low temperature device operating at 150 K. It was clear from its X-ray diffraction pattern that the sample was not a single crystal, but all the spots in the pattern could be indexed on a triclinic unit cell (Table 3) using two orientation matrices (R. A. Sparks, 2000. GEMINI, Bruker AXS, Madison, Wis., USA). This implies that the sample was in fact a two-domain non-merohedral twin; the twin law was a 180° rotation about [100], expressed by the matrix:

$$\begin{pmatrix} 1 & 0 & 0 \\ 0.402 & -1 & 0 \\ 0.559 & 0 & -1 \end{pmatrix}.$$

A sphere of data were collected with a step size of 0.30 and 30 s/image. All data were then averaged for structure analysis. An absorption correction was carried out using the multi-scan procedure SADABS (G. M. Sheldrick, 2002. SADABS Version 2.04, University of Göttingen, Germany).

The sulfur atom was located in a Patterson synthesis (G. M. Sheldrick, 2001, SHELXTL Version 6, University of Göttingen, Germany) and the remaining atoms located in iterative cycles of least squares refinement and difference Fourier maps (D. J. Watkin et al. 2003, CRYSTALS Issue 12, Chemical Crystallography Laboratory, University of Oxford, England). Analysis of the poorly-fitting data at this stage confirmed the twin law that had been derived from the diffraction pattern (ROTAX, R. I. Cooper et al. 2002, *J. Appl. Cryst.* 35, 168-174). Twinning was subsequently modelled using the procedure of Pratt, Coyle and Ibers (C. S. Pratt et al. 1971, *J. Chem. Soc.* 2146-2151). Hydrogen atoms were located in a difference map, which defined the orientation of the methyl group based on C31, and showed that the methyl group based on C41 was disordered over two orientations related by a 180° rotation about C41-C4. H-atoms were subsequently placed in ideal positions, with the weights of the H-atoms attached to C41 fixed at 0.5. All non-H atoms were modelled with anisotropic displacement parameters. The final conventional R-factor was 0.048; other crystal, data collection, and refinement parameters are listed in Table 3. Fractional atomic coordinates, bond distances and angles, anisotropic displacement parameters, and H-atom positions are listed in Table 4, Table 5, Table 6, and Table 7, respectively.

The structure of compound 2 can be unambiguously assigned to that shown in FIG. 1. Primary bond distances and angles adopt normal values. The bond distances in the C2-N3-C4-C5 moiety of the C$_3$NS ring are all less that 1.40 Å, which implies that the π-bonding is delocalised over these atoms. Average geometric parameters for C(sp$^2$)-S—C(sp$^2$) moieties in the Cambridge Database (F. H. Allen, 2002, *Acta Cryst.* B58, 380-388) are D(C—S)=1.75(2) Å and <(CSC)=95(5)°; values observed in CYC4281 are similar. Some π delocalisation is also observed about the amine function at N12, though there is a marked asymmetry in the bond lengths C10-N12 [1.370(3) Å] and N12-C13 [1.414(3) Å], and π-bonding to C10 is presumably more significant. Packing in the crystal structure is dominated by the formation, though NH—O H-bonds, of dimers of compound 2 about crystallographic inversion centres (FIG. 1). The H-bonding parameters are H12-O2: 2.00 Å, N12-O2: 2.947(3) Å, and N12-H12-O2: 154.3(15)°.

Example 7

Kinase Assays

The compounds from the examples above were investigated for their ability to inhibit the enzymatic activity of various protein kinases. This was achieved by measurement of incorporation of radioactive phosphate from ATP into appropriate polypeptide substrates. Recombinant protein kinases and kinase complexes were produced or obtained commercially. Assays were performed using 96-well plates and appropriate assay buffers (typically 25 mM β-glycerophosphate, 20 mM MOPS, 5 mM EGTA, 1 mM DTT, 1 mM Na$_3$VO$_3$, pH 7.4), into which were added 2-4 μg of active enzyme with appropriate substrates. The reactions were initiated by addition of Mg/ATP mix (15 mM MgCl$_2$+100 μM ATP with 30-50 kBq per well of [γ-$^{32}$P]-ATP) and mixtures incubated as required at 30° C. Reactions were stopped on ice, followed by filtration through p81 filterplates or GF/C filterplates (Whatman Polyfiltronics, Kent, UK). After washing 3 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (GraphPad Prism version 3.00 for Windows, GraphPad Software, San Diego Calif. USA) to determine $IC_{50}$ values (concentration of test compound which inhibits kinase activity by 50%). The results are summarized in Table 8.

Example 8

Anti-HIV Efficacy Evaluation in Fresh Human PBMCs

Representative compounds of the present invention were tested for antiviral activity against HIV-1 in human peripheral blood mononuclear cells (PBMCs) using the clinical paediatric HIV strains RoJo or WeJo. PBMCs were cultured under conditions which promote cell survival and HIV replication. Antiviral activity was tested for from 6-9 $\log_{10}$ serial dilutions of a 100 μM compound stock solution in DMSO. The following parameters were derived: $IC_{50}$ and $IC_{90}$ (concentrations inhibiting virus replication by 50 and 90%, respectively, $TC_{50}$ (concentration decreasing cell viability by 50%), and TI (therapeutic index: $TC_{50}/IC_{50}$).

Fresh PBMCs, seronegative for HIV and HBV, were isolated from screened donors (Interstate Blood Bank, Inc. Memphis, Tenn.). Cells were pelleted/washed 2-3 times by low speed centrifugation and re-suspension in PBS to remove contaminating platelets. The Leukophoresed blood was then diluted with Dulbecco's Phosphate Buffered Saline (DPBS) and layered over Lymphocyte Separation Medium (LSM; Cellgro® by Mediatech, Inc.; density 1.078±0.002 g/mL; Cat. # 85-072-CL) in a 50 mL centrifuge tube and then centrifuged. Banded PBMCs were gently aspirated from the resulting interface and subsequently washed with PBS by low speed centrifugation. After the final wash, cells were enumerated by trypan blue exclusion and re-suspended in RPMI 1640 supplemented with fetal bovine serum (FBS), and L-glutamine, Phytohemagglutinin (PHA-P, Sigma). The cells were allowed to incubate at 37° C. After incubation, PBMCs were centrifuged and resuspended in RPMI 1640 with FBS, L-glutamine, penicillin, streptomycin, gentamycin, and recombinant human IL-2 (R&D Systems, Inc). IL-2 is included in the culture medium to maintain the cell division initiated by the PHA mitogenic stimulation. PBMCs were maintained in this with bi-weekly medium changes until used in the assay protocol. Cells were kept in culture for a maximum of two weeks before being deemed too old for use in assays and discarded. Monocytes were depleted from the culture as the result of adherence to the tissue culture flask.

For the standard PBMC assay, PHA-P stimulated cells from at least two normal donors were pooled, diluted and plated in the interior wells of a 96-well round bottom microplate. Pooling of mononuclear cells from more than one donor was used to minimise the variability observed between individual donors, which results from quantitative and qualitative differences in HIV infection and overall response to the PHA and IL-2 of primary lymphocyte populations. Each plate contained virus/cell control wells (cells plus virus), experimental wells (drug plus cells plus virus) and compound control wells (drug plus media without cells, necessary for MTS monitoring of cytotoxicity). Since HIV-1 is not cytopathic to PBMCs, this allows the use of the same assay plate for both antiviral activity and cytotoxicity measurements. Test drug dilutions were prepared in microtiter tubes and each concentration was placed in appropriate wells using the standard format. A predetermined dilution of virus stock was placed in each test well (final MOI≅0.1). The PBMC cultures were maintained for seven days following infection at 37° C., 5% $CO_2$ After this period, cell-free supernatant samples were collected for analysis of reverse transcriptase activity and/or HIV p24 content. Following removal of supernatant samples, compound cytotoxicity was measured by addition of MTS to the plates for determination of cell viability. Wells were also examined microscopically and any abnormalities were noted.

Reverse Transcriptase Activity Assay

A microtiter plate-based reverse transcriptase (RT) reaction was utilised (Buckheit et al., AIDS Research and Human Retroviruses 7:295-302, 1991). Tritiated thymidine triphosphate ($^3$H-TTP, 80 Ci/mmol, NEN) was received in 1:1 $dH_2O$: Ethanol at 1 mCi/mL. Poly rA:oligo dT template:primer (Pharmacia) was prepared as a stock solution, followed by aliquoting and storage at −20° C. The RT reaction buffer was prepared fresh on a daily basis. The final reaction mixture was prepared by combining $^3$H-TTP, $dH_2O$, poly rA:oligo dT stock and reaction buffer. This reaction mixture was placed in a round bottom microtiter plate and supernatant containing virus was added and mixed. The plate was incubated at 37° C. for 60 minutes. Following incubation, the reaction volume was spotted onto DE81 filter-mats (Wallac), in a sodium phosphate buffer or 2×SSC (Life Technologies). Next they were washed in distilled water, in 70% ethanol, and then dried. Incorporated radioactivity (counts per minute, CPM) was quantified using standard liquid scintillation techniques.

Results

Based on TI values as defined above, the following compounds of the present invention were found to posses anti-HIV activity:

Highly Active (TI≧50) Compounds:
5-[2-(3-Iodo-4-methyl-phenylamino)-pyrimidin-4-yl]-3,4-dimethyl-3H-thiazol-2-one (14),
3,4-Dimethyl-5-[2-(3-trifluoromethyl-phenylamino)-pyrimidin-4-yl]-3H-thiazol-2-one (19),
5-[2-(4-Dimethylamino-3-nitro-phenylamino)-pyrimidin-4-yl]-3,4-dimethyl-3H-thiazol-2-one (22),
5-[2-(4-Dimethylamino-3-nitro-phenylamino)-pyrimidin-4-yl]-3-ethyl-4-methyl-3H-thiazol-2-one (29),
5-[2-(6-Chloro-pyridin-3-ylamino)-pyrimidin-4-yl]-3,4-dimethyl-3H-thiazol-2-one (32),
N-{3-[4-(3,4-Dimethyl-2-oxo-2,3-dihydro-thiazol-5-yl)-pyrimidin-2-ylamino]-benzyl}-methane-sulfonamide (55),
N-{3-[4-(3,4-Dimethyl-2-oxo-2,3-dihydro-thiazol-5-yl)-pyrimidin-2-ylamino]-benzyl}-C,C,C-trifluoro-methane-sulfonamide (58), and
N-{3-[4-(3,4-Dimethyl-2-oxo-2,3-dihydro-thiazol-5-yl)-pyrimidin-2-ylamino]-5-trifluoromethyl-phenyl}-acetamide (64).

Active (5≦TI≦50) Compounds:
5-[2-(4-Fluoro-phenylamino)-pyrimidin-4-yl]-3,4-dimethyl-3H-thiazol-2-one (2),
3,4-Dimethyl-5-[2-(4-methyl-3-nitro-phenylamino)-pyrimidin-4-yl]-3H-thiazol-2-one (11),
5-[2-(4-Chloro-3-methyl-phenylamino)-pyrimidin-4-yl]-3,4-dimethyl-3H-thiazol-2-one (15),
3-[4-(3,4-Dimethyl-2-oxo-2,3-dihydro-thiazol-5-yl)-pyrimidin-2-ylamino]-benzonitrile (16),
3,4-Dimethyl-5-[2-(4-methyl-3-trifluoromethyl-phenylamino)-pyrimidin-4-yl]-3H-thiazol-2-one (21),
3-Ethyl-4-methyl-5-[2-(3-nitro-phenylamino)-pyrimidin-4-yl]-3H-thiazol-2-one (23),
3-Ethyl-5-[2-(6-methoxy-pyridin-3-ylamino)-pyrimidin-4-yl]-4-methyl-3H-thiazol-2-one (33),
3,4-Dimethyl-5-[2-(4-piperazin-1-yl-phenylamino)-pyrimidin-4-yl]-3H-thiazol-2-one (38),
N-{4-[4-(3,4-Dimethyl-2-oxo-2,3-dihydro-thiazol-5-yl)-pyrimidin-2-ylamino]-benzyl}-acetamide (59),
3-[4-(3,4-Dimethyl-2-oxo-2,3-dihydro-thiazol-5-yl)-pyrimidin-2-ylamino]-benzenesulfonamide (60), N-{3-[4-(3,4-Dimethyl-2-oxo-2,3-dihydro-thiazol-5-yl)-pyrimidin-2-ylamino]-5-trifluoromethyl-phenyl}-acetamide (64), and 4-[4-(3,4-Dimethyl-2-oxo-2,3-dihydro-thiazol-5-yl)-pyrimidin-2-ylamino]-N-(2-methoxy-ethyl)-benzenesulfonamide (65).

Example 9

GSK3β and GSK3α Assays

Both isoforms of GSK3 (α and β) are involved in the regulation of glycogen synthase activity—key enzyme in the glycogen metabolism. The inhibitory potency of example compounds was determined using in vitro kinase assays with recombinant human GSK3-α and -β; the $IC_{50}$ values determined are presented in Table 9.

A 10-point titration was set up to determine the $IC_{50}$ values of selected example compounds against GSK3β. Assays were performed using 96-well microtiter plates with a final volume of 25 μL per well. Each assay contained 1.5 units of GSK3β (New England Biolabs), 200 μM CREB phosphopeptide (KRREILSRRPpSYR, Alta Biosciences), 20 mM Tris HCl pH7.5, 5 mM DTT, 15 mM $MgCl_2$ supplemented with 100 μM ATP and 0.5 μCi of [γ-$^{32}$P] ATP plus or minus inhibitor in 2% DMSO. Assays were carried out for 30 minutes at 30° C. before stopping the reaction by the addition of an equal volume of 75 mM aqueous phosphoric acid. Samples were then spotted onto a p81 filterplate (Whatman) and a vacuum was applied. Wells were washed 3 times with 200 μL of dilute aqueous phosphoric acid before the addition of 50 μL Microscint 40 per well. Incorporation of radioactivity was determined on a Topcount microplate scintillation counter (Packard).

GSK3α (Upstate) was assayed exactly as described above except that 1 ng of enzyme was added per assay point.

Example 10

DYRK1A Assay

Dual specificity tyrosine phosphorylation regulated kinase 1A (DYRK1A) has been proposed, amongst other functions, to play a role in the regulation of glycogen metabolism in a way similar to GSK3. Some of the example compounds of the present invention were screened against recombinant human DYRK1A in vitro and the determined $IC_{50}$ values are shown in Table 9. According to our current knowledge inhibition of DYRK1A will have additional positive effect on stimulation of glycogen synthase.

A 10-point titration was set up to determine the $IC_{50}$ values of selected example compounds against DYRK1A. Assays were performed using 96-well microtiter plates and a final volume of 25 μL/well. Each assay contained 2.3 milliunits of DYRK1A (Upstate), 50 μM Woodtide peptide (KKISGRLSPIMTEQ, Upstate), 20 mM Tris HCl pH 8.0, 10 mM DTT, 5 mM EGTA, 1 mM $NaVO_3$, 31 mM β-glycerophosphate, 15 mM $MgCl_2$ supplemented with 100 μM ATP and 0.5 μCi of [γ-$^{32}$P] ATP plus or minus inhibitor in 2% DMSO. Assays were carried out for 60 minutes at 30° C. before stopping the reaction by the addition of an equal volume of 75 mM aqueous phosphoric acid. Samples were then spotted onto a p81 filterplate (Whatman) and a vacuum applied. Wells were washed 3 times with 200 μL of dilute aqueous phosphoric acid before the addition of 50 μL Microscint 40 per well. Incorporation of radioactivity was determined on a Topcount microplate scintillation counter (Packard).

Example 11

Differentiation of Adipocytes and Myotubes

3T3-L1 mouse pre-adipocytes were grown in DMEM medium supplemented with 10% foetal calf serum (FCS) and penicillin/streptomycin until fully confluent. Cell differentiation was initiated by the addition of 0.5 mM IBMX (2-isobutyl-1-methylxanthine), 0.25 μM dexamethasone and 1 μg/mL insulin into the growth media. The differentiation medium was replaced after 4 days and 7 days. After the initiation of differentiation the cells were grown for an additional 3 days in DMEM, 10% FCS and antibiotics.

Rat myotubes were differentiated from L6.G8.C5 myoblasts, which were grown in DMEM, 10% FCS and antibiotics until confluent. The medium was then removed, cells washed with PBS and differentiation medium containing minimal essential media eagles (alpha modified) supplemented with 2% FCS and antibiotics. The cells were cultured for 3-4 days until >90% of cells had formed multinucleated myotubes. The differentiated cells were then used for determination of glycogen synthase activation after treatment with GSK3 inhibitor example compounds.

Example 12

Glycogen Synthase Activation in Cultured Cells

HEK293 cells, mouse adipocytes or rat myotubes were treated in 10-cm Petri dishes with different concentrations of GSK3 inhibitor example compounds for 90 minutes. At the end of the treatment period the cells were washed and scraped in ice cold PBS buffer supplemented with 20 mM NaF. The cells were pelleted by centrifugation and lysed in 300 μL buffer (50 mM.HEPES pH 7.5, 10 mM EDTA, 100 mM NaF, 5 mM DTT, protease inhibitor cocktail (Sigma)). After incubation for 30 min on ice the samples were cleared by centrifugation. The activity of glycogen synthase was determined in the soluble fraction at two different concentrations of glucose-6-phosphatase—low (0.1 mM) and high (10 mM). The reaction was carried out for 30 min (buffer: 50 mM Tris pH 7.8, 20 mM EDTA, 25 mM NaF, 5 mM DTT). The reaction mixture (total volume of 90 μL) contained 1% glycogen, 0.3 mM UDP-glucose and 0.06 μCi $^{14}$C-UDP-glucose. Reaction was stopped by transfer of 70 μL to a GFC 96-well filter plate, containing 140 μL 100% ethanol and the glycogen was allowed to precipitate for 1 h at 4° C. The wells were washed 2 times with 200 μL 66% ethanol and than allowed to dry. Subsequently, 100 μL of scintillation liquid was added, and plates were sealed and counted in a Packard Topcounter. Glycogen synthase activation was calculated as the ratio between the incorporation of labelled $^{14}$C-UDP-glucose in glycogen at low and high concentration of UDP-glucose (fractional velocity).

The ability of GSK3 inhibitors to activate glycogen synthase was determined in HEK293 cells, mouse adipocytes and rat myotubed. The $EC_{50}$ values determined and the maximum fold induction normalised to the effect of 40 mM LiCl (in %) are presented in Table 10. The compounds tested activated glycogen synthase in all three cellular systems with $EC_{50}$ values in the sub-micromolar to low micromolar concentration range. Most of them exceeded the stimulation induced by 40 mM LiCl (the highest compound concentration used in the assay was 20 μM).

Example 13

PEPCK Gene Expression Assay—qPCR

PEPCK gene expression was studied in HEPG2 (hepatocarcinoma) cells, seeded in 6-well plate at 1×10$^7$ cells per well. The cells were serum-starved for 20 hours before treatment with dexamethasone/cAMP (stimulator of PEPCK gene expression) in the presence or absence of insulin or GSK3 inhibitor example compounds. After 3 hours treatment the cells were harvested, lysed and RNA extracted using mini RNeasy spin columns (Quiagen). The primer set COD2063/COD2064 (350 bp) was used for the PEPCK gene. The one step RT-PCR was carried out using the Lightcycler-RNA Master SYBR Green 1 Kit. The qPCR analysis calculates the number of the PCR cycles required for the PCR product amplification to reach logarithmic phase. QPCR for a housekeeping gene—28S—was used for normalisation.

PEPCK is a key enzyme in gluconeogenesis in the liver and it is known to be negatively regulated by insulin via inhibition of GSK3. The effect of example compounds on PEPCK gene expression was studied in HEPG2 cells treated with dexamethasone/cAMP (a positive regulator PEPCK gene expression) in the presence or absence of insulin or GSK3 inhibitors. The level of PEPCK gene transcription expressed as a percentage of the dexamethasone-induced stimulation is shown in Table 11. Example compound inhibitors of GSK3 were efficient in the abolishment of dexamethasone/cAMP induced stimulation of PEPCK gene expression in HEPG2 cells. Some of the tested compounds were significantly more potent than the insulin. These results suggest the potential use of GSK3 inhibitors in the regulation of hepatic gluconeogenesis, which is defective and contributes to the hyperglycaemia in diabetic patients.

Example 14

Effect of GSK3 Inhibitor Example Compounds on Oral Glucose Tolerance in Male ZDF Rats The ability of example compounds of the present invention to improve glucose metabolism was tested in 12-13 week old male ZDF fa/fa rats. The test animals (10-15 mmol/L fasting glucose level) were dosed twice at 30 mg/kg and the glucose challenge was given at time 0. The AUC was determined from −270 to 180 min and 0 to 180 min and the blood levels of the tested compounds were determined at 30 and 60 min after the glucose load. The results are listed in Table 12. A trend of decreased blood glucose levels was observed (statistically significant only for compounds 66 and 68). Four of the compounds had some oral bioavailability (64, 66, 67 and 68), which correlated with a moderate decrease of the glucose AUC. Most of these blood levels were below the $EC_{50}$ values determined in cellular assays.

12-13 weeks old male ZDF fa/fa rats were used to study the effect of example compounds on oral glucose tolerance. The animals were single-housed under semi-barrier conditions with controlled temperature (22±2° C.) on a 12/12 hours light/dark cycle; energy enriched pelleted chow (m Z Ereich; Act. No. V1185-000; Ssniff™ Spezialitaeten GmbH, D-59494 Soest, Germany) containing 23% protein, 6% fat, 61.7% carbohydrates, 3.3% fibre and 6% ash, and tap water acidified with HCl, were allowed ad libitum. Body weight was recorded three times per week. Test compounds were dissolve in a formulation of 10% DMSO, 5% Tween, 5% Span 20, 30% PEG 400 and 50% water (v/v) to provide final solutions at 5 mg/mL concentration. Each experimental group contained 7 animals. After an 16 h overnight fast the test compounds were administered at 30 mg/kg per os twice (at −270 min and −30 min) before the oral glucose tolerance test was commenced (2 g glucose/kg per os as a 40% solution introduced via feeding tube). A control group was dosed in a similar manner with the vehicle only. Blood sampling for blood glucose measurement (20 μL blood) was performed at −270, 0, 15, 30, 60, 90, 120 and 180 min. Mixed venous blood was collected from the tail vein into 20-μL glass capillaries, which were placed in a standard tube filled with 1 mL solution for hemolysis. Glucose levels were measured using the glucose oxidase procedure (Super G Glukosemessgeraet; Dr Mueller Geraetebau, Freital, Germany). In addition, 50 μL blood samples were taken at 30 and 60 min after the glucose dose, placed in heparinized tubes, which were then frozen immediately in liquid nitrogen. The bioanalytical method used employed isocratic elution liquid chromatography—tandem mass spectrometry in electrospray positive ion multiple reaction monitoring mode.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

REFERENCES

1. Manning, G.; Whyte, D. B.; Martinez, R.; Hunter, T.; Sudarsanam, S. The protein kinase complement of the human genome. *Science* 2002, 298, 1912-1934.
2. Kostich, M.; English, J.; Madison, V.; Gheyas, F.; Wang, L. et al. Human members of the eukaryotic protein kinase family. *Genome Biology* 2002, 3, research 0043.0041-0043.0012.
3. Dancey, J.; Sausville, E. A. Issues and progress with protein kinase inhibitors for cancer treatment. *Nat. Rev. Drug Disc.* 2003, 2, 296-313.
4. Cockerill, G. S.; Lackey, K. E. Small molecule inhibitors of the class 1 receptor tyrosine kinase family. *Current Topics in Medicinal Chemistry* 2002, 2, 1001-1010.
5. Fabbro, D.; Ruetz, S.; Buchdunger, E.; Cowan-Jacob, S. W.; Fendrich, G. et al. Protein kinases as targets for anticancer agents: from inhibitors to useful drugs. *Pharmacol. Ther.* 2002, 93, 79-98.
6. Cohen, P. Protein kinases—the major drug targets of the twenty-first century? *Nat. Rev. Drug Disc.* 2002, 1, 309-315.
7. Bridges, A. J. Chemical inhibitors of protein kinases. *Chem. Rev.* 2001, 101(8), 2541-2571.
8. Wang, S.; Meades, C.; Wood, G.; Osnowski, A.; Fischer, P. M. N-(4-(4-methylthiazol-5-yl)pyrimidin-2-yl)-N-phenylamines as antiproliferative compounds. PCT Intl. Patent Appl. Publ. WO 2003029248; Cyclacel Limited, UK.
9. Wu, S. Y.; McNae, I.; Kontopidis, G.; McClue, S. J.; McInnes, C. et al. Discovery of a Novel Family of CDK Inhibitors with the Program LIDAEUS: Structural Basis for Ligand-Induced Disordering of the Activation Loop. *Structure* 2003, 11, 399-410.
10. Fischer, P. M.; Wang, S.; Wood, G. Inhibitors of cyclin dependent kinases as anti-cancer agent. PCT Intl. Patent Appl. Publ. WO 02/079193; Cyclacel Limited, UK.
11. Wang, S.; Fischer, P. M. Anti-cancer compounds. US Patent Appl. Publ. 2002/0019404.
12. Fischer, P. M.; Wang, S. 2-substituted 4-heteroaryl-pyrimidines and their use in the treatment of proliferative disorders. PCT Intl. Patent Appl. Publ. WO 2001072745; Cyclacel Limited, UK.
13. Knockaert, M.; Greengard, P.; Meijer, L. Pharmacological inhibitors of cyclin-dependent kinases. *Trends Pharmacol. Sci.* 2002, 23, 417-425.
14. Fischer, P. M.; Endicott, J.; Meijer, L. Cyclin-dependent kinase inhibitors. *Progress in Cell Cycle Research*; Editions de la Station Biologique de Roscoff: Roscoff, France, 2003; pp 235-248.
15. Fravolini, A.; Grandolini, G.; Martani, A. New heterocyclic ring systems from α-hydroxymethylene ketones. V. Reaction of 2-methyl-6-hydroxymethylene-4,5,6,7-tetrahydrobenzothiazol-7-one with amines and amidines. *Gazz. Chim. Ital.* 1973, 103, 1063-1071.

16. Cleaver, L.; Croft, J. A.; Ritchie, E.; Taylor, W. C. Chemical studies of the Proteaceae. IX. Synthesis of 5-alkylresorcinols from aliphatic precursors. *Aust. J. Chem.* 1976, 29, 1989-2001.
17. Fadda, A. A.; El-Houssini, M. S. Synthesis of cyclic ketones by activated nitrites. *J. Ind. Chem. Soc.* 1990, 67, 915-917.
18. Kost, A. N.; Ovseneva, L. G. Synthesis of 4-substituted dihydroresorcinols. *Zh. Obshch. Khim* 1962, 32, 3983-3986.
19. Lehmann, G.; Luecke, B.; Schick, H.; Hilgetag, G. 2-Substituted 7-oxo-4,5,6,7-tetrahydrobenzothiazoles. *Z. Chem.* 1967, 7, 422.
20. Bell, R. P.; Davis, G. G. Kinetics of the bromination of some enols and their anions. *J. Chem. Soc* 1965, 353-361.
21. Fravolini, A.; Grandolini, G.; Martani, A. New heterocyclic ring systems from α-hydroxymethylene ketones. III. Pyrazolobenzothiazoles and thiazolo-benzoisoxazoles. *Gazz. Chim. Ital.* 1973, 103, 755-769.
22. Bredereck, H.; Effenberger, F.; Botsch, H. Acid amide reactions. XLV. Reactivity of formamidines, dimethylformamide diethyl acetal (amide acetal), and bis(dimethylamino)methoxymethane (aminal ester). *Chem. Ber.* 1964, 97, 3397-3406.
23. Wang D, De la Fuente C, Deng L, Wang L, Zilberman I, Eadie C, Healey M, Stein D, Denny T, Harrison L E, Meijer L, Kashanchi F. Inhibition of human immunodeficiency virus type 1 transcription by chemical cyclin-dependent kinase inhibitors. *J. Virol.* 2001; 75: 7266-7279.
24. Chen, Y. H.; Hansen, L.; Chen, M. X.; Bjorbaek, C.; Vestergaard, H.; Hansen, T.; Cohen, P. T.; Pedersen, O. *Diabetes*, 1994, 43, 1234.
25. Nikoulina, S. E.; Ciaraldi, T. P.; Mudaliar, S.; Mohideen, P.; Carter, L.; Henry, R. R. *Diabetes*, 2000, 49, 263.
26. Goedert, M. *Curr. Opin. Gen. Dev.*, 2001, 11, 343.
27. Mattson, M. P. *Nat. Rev. Mol. Cell. Biol.*, 2000, 1, 120.
28. Zhu, A. J.; Watt, F. M. *Development*, 1999, 126, 2285.
29. DasGupta, R.; Fuchs, E. *Development*, 1999, 126, 4557.
30. Sunkel et al., *J. Cell Sci.*, 1988, 89, 25.
31. Llamazares et al., *Genes Dev.*, 1991, 5, 2153.
32. Glover et al., *Genes Dev.*, 1998, 12, 3777.
33. Lee et al., *Proc. Natl. Acad. Sci. USA*, 1998, 95, 9301.
34. Leung et al., *Nat. Struct. Biol.*, 2002, 9, 719.
35. Kauselmann et al., *EMBO J.*, 1999, 18, 5528.
36. Nigg, *Curr. Opin. Cell Biol.*, 1998, 10, 776.
37. Yuan et al., *Cancer Res.*, 2002, 62, 4186.
38. Seong et al., *J. Biol. Chem.*, 2002, 277, 32282.
39. Lane et al., *J. Cell. Biol.*, 1996, 135, 1701.
40. Cogswell et al., *Cell Growth Differ.*, 2000, 11, 615.
41. Liu et al., *Proc. Natl. Acad. Sci. USA*, 2002, 99, 8672.
42. Toyoshima-Morimoto et al., *Nature*, 2001, 410, 215.
43. Roshak et al., *Cell. Signalling*, 2000, 12, 405.
44. Smits et al., *Nat. Cell Biol.*, 2000, 2, 672.
45. van Vugt et al., *J. Biol. Chem.*, 2001, 276, 41656.
46. Sumara et al., *Mol. Cell*, 2002, 9, 515.
47. Golan et al., *J. Biol. Chem.*, 2002, 277, 15552.
48. Kotani et al., *Mol. Cell*, 1998, 1, 371.
49. Feng et al., *Cell Growth Differ.*, 2001, 12, 29.
50. Dai et al., *Oncogene*, 2002, 21, 6195.
51. Nurse, *Nature*, 1990, 344, 503.
52. Nigg, *Nat. Rev. Mol. Cell Biol.*, 2001, 2, 21.
53. Hagting et al., *EMBO J.*, 1998, 17, 4127.
54. Hagting et al., *Curr. Biol.*, 1999, 9, 680.
55. Yang et al., *J. Biol. Chem.*, 2001, 276, 3604.
56. Takizawa et al., *Curr. Opin. Cell Biol.*, 2000, 12, 658.
57. Seki et al., *Mol. Biol. Cell*, 1992, 3, 1373.
58. Heald et al., *Cell*, 1993, 74, 463.
59. Dalal et al., *Mol. Cell. Biol.*, 1999, 19, 4465.
60. Toyoshima-Morimoto et al., *Nature*, 2001, 410, 215.
61. Toyoshima-Morimoto et al., *EMBO Rep.*, 2002, 3, 341.
62. Wang et al., *Mol. Cell. Biol.*, 2002, 22, 3450.
63. Tyrrell, E.; Brookes, P. Synthesis 2003, 469-483.
64. Rocca, P.; Cochennec, C.; Marsais, F.; Thomas-dit-Dumont, L.; Mallet, M. et al. J. Org. Chem. 1993, 58, 7832-7838.
65. Bredereck, H.; Effenberger, F.; Botsch, H. Chem. Ber. 1964, 97, 3397-3406.
66. Zimmermann, J.; Caravatti, G.; Mett, H.; Meyer, T.; Müller, M. et al. Arch. Pharm. Pharm. Med. Chem. 1996, 329, 371-376.
67. Haselsberger, K.; Peterson, D. C.; Thomas, D. G.; Darling, J. L. Anti Cancer Drugs 1996, 7, 331-8.
68. Loveland, B. E.; Johns, T. G.; Mackay, I. R.; Vaillant, F.; Wang, Z. X.; Hertzog, P. J. Biochemistry International 1992, 27, 501-10.

TABLE 1

Exemplified compounds.
Structure

| No. | X | $R^1$ | $R^9$ | $R^8$ | $R^{10}$ | $R^{11}$ | Name |
|-----|---|-------|-------|-------|----------|----------|------|
| 1 | C | Me | H | $NO_2$ | H | H | 3,4-Dimethyl-5-[2-(3-nitro-phenylamino)-pyrimidin-4-yl]-3H-thiazol-2-one |
| 2 | C | Me | F | H | H | H | 5-[2-(4-Fluoro-phenylamino)-pyrimidin-4-yl]-3,4-dimethyl-3H-thiazol-2-one |

TABLE 1-continued

Exemplified compounds. Structure

| No. | X | R¹ | R⁹ | R⁸ | R¹⁰ | R¹¹ | Name |
|---|---|---|---|---|---|---|---|
| 3 | C | Me | OH | H | H | H | 5-[2-(4-Hydroxy-phenylamino)-pyrimidin-4-yl]-3,4-dimethyl-3H-thiazol-2-one |
| 4 | C | Me | Cl | H | H | H | 5-[2-(4-Chloro-phenylamino)-pyrimidin-4-yl]-3,4-dimethyl-3H-thiazol-2-one |
| 5 | C | Me | Br | H | H | H | 5-[2-(4-Bromo-phenylamino)-pyrimidin-4-yl]-3,4-dimethyl-3H-thiazol-2-one |
| 6 | C | Me | OMe | H | H | H | 5-[2-(4-Methoxy-phenylamino)-pyrimidin-4-yl]-3,4-dimethyl-3H-thiazol-2-one |
| 7 | C | Me | H | OH | H | H | 5-[2-(3-Hydroxy-phenylamino)-pyrimidin-4-yl]-3,4-dimethyl-3H-thiazol-2-one |
| 8 | C | Me | NMe₂ | H | H | H | 5-[2-(4-Dimethylamino-phenylamino)-pyrimidin-4-yl]-3,4-dimethyl-3H-thiazol-2-one |
| 9 | C | Me | Morpholin-4-yl | H | H | H | 3,4-Dimethyl-5-[2-(4-morpholin-4-yl-phenylamino)-pyrimidin-4-yl]-3H-thiazol-2-one |
| 10 | C | Me | F | NO₂ | H | H | 5-[2-(4-Fluoro-3-nitro-phenylamino)-pyrimidin-4-yl]-3,4-dimethyl-3H-thiazol-2-one |
| 11 | C | Me | Me | NO₂ | H | H | 3,4-Dimethyl-5-[2-(4-methyl-3-nitro-phenylamino)-pyrimidin-4-yl]-3H-thiazol-2-one |
| 12 | C | Me | F | Me | H | H | 5-[2-(4-Fluoro-3-methyl-phenylamino)-pyrimidin-4-yl]-3,4-dimethyl-3H-thiazol-2-one |
| 13 | C | Me | 4-Methyl-piperazin-1-yl | H | H | H | 3,4-Dimethyl-5-{2-[4-(4-methyl-piperazin-1-yl)-phenylamino]-pyrimidin-4-yl}-3H-thiazol-2-one |
| 14 | C | Me | Me | I | H | H | 5-[2-(3-Iodo-4-methyl-phenylamino)-pyrimidin-4-yl]-3,4-dimethyl-3H-thiazol-2-one |
| 15 | C | Me | Cl | Me | H | H | 5-[2-(4-Chloro-3-methyl-phenylamino)-pyrimidin-4-yl]-3,4-dimethyl-3H-thiazol-2-one |
| 16 | C | Me | H | CN | H | H | 3-[4-(3,4-Dimethyl-2-oxo-2,3-dihydro-thiazol-5-yl)-pyrimidin-2-ylamino]-benzonitrile |

TABLE 1-continued

Exemplified compounds.
Structure

[Chemical structure showing a thiazol-2-one connected via pyrimidine to a phenylamine with substituents R1, R8, R9, R10, R11, and X]

| No. | X | R¹ | R⁹ | R⁸ | R¹⁰ | R¹¹ | Name |
|---|---|---|---|---|---|---|---|
| 17 | C | Me | 4-Acetyl-piperazin-1-yl | H | H | H | 5-{2-[4-(4-Acetyl-piperazin-1-yl)-phenylamino]-pyrimidin-4-yl}-3,4-dimethyl-3H-thiazol-2-one |
| 18 | C | Me | Cl | CH₂OH | H | H | 5-[2-(4-Chloro-3-hydroxymethyl-phenylamino)-pyrimidin-4-yl]-3,4-dimethyl-3H-thiazol-2-one |
| 19 | C | Me | H | CF₃ | H | H | 3,4-Dimethyl-5-[2-(3-trifluoromethyl-phenylamino)-pyrimidin-4-yl]-3H-thiazol-2-one |
| 20 | C | Me | H | NO₂ | Me | H | 3,4-Dimethyl-5-[2-(2-methyl-5-nitro-phenylamino)-pyrimidin-4-yl]-3H-thiazol-2-one |
| 21 | C | Me | Me | CF₃ | H | H | 3,4-Dimethyl-5-[2-(4-methyl-3-trifluoromethyl-phenylamino)-pyrimidin-4-yl]-3H-thiazol-2-one |
| 22 | C | Me | NMe₂ | NO₂ | H | H | 5-[2-(4-Dimethylamino-3-nitro-phenylamino)-pyrimidin-4-yl]-3,4-dimethyl-3H-thiazol-2-one |
| 23 | C | Et | H | NO₂ | H | H | 3-Ethyl-4-methyl-5-[2-(3-nitro-phenylamino)-pyrimidin-4-yl]-3H-thiazol-2-one |
| 24 | C | Et | Cl | CO₂H | H | H | 2-Chloro-5-[4-(3-ethyl-4-methyl-2-oxo-2,3-dihydro-thiazol-5-yl)-pyrimidin-2-ylamino]-benzoic acid |
| 25 | C | Et | Cl | CO₂Me | H | H | 2-Chloro-5-[4-(3-ethyl-4-methyl-2-oxo-2,3-dihydro-thiazol-5-yl)-pyrimidin-2-ylamino]-benzoic acid methyl ester |
| 26 | C | Et | NMe₂ | H | H | H | 5-[2-(4-Dimethylamino-phenylamino)-pyrimidin-4-yl]-3-ethyl-4-methyl-3H-thiazol-2-one |
| 27 | C | Et | Morpholin-4-yl | H | H | H | 3-Ethyl-4-methyl-5-[2-(4-morpholin-4-yl-phenylamino)-pyrimidin-4-yl]-3H-thiazol-2-one |
| 28 | C | Et | Me | NO₂ | H | H | 3-Ethyl-4-methyl-5-[2-(4-methyl-3-nitro-phenylamino)-pyrimidin-4-yl]-3H-thiazol-2-one |
| 29 | C | Et | NMe₂ | NO₂ | H | H | 5-[2-(4-Dimethylamino-3-nitro-phenylamino)-pyrimidin-4-yl]-3-ethyl-4-methyl-3H-thiazol-2-one |

TABLE 1-continued

Exemplified compounds.
Structure

| No. | X | R¹ | R⁹ | R⁸ | R¹⁰ | R¹¹ | Name |
|---|---|---|---|---|---|---|---|
| 30 | C | 3-Methyl-butyl | H | NO₂ | H | H | 4-Methyl-3-(3-methyl-butyl)-5-[2-(3-nitro-phenylamino)-pyrimidin-4-yl]-3H-thiazol-2-one |
| 31 | C | 3-Methyl-butyl | Cl | H | H | H | 5-[2-(4-Chloro-phenylamino)-pyrimidin-4-yl]-4-methyl-3-(3-methyl-butyl)-3H-thiazol-2-one |
| 32 | N | Me | Cl | — | H | H | 5-[2-(6-Chloro-pyridin-3-ylamino)-pyrimidin-4-yl]-3,4-dimethyl-3H-thiazol-2-one |
| 33 | N | Et | OMe | — | H | H | 3-Ethyl-5-[2-(6-methoxy-pyridin-3-ylamino)-pyrimidin-4-yl]-4-methyl-3H-thiazol-2-one |
| 34 | N | 3-Methyl-butyl | Cl | — | H | H | 5-[2-(6-Chloro-pyridin-3-ylamino)-pyrimidin-4-yl]-4-methyl-3-(3-methyl-butyl)-3H-thiazol-2-one |
| 35 | N | 3-Methyl-butyl | OMe | — | H | H | 5-[2-(6-Methoxy-pyridin-3-ylamino)-pyrimidin-4-yl]-4-methyl-3-(3-methyl-butyl)-3H-thiazol-2-one |
| 36 | C | Me | I | H | H | H | 5-[2-(4-Iodo-phenylamino)-pyrimidin-4-yl]-3,4-dimethyl-3H-thiazol-2-one |
| 37 | C | Me | H | NO₂ | NMe₂ | H | 5-[2-(2-Dimethylamino-5-nitro-phenylamino)-pyrimidin-4-yl]-3,4-dimethyl-3H-thiazol-2-one |
| 38 | C | Me | Piperazin-1-yl | H | H | H | 3,4-Dimethyl-5-[2-(4-piperazin-1-yl-phenylamino)-pyrimidin-4-yl]-3H-thiazol-2-one |
| 39 | C | Me | Me | NH₂ | H | H | 5-[2-(3-Amino-4-methyl-phenylamino)-pyrimidin-4-yl]-3,4-dimethyl-3H-thiazol-2-one |
| 40 | C | H | H | NO₂ | H | H | 4-Methyl-5-[2-(3-nitro-phenylamino)-pyrimidin-4-yl]-3H-thiazol-2-one |
| 41 | C | H | Me | NO₂ | H | H | 4-Methyl-5-[2-(4-methyl-3-nitro-phenylamino)-pyrimidin-4-yl]-3H-thiazol-2-one |
| 42 | C | Me | CH₂NHCOMe | H | H | H | N-{3-[4-(3,4-Dimethyl-2-oxo-2,3-dihydro-thiazol-5-yl)-pyrimidin-2-ylamino]-benzyl}-acetamide |

TABLE 1-continued

Exemplified compounds. Structure

| No. | X | R¹ | R⁹ | R⁸ | R¹⁰ | R¹¹ | Name |
|---|---|---|---|---|---|---|---|
| 43 | C | Et | H | OH | H | H | 3-Ethyl-5-[2-(3-hydroxy-phenylamino)-pyrimidin-4-yl]-4-methyl-3H-thiazol-2-one |
| 44 | C | Me | Piperazin-1-yl | Cl | H | H | 5-[2-(3-Chloro-4-piperazin-1-yl-phenylamino)-pyrimidin-4-yl]-3,4-dimethyl-3H-thiazol-2-one |
| 45 | C | Et | F | H | H | H | 3-Ethyl-5-[2-(4-fluoro-phenylamino)-pyrimidin-4-yl]-4-methyl-3H-thiazol-2-one |
| 46 | C | Et | Cl | H | H | H | 5-[2-(4-Chloro-phenylamino)-pyrimidin-4-yl]-3-ethyl-4-methyl-3H-thiazol-2-one |
| 47 | C | Et | Me | OH | H | H | 3-Ethyl-5-[2-(3-hydroxy-4-methyl-phenylamino)-pyrimidin-4-yl]-4-methyl-3H-thiazol-2-one |
| 48 | C | Et | Cl | CF₃ | H | H | 5-[2-(4-Chloro-3-trifluoromethyl-phenylamino)-pyrimidin-4-yl]-3-ethyl-4-methyl-3H-thiazol-2-one |
| 49 | C | Me | H | 4-Acetyl-piperazin-1-yl | H | H | 5-{2-[3-(4-Acetyl-piperazin-1-yl)-phenylamino]-pyrimidin-4-yl}-3,4-dimethyl-3H-thiazol-2-one |
| 50 | C | Et | H | OMe | H | H | 3-Ethyl-5-[2-(3-methoxy-phenylamino)-pyrimidin-4-yl]-4-methyl-3H-thiazol-2-one |
| 51 | C | Et | Cl | Me | H | H | 5-[2-(4-Chloro-3-methyl-phenylamino)-pyrimidin-4-yl]-3-ethyl-4-methyl-3H-thiazol-2-one |
| 52 | C | Et | NO₂ | H | H | H | 3-Ethyl-4-methyl-5-[2-(4-nitro-phenylamino)-pyrimidin-4-yl]-3H-thiazol-2-one |
| 53 | C | Et | SO₃H | H | H | H | 4-[4-(3-Ethyl-4-methyl-2-oxo-2,3-dihydro-thiazol-5-yl)-pyrimidin-2-ylamino]-benzenesulfonic acid |
| 54 | C | Et | H | SO₃H | H | H | 3-[4-(3-Ethyl-4-methyl-2-oxo-2,3-dihydro-thiazol-5-yl)-pyrimidin-2-ylamino]-benzenesulfonic acid |
| 55 | C | Me | H | CH₂NHSO₂Me | H | H | N-{3-[4-(3,4-Dimethyl-2-oxo-2,3-dihydro-thiazol-5-yl)-pyrimidin-2-ylamino]-benzyl}-methane-sulfonamide |

TABLE 1-continued

Exemplified compounds.
Structure

| No. | X | R¹ | R⁹ | R⁸ | R¹⁰ | R¹¹ | Name |
|---|---|---|---|---|---|---|---|
| 56 | C | Me | H | OMe | Me | H | 5-[2-(5-Methoxy-2-methyl-phenylamino)-pyrimidin-4-yl]-3,4-dimethyl-3H-thiazol-2-one |
| 57 | C | Me | H | CH₂NHCOPh | H | H | N-{3-[4-(3,4-Dimethyl-2-oxo-2,3-dihydro-thiazol-5-yl)-pyrimidin-2-ylamino]-benzyl}-benzamide |
| 58 | C | Me | H | CH₂NHSO₂CF₃ | H | H | N-{3-[4-(3,4-Dimethyl-2-oxo-2,3-dihydro-thiazol-5-yl)-pyrimidin-2-ylamino]-benzyl}-C,C,C-trifluoro-methanesulfonamide |
| 59 | C | Me | CH₂NHCOMe | H | H | H | N-{4-[4-(3,4-Dimethyl-2-oxo-2,3-dihydro-thiazol-5-yl)-pyrimidin-2-ylamino]-benzyl}-acetamide |
| 60 | C | Me | H | SO₂NH₂ | H | H | 3-[4-(3,4-Dimethyl-2-oxo-2,3-dihydro-thiazol-5-yl)-pyrimidin-2-ylamino]-benzenesulfonamide |
| 61 | C | Me | H | CONHiPr | Me | H | 3-[4-(3,4-Dimethyl-2-oxo-2,3-dihydro-thiazol-5-yl)-pyrimidin-2-ylamino]-N-isopropyl-4-methyl-benzamide |
| 62 | C | Me | H | SO₂NHEt | H | H | 3-[4-(3,4-Dimethyl-2-oxo-2,3-dihydro-thiazol-5-yl)-pyrimidin-2-ylamino]-N-ethyl-benzenesulfonamide |
| 63 | C | Me | H | CH₂OH | Me | H | 5-[2-(5-Hydroxymethyl-2-methyl-phenylamino)-pyrimidin-4-yl]-3,4-dimethyl-3H-thiazol-2-one |
| 64 | C | Me | H | CF₃ | H | NHCOMe | N-{3-[4-(3,4-Dimethyl-2-oxo-2,3-dihydro-thiazol-5-yl)-pyrimidin-2-ylamino]-5-trifluoromethyl-phenyl}-acetamide |
| 65 | C | Me | SO₂NH(CH₂)₂OMe | H | H | H | 4-[4-(3,4-Dimethyl-2-oxo-2,3-dihydro-thiazol-5-yl)-pyrimidin-2-ylamino]-N-(2-methoxy-ethyl)-benzenesulfonamide |
| 66 | C | Me | Cl | CF₃ | H | H | 5-[2-(4-Chloro-3-trifluoromethyl-phenylamino)-pyrimidin-4-yl]-3,4-dimethyl-3H-thiazol-2-one |
| 67 | C | Me | H | SO₂NH(CH₂)₂OMe | H | H | 3-{4-(3,4-Dimethyl-2-oxo-2,3-dihydro-thiazol-5-yl)-pyrimidin-2-ylamino]-N-(2-methoxy-ethyl)-benzenesulfonamide |

TABLE 1-continued

Exemplified compounds. Structure

| No. | X | R¹ | R⁹ | R⁸ | R¹⁰ | R¹¹ | Name |
|---|---|---|---|---|---|---|---|
| 68 | C | Me | H | CF₃ | H | Br | 5-[2-(3-Bromo-5-trifluoromethyl-phenylamino)-pyrimidin-4-yl]-3,4-dimethyl-3H-thiazol-2-one |
| 69 | C | Me | 4-Benzyl-piperazin-1-yl | H | H | H | 5-{2-[4-(4-Benzyl-piperazin-1-yl)-phenylamino]-pyrimidin-4-yl}-3,4-dimethyl-3H-thiazol-2-one |
| 70 | C | Me | CN | CF₃ | H | H | 4-[4-(3,4-Dimethyl-2-oxo-2,3-dihydro-thiazol-5-yl)-pyrimidin-2-ylamino]-2-trifluoromethyl-benzonitrile |
| 71 | C | Me | H | NH₂ | H | CF₃ | 5-[2-(3-Amino-5-trifluoromethyl-phenylamino)-pyrimidin-4-yl]-3,4-dimethyl-3H-thiazol-2-one |
| 72 | C | Me | SO₂NH(CH₂)₂OH | H | H | H | 4-[4-(3,4-Dimethyl-2-oxo-2,3-dihydro-thiazol-5-yl)-pyrimidin-2-ylamino]-N-(2-hydroxy-ethyl)-benzenesulfonamide |
| 73 | C | Me | SO₂NH-benzyl | H | H | H | N-Benzyl-4-[4-(3,4-dimethyl-2-oxo-2,3-dihydro-thiazol-5-yl)-pyrimidin-2-ylamino]-benzenesulfonamide |
| 74 | C | Me | H | SO₂NHiPr | H | H | 3-[4-(3,4-Dimethyl-2-oxo-2,3-dihydro-thiazol-5-yl)-pyrimidin-2-ylamino]-N-isopropyl-benzenesulfonamide |
| 75 | C | Me | H | SO₂NH(CH₂)₂OH | H | H | 3-[4-(3,4-Dimethyl-2-oxo-2,3-dihydro-thiazol-5-yl)-pyrimidin-2-ylamino]-N-(2-hydroxy-ethyl)-benzenesulfonamide |
| 76 | C | Me | H | NHMe | H | CF₃ | 3,4-Dimethyl-5-[2-(3-methylamino-5-trifluoromethyl-phenylamino)-pyrimidin-4-yl]-3H-thiazol-2-one |
| 77 | C | Me | H | SO₂NH-benzyl | H | H | N-Benzyl-3-[4-(3,4-dimethyl-2-oxo-2,3-dihydro-thiazol-5-yl)-pyrimidin-2-ylamino]-benzenesulfonamide |
| 78 | C | Me | Me | Morpholine-4-sulfonyl | H | H | 3,4-Dimethyl-5-{2-[4-methyl-3-(morpholine-4-sulfonyl)-phenylamino]-pyrimidin-4-yl}-3H-thiazol-2-one |

TABLE 1-continued

Exemplified compounds.
Structure

| No. | X | R¹ | R⁹ | R⁸ | R¹⁰ | R¹¹ | Name |
|---|---|---|---|---|---|---|---|
| 79 | C | Me | H | Morpholine-4- | H | H | 3,4-Dimethyl-5-{2-[3-(morpholine-4-sulfonyl)-phenylamino]-pyrimidin-4-yl}-3H-thiazol-2 -one |
| 80 | C | Me | $CH_2NH_2$ | H | H | H | 5-[2-(4-Aminomethyl-phenylamino)-pyrimidin-4-yl]-3,4-dimethyl-3H-thiazol-2-one |
| 81 | N | Me | Cl | — | H | Me | 5-[2-(6-Chloro-5-methyl-pyridin-3-ylamino)-pyrimidin-4-yl]-3,4-dimethyl-3H-thiazol-2-one |
| 82 | C | Me | $CH_2NHCO-$(pyrid-2-yl) | H | H | H | Pyridine-2-carboxylic acid 4-[4-(3,4-dimethyl-2-oxo-2,3-dihydro-thiazol-5-yl)-pyrimidin-2-ylamino]-benzylamide |
| 83 | | | | | | | 3,4-Dimethyl-5-{2-[(pyridin-3-ylmethyl)-amino]-pyrimidin-4-yl}-3H-thiazol-2-one |
| 84 | | | | | | | 5-(2-Amino-pyrimidin-4-yl)-3,4-dimethyl-3H-thiazol-2-one |

TABLE 1-continued

Exemplified compounds.
Structure

| No. | X | R¹ | R⁹ | R⁸ | R¹⁰ | R¹¹ | Name |
|---|---|---|---|---|---|---|---|
| 85 | | | | | | | N-[4-(3,4-Dimethyl-2-oxo-2,3-dihydro-thiazol-5-yl)-pyrimidin-2-yl]-acetamide |

TABLE 2

Analytical data for example compounds (refer Table 1)

| No. | $^1$H-NMR(d$_6$-DMSO; 500 MHz) δ; coupling constants J in Hz | Structure Composition | FW | MS [M + H]$^+$ m/z | RP-HPLC $t_R$ (min) |
|---|---|---|---|---|---|
| 1 | 2.56(3H, s, CH$_3$), 7.06(1H, d, ArH, J=5.4), 7.57(1H, dd, ArH, J=8.3, 8.3), 7.80(1H, d, ArH, J=8.3), 8.04(1H, d, ArH, J=8.3), 8.51(1H, d, ArH, J=5.4), 8.86(1H, s, ArH), 10.14(1H, s, NH) | C$_{15}$H$_{13}$N$_5$O$_3$S | 343.4 | 344 | 20.2$^a$ |
| 2 | 2.54(3H, s, CH$_3$), 3.28(3H, s, CH$_3$), 6.93(1H, d, J=5.5, pyrim-H), 7.12(2H, dd, J=8.8, 2×ArH), 7.72(2H, dd, J=8.8, 5.0, 2×ArH), 8.41(1H, d, J=5.5, pyrim-H) and 9.62(1H, s, NH) | C$_{15}$H$_{13}$FN$_4$OS | 316.4 | 317 | 13.7$^b$ |
| 3 | | C$_{15}$H$_{14}$N$_4$O$_2$S | 314.4 | | |
| 4 | 2.48(3H, s, CH$_3$), 3.29(3H, s, CH$_3$), 6.97(1H, d, J=5.0, pyrim-H), 7.33(2H, d, J=8.8, 2×ArH), 7.76(2H, d, J=8.8, 2×ArH), 8.44(1H, d, J=5.0, pyrim-H) and 9.75(1H, s, NH) | C$_{15}$H$_{13}$ClN$_4$OS | 332.8 | 332 | 22.3$^a$ |
| 5 | | C$_{15}$H$_{13}$BrN$_4$OS | 377.3 | | |
| 6 | 2.48(3H, s, CH$_3$), 3.28(3H, s, CH$_3$), 3.71(3H, s, OMe), 6.85–6.89(3H, m, pyrim-H and 2×ArH), 7.60(1H, d, J=9.0, ArH), 8.37(1H, d, J=5.0, pyrim-H) and 9.39(1H, s, NH) | C$_{16}$H$_{16}$N$_4$O$_2$S | 328.4 | 329 | 18.8$^a$ |
| 7 | 2.53(3H, s, CH$_3$), 3.27(3H, s, CH$_3$), 6.37(1H, dd J=7.5, 2.5, ArH), 6.90(1H, d, J=5.5, pyrim-H), 7.03(1H, dd, J=7.5, 7.5, ArH), 7.16(1H, d, J=7.5, ArH), 7.22(1H, s, ArH), 8.40(1H, d, J=5.5, pyrim-H), 9.22(1H, br s, OH) and 9.45(1H, s, NH) | C$_{15}$H$_{14}$N$_4$O$_2$S | 314.4 | 315 | 15.4$^a$ |
| 8 | 2.49(3H, s, CH$_3$), 2.82(6H, s, 2×NCH$_3$), 3.23(3H, s, CH$_3$), 6.81(1H, d, J=5.0, pyrim-H), 7.03(2H, d, J=8.0, 2×ArH), 7.50(2H, d, J=8.0, 2×ArH), 8.33(1H, d, J=5.0, pyrim-H) and 9.22(1H, s NH) | C$_{17}$H$_{19}$N$_5$OS | 341.4 | 342 | 19.7$^a$ |

TABLE 2-continued

Analytical data for example compounds (refer Table 1)

| No. | $^1$H-NMR(d$_6$-DMSO; 500 MHz) δ; coupling constants J in Hz | Structure Composition | FW | MS [M + H]$^+$ m/z | RP-HPLC t$_R$ (min) |
|---|---|---|---|---|---|
| 9 | 2.48(3H, s, CH$_3$), 3.03(4H, m, 2×morph-NCH$_2$), 3.08(3H, s, CH$_3$), 3.72(4H, m, 2×morph-OCH$_2$), 6.85(1H, d, J=5.2, pyrim-H), 6.89(2H, d, J=9.2, 2×ArH), 7.57(2H, d, J=9.2, 2×ArH), 8.36(1H, d, J=5.2, pyrim-H) and 9.35(1H, s, NH) | C$_{19}$H$_{21}$N$_5$O$_2$S | 383.5 | 384 | 17.5$^a$ |
| 10 | 2.28(3H, s, CH$_3$), 3.24(3H, s, CH$_3$), 6.99(1H, d, J=5.0, pyrim-H), 7.35(1H, d, J=9.0, ArH), 7.83(1H, dd, J=9.0, 2.0, ArH), 8.42(1H, d, J=2.0, ArH), 8.44(1H, d, J=9.0, ArH) and 9.84(1H, s, NH) | C$_{15}$H$_{12}$FN$_5$O$_3$S | 361.4 | 362 | 15.0$^b$ |
| 11 | 2.44(3H, s, CH$_3$), 2.55(3H, s, CH$_3$), 3.28(3H, s, CH$_3$), 7.03(1H, d, J=5.5, pyrim-H), 7.40(1H, d, J=9.0, ArH), 7.84(1H, d, J=9.0, ArH), 8.48(1H, d, J=5.5, pyrim-H), 8.59(1H, s, ArH) and 9.99(1H, s, NH) | C$_{16}$H$_{15}$N$_5$O$_3$S | 357.4 | 358 | 17.6$^b$ |
| 12 | 2.21(3H, s, CH$_3$), 2.54(3H, s, CH$_3$), 3.26(3H, s, CH$_3$), 6.92(1H, d, J=5.4, pyrim-H), 7.05(1H, dd, J=9.0, 9.0, ArH), 7.47(1H, m, ArH), 7.67(1H, ddd, J=6.5, 2.0, 0.5, ArH), 8.40(1H, d, J=5.4, pyrim-H) and 9.54(1H, s, NH) | C$_{16}$H$_{15}$FN$_4$OS | 330.4 | 331 | 16.3$^b$ |
| 13 | | C$_{20}$H$_{24}$N$_6$OS | 396.5 | | |
| 14 | 2.25(3H, s, CH$_3$), 2.37(3H, s, CH$_3$), 3.25(3H, s, CH$_3$), 6.97(1H, d, J=5.0, pyrim-H), 7.21(1H, d, J=8.5, ArH), 7.54(1H, dd, J=8.5, 2.0, ArH), 8.41(1H, d, J=2.0, ArH), 8.43(1H, d, J=5.0, pyrim-H) and 9.65(1H, s, NH) | C$_{16}$H$_{15}$IN$_4$OS | 438.3 | 439 | 19.8$^b$ |
| 15 | 2.30(3H, s, CH$_3$), 2.55(3H, s, CH$_3$), 3.27(3H, s, CH$_3$), 6.96(1H, d, J=5.1, pyrim-H), 7.29(1H, d, J=9.0, ArH), 7.53(1H, dd, J=9.0, 2.5, ArH), 7.81(1H, d, J=2.5, ArH), 8.43(1H, d, J=5.1, pyrim-H) and 9.69(1H, s, NH) | C$_{16}$H$_{15}$ClN$_4$OS | 346.8 | 347 | 18.7$^b$ |
| 16 | | C$_{16}$H$_{13}$N$_5$OS | 323.4 | | |
| 17 | 2.53(3H, s, CH$_3$), 2.98(2H, m, CH$_2$N(Ac)CH$_2$), 3.05(2H, m, CH$_2$N(Ac)CH$_2$), 3.14(3H, s, NCOCH$_3$), 3.56(4H, m, CH$_2$NCH$_2$), 6.85(1H, d, ArH, J=5.4), 6.90(2H, d, ArH, J=8.8), 7.56(2H, d, ArH, J=8.8), 8.35(1H, d, ArH, J=5.4), 9.36(1H, s, NH) | C$_{21}$H$_{24}$N$_6$O$_2$S | 424.5 | 425 | 10.1$^b$ |
| 18 | 2.56(3H, s, CH$_3$), 6.94(1H, d, ArH, J=5.4), 7.28(1H, d, ArH, J=8.5), 7.69(1H, dd, ArH, J=8.5, 2.5), 7.89(1H, d, ArH, J=2.5), 8.43(1H, d, ArH, J=5.4), 9.73(1H, s, NH) | C$_{16}$H$_{15}$ClN$_4$O$_2$S | 362.8 | 363 | 13.2$^b$ |
| 19 | 2.58(3H, s, CH$_3$), 7.04(1H, d, ArH, J=5.4), 7.28(1H, d, ArH, J=8.0), 7.51(1H, dd, ArH, J=8.0, 8.0), 7.87(1H, d, ArH, J=8.0), 8.34(1H, s, ArH), 8.48(1H, d, ArH, J=5.4), 9.89(1H, s, NH) | C$_{16}$H$_{13}$F$_3$N$_4$OS | 366.4 | 367 | 18.6$^b$ |
| 20 | 2.37(3H, s, CH$_3$), 3.28(3H, s, CH$_3$), 3.31 3H, s, N CH$_3$), 6.95(1H, d, ArH, J=5.4), 7.48(1H, d, ArH, J=8.5), 7.88(1H, d, ArH, J=8.5), 8.42(1H, d, ArH, J=5.4), 8.53(1H, s, ArH), 9.10(1H, s, NH) | C$_{16}$H$_{15}$N$_5$O$_3$S | 357.4 | 358 | 16.1$^b$ |
| 21 | 2.37(3H, s, CH$_3$), 2.56(3H, s, CH$_3$), 3.10(3H, s, N CH$_3$), 7.02(1H, d, ArH, J=5.4), 7.35(1H, d, ArH, J=8.9), 7.83(1H, d, ArH, J=8.9), 8.22(1H, s, ArH), 8.46(1H, d, ArH, J=5.4), 9.84(1H, s, NH) | C$_{17}$H$_{15}$F$_3$N$_4$OS | 380.4 | 381 | 19.4$^b$ |
| 22 | 2.55(3H, s, CH$_3$), 2.73(6H, s, N(CH$_3$)$_2$, 3.28(3H, s, CH$_3$), 6.98(1H, d, ArH, J=5.4), 7.25(1H, d, ArH, J=8.8), 7.75(1H, dd, ArH, J=8.8, 2.4), 8.36(1H, d, ArH, J=2.4), 8.43(1H, d, ArH, J=5.4), 9.75(1H, s, NH) | C$_{17}$H$_{18}$N$_6$O$_3$S | 386.4 | 387 | 16.3$^a$ |
| 23 | 1.18(3H, t, CH$_3$, J=7.3), 2.58(3H, s, CH$_3$), 3.82(, 2H, q, NHCH$_2$, J=7.3), 7.07(1H, d, ArH, J=5.4), 7.58(1H, dd, ArH, J=8.8, 8.8), 7.79(1H, d, ArH, J=8.8), 8.04(1H, d, ArH, J=8.8), 8.87(1H, s, ArH), 10.15(1H, s, NH) | C$_{16}$H$_{15}$N$_5$O$_3$S | 357.4 | 358 | 21.7$^a$ |

TABLE 2-continued

Analytical data for example compounds (refer Table 1)

| No. | $^1$H-NMR($d_6$-DMSO; 500 MHz) δ; coupling constants J in Hz | Structure Composition | FW | MS [M + H]$^+$ m/z | RP-HPLC $t_R$ (min) |
|---|---|---|---|---|---|
| 24 | 1.19(3H, t, CH$_3$, J=7.3), 2.58(3H, s, CH$_3$), 3.81(2H, q, NCH$_2$, J=7.3), 6.95(1H, d, ArH, J=5.4), 7.30(1H, d, ArH, J=8.8), 7.72(1H, dd, ArH, J=8.8, 2.9), 7.98(1H, s, CO$_2$H), 8.25(1H, d, ArH, J=2.9), 8.45(1H, d, ArH, J=5.4), 9.74(1H, s, NH) | C$_{17}$H$_{15}$ClN$_4$O$_3$S | 390.8 | 391 | 17.9$^a$ |
| 25 | 1.18(3H, t, CH$_3$, J=7.3), 2.57(3H, s, CH$_3$), 3.82(2H, q, NCH$_2$, J=7.3), 7.00(1H, d, ArH, J=5.4), 7.45(1H, d, ArH, J=8.8), 7.83(1H, dd, ArH, J=8.8, J=2.0), 8.27(1H, d, ArH, J=2.0), 8.51(1H, d, ArH, J=5.4), 9.90(1H, s, NH) | C$_{18}$H$_{17}$ClN$_4$O$_3$S | 404.9 | 391(M−CH$_3$) | 18.7$^a$ |
| 26 | 1.17(3H, t, CH$_3$, J=7.3), 2.55(3H, s, CH$_3$), 2.83(6H, s, N(CH$_3$)$_2$), 3.81(2H, q, NCH$_2$, J=7.3), 6.71(2H, d, ArH, J=8.8), 6.80(1H, d, ArH, J=5.4), 7.50(2H, d, ArH, J=8.8), 8.34(1H, d, ArH, J=5.4), 9.22(1H, s, NH) | C$_{18}$H$_{21}$N$_5$OS | 355.5 | 356 | 13.6$^a$ |
| 27 | 1.17(3H, t, CH$_3$, J=7.3), 2.56(3H, s, CH$_3$), 3.02(4H, m, CH$_2$NCH$_2$), 3.72(4H, m, CH$_2$OCH$_2$), 3.80(2H, q, NCH$_2$, J=7.3), 6.85(1H, d, ArH, J=5.4), 6.90(2H, d, ArH, J=8.3), 7.56(2H, d, ArH, J=8.3), 8.36(1H, d, ArH, J=5.4), 9.35(1H, s, NH) | C$_{20}$H$_{23}$N$_5$O$_2$S | 397.5 | 398 | 14.6$^a$ |
| 28 | 1.17(3H, t, CH$_3$, J=7.3), 2.57(3H, s, CH$_3$), 3.28(3H, s, CH$_3$), 3.81(2H, t, NCH$_2$, J=7.3), 7.03(1H, d, ArH, J=5.4), 7.40(1H, d, ArH, J=8.9), 7.82(1H, dd, ArH, J=8.9, 2.1), 8.48(1H, d, ArH, J=5.4), 8.60(1H, d, ArH, J=2.1), 10.00(1H, s, NH) | C$_{17}$H$_{17}$N$_5$O$_3$S | 371.4 | 372 | 18.8$^b$ |
| 29 | 1.19(3H, t, CH$_3$, J=7.3), 2.58(3H, s, CH$_3$), 2.76(6H, s, N(CH$_3$)$_2$), 3.84(2H, q, NCH$_2$, J=7.3), 6.98(1H, d, ArH, J=5.4), 7.25(1H, d, ArH, J=8.8), 7.76(1H, dd, ArH, J=8.8, 2.4), 8.37(1H, d, ArH, J=2.4), 8.45(1H, d, ArH, J=5.4), 9.76(1H, s, NH) | C$_{18}$H$_{20}$N$_6$O$_3$S | 400.5 | 401 | 17.5$^b$ |
| 30 | 0.95(6H, d, CH(CH$_3$)$_2$, J=7.3), 1.48(2H, m, CH$_2$CH), 1.61(1H, septet, CH(CH$_3$)$_2$), 2.57(3H, s, CH$_3$), 3.77(2H, m, NCH$_2$), 7.07(1H, d, ArH, J=5.4), 7.58(1H, dd, ArH, J=8.7, 8.7), 7.69(1H, d, ArH, J=8.7), 8.02(1H, d, ArH, J=8.7), 8.52(1H, d, ArH, J=5.4), 8.87(1H, d, ArH, J=8.7), 10.15(1H, s, NH) | C$_{19}$H$_{21}$N$_5$O$_3$S | 399.5 | | 17.1$^b$ |
| 31 | 0.93(6H, d, CH(CH$_3$)$_2$, J=7.3), 1.48(2H, m, CH$_2$CH), 1.60(1H, septet, CH(CH$_3$)$_2$), 2.57(3H, s, CH$_3$), 3.78(2H, m, NCH$_2$), 6.97(1H, d, ArH, J=5.4), 7.33(2H, d, ArH, J=8.8), 7.76(2H, d, ArH, J=8.8), 8.45(1H, d, ArH, J=5.4), 9.75(1H, s, NH) | C$_{19}$H$_{21}$ClN$_4$OS | 388.9 | 389 | 19.5$^b$ |
| 32 | | C$_{14}$H$_{12}$ClN$_5$OS | 333.8 | | |
| 33 | 1.15(t, 3H, J=6.8, CH$_3$), 2.55(s, 3H, CH$_3$), 3.26(m, 2H, CH$_2$), 3.80(s, 3H, OCH$_3$), 6.79(d, 1H, J=9.3, pyridyl-H), 6.91(d, 1H, J=5.4, pyrimidinyl-H), 7.97(dd, 1H, J=9.2, 2.9, pyridyl-H), 8.38(d, 1H, J=5.4, pyrimidinyl-H), 8.44(d, 1H, J=2.9, pyridyl-H), 9.50(s, 1H, NH) | C$_{16}$H$_{17}$N$_5$O$_2$S | 343.4 | 342 | 15.6$^a$ |
| 34 | 0.93(d, 6H, J=7.3, CH$_3$), 1.48(m, 2H, CH$_2$), 1.62(m, 1H, CH), 2.58(s, 3H, CH$_3$), 3.79(m, 2H, CH$_2$), 7.03(d, 1H, J=5.4, pyrimidinyl-H), 7.45(d, 1H, J=9.3, pyridyl-H), 8.21(dd, 1H, J=2.9, 9.3, pyridyl-H), 8.49(d, 1H, J=5.4, pyrimidinyl-H), 8.76(d, 1H, J=2.9, pyridyl-H), 9.95(s, 1H, NH) | C$_{18}$H$_{20}$ClN$_5$OS | 389.9 | 390 | 21.3$^b$ |
| 35 | 0.95(d, 6H, J=7.3, CH$_3$), 1.48(m, 2H, CH$_2$), 1.61(m, 1H, CH), 2.57(s, 3H, CH$_3$), 3.77(m, 2H, CH$_2$), 3.82(s, 3H, OCH$_3$), 6.77(d, 1H, J=9.2, pyridyl-H), 6.90(d, 1H, J=5.4Hz, pyrimidinyl-H), 7.98(dd, 1H, J=2.9, 9.2, pyridyl-H), 8.38(d, 1H, J=5.4, pyrimidinyl-H), 8.44(d, 1H, J=2.9, pyridyl-H), 9.51(s, 1H, NH) | C$_{19}$H$_{23}$N$_5$O$_2$S | 385.5 | 387 | 20.5$^b$ |
| 36 | | C$_{15}$H$_{13}$IN$_4$OS | 424.3 | | |
| 37 | | C$_{17}$H$_{18}$N$_6$O$_3$S | 386.4 | | |
| 38 | | C$_{19}$H$_{22}$N$_6$OS | 382.5 | | |
| 39 | | C$_{16}$H$_{17}$N$_5$OS | 327.4 | | |

TABLE 2-continued

Analytical data for example compounds (refer Table 1)

| No. | $^1$H-NMR($d_6$-DMSO; 500 MHz) δ; coupling constants J in Hz | Structure Composition | FW | MS [M + H]$^+$ m/z | RP-HPLC $t_R$ (min) |
|---|---|---|---|---|---|
| 40 | 2.53(3H, s, CH$_3$), 7.00(1H, d, ArH, J=5.5), 7.56(1H, dd, ArH, J=8.0, 8.0), 7.79(1H, d, ArH, J=8.0), 8.02(1H, d, ArH, J=8.0), 8.49(1H, d, ArH, 5.5), 8.87(1H, s, ArH, | C$_{14}$H$_{11}$N$_5$O$_3$S | 329.3 | 330 | 14.8$^b$ |
| 41 | 2.41(3H, s, CH$_3$), 2.54(3H, s, CH$_3$), 6.97(1H, d, ArH, J=5.5), 7.40(1H, d, ArH, J=9.0), 7.82(1H, d, ArH, J=9.0), 8.46(1H, d, ArH, J=5.5), 8.59(1H, s, ArH), 9.98(1H, s, NH), 11.73(1H, s, NH) | C$_{15}$H$_{13}$N$_5$O$_3$S | 343.4 | 343 | 15.5$^b$ |
| 42 | 2.28(s, 3H, CH$_3$), 2.97(s, 3H, CH$_3$), 3.70(s, 3H, CH$_3$), 4.63(d, 2H, J=6.0, CH$_2$), 7.26(d, 1H, J=7.5, Ph-H), 7.34(d, 1H, J=5.0, pyrimidinyl-H), 7.64(t, 1H, J=8.0, Ph-H), 8.02(d, 1H, J=8.0, Ph-H), 8.05(s, 1H, Ph-H), 8.71(s, 1H, NH), 8.83(d, 1H, J=5.0, pyrimidinyl-H | C$_{18}$H$_{19}$N$_5$O$_2$S | 369.4 | 370 | 13.0$^a$ |
| 43 | 1.18(t, 3H, J=7.3, CH$_3$), 2.53(s, 3H, CH$_3$), 3.82(q, 2H, J=7.3, CH$_2$), 6.37(dd, 1H, J=7.3, 1.5, Ph-H), 6.93(d, 1H, J=5.4, pyrmidinyl-H), 7.05(dd, 1H, J=7.3, Ph-H), 7.17(d, 1H, J=7.3, 1.5, Ph-H), 7.24(d, 1H, J=1.5, Ph-H,), 8.42(d, 1H, J=5.4, Ph-H), 9.47(s, 1H, NH) | C$_{16}$H$_{16}$N$_4$O$_2$S | 328.4 | 329 | 15.2$^a$ |
| 44 | 2.62(s, 3H, CH$_3$), 3.), 3.01(m, 4H, CH$_2$), 3.08(m, 4H, CH$_2$), 3.37(s, 3H, CH$_3$), 6.70(d, 1H, J=5.4, pyrimidinyl-H), 7.00(brs, 1H, NH), 7.04(d, 1H, J=8.8, Ph-H), 7.34(dd, 1H, J=2.5, 8.8, Ph-H), 7.83(d, 1H, J=2.9, Ph-H), 8.34(d, 1H, J=5.4, pyrimidinyl-H | C$_{19}$H$_{21}$ClN$_6$OS | 416.9 | 417 | N/D$^c$ |
| 45 | 1.18(t, 3H, J=7.4, CH$_3$), 2.57(s, 3H, CH$_3$), 3.81(q, 2H, J=7.4, CH$_2$), 6.93(d, 1H, J=5.4, pyrimidinyl-H), 7.13(d, 2H, J=8.8, Ph-H), 7.72(d, 2H, J=8.8, Ph-H), 8.42(d, 1H, J=5.4, pyrimidinyl-H), 9.62(s, 1H, NH) | C$_{16}$H$_{15}$FN$_4$OS | 330.4 | 331.36 | 18.9$^a$ |
| 46 | 1.17(t, 3H, J=7.4, CH$_3$), 2.58(s, 3H, CH$_3$), 3.83(q, 2H, J=7.4, CH$_2$), 6.97(d, 1H, J=5.4, pyrimidinyl-H), 7.34(d, 2H, J=8.7, Ph-H), 7.77(d, 2H, J=8.7, Ph-H), 8.45(d, 1H, J=5.4, pyrimidin-H), 9.75(s, 1H, NH) | C$_{16}$H$_{15}$ClN$_4$OS | 346.8 | 347 | 22.0$^a$ |
| 47 | 1.18(t, 3H, J=7.4, CH$_3$), 2.05(s, 3H, CH$_3$), 2.58(s, 3H, CH$_3$), 3.80(q, 2H, J=7.4, CH$_2$), 6.85(d, 1H, J=5.4, pyrimidin-H), 6.92(d, 1H, J=8.3, Ph-H), 7.08(dd, 1H, J=8.3, 2.0, Ph-H), 7.17(d, 1H, J=2.0, Ph-H), 8.39(d, 1H, J=5.4, pyrmidin-H), 9.36(s, 1H, NH) | C$_{17}$H$_{18}$N$_4$O$_2$S | 342.4 | 343 | 16.4$^a$ |
| 48 | 1.18(t, 3H, J=7.4, CH$_3$,), 2.57(s, 3H, CH$_3$), 3.83(q, 2H, J=7.4, CH$_2$), 7.06(d, 1H, J=5.4, pyrimidinyl-H), 7.62(d, 1H, J=8.8, Ph-H), 7.94(dd, 1H, J=8.8, 2.9, Ph-H), 8.41(d, 1H, J=2.9, Ph-H), 8.50(d, 1H, J=5.4, pyrimidinyl-H,), 10.08(s, 1H, NH) | C$_{17}$H$_{14}$ClF$_3$N$_4$OS | 414.8 | 415 | 16.0$^b$ |
| 49 | 2.04(s, 3H, CH$_3$), 2.56(s, 3H, CH$_3$), 3.08(m, 2H, CH$_2$), 3.15(m, 2H, CH$_2$), 3.29(s, 3H, CH$_3$), 3.57(d, 4H, CH$_2$), 6.57(m, 1H, Ph-H), 6.94(d, 1H, J=5.5, pyrimidinyl-H), 7.13(t, 1H, J=8.0, Ph-H), 7.45(m, 1H, Ph-H), 8.42(d, 1H, J=5.5, pyrimidinyl-H), 9.45(s, 1H, NH) | C$_{21}$H$_{24}$N$_6$O$_2$S | 424.5 | 447.4[M+Na]$^+$ | 11.6$^b$ |
| 50 | 1.18(t, 3H, J=7.4, CH$_3$), 2.57(s, 3H, CH$_3$), 3.84(q, 2H, J=7.4, CH$_2$), 4.10(s, 3H, OCH$_3$), 6.54(dd, 1H, J=8.8, 2.0, Ph-H), 6.97(d, 1H, J=5.4, pyrimidinyl-H), 7.17(d, 1H, J=8.8Hz, Ph-H), 7.29(dd, 1H, J=8.8, 2.0, Ph-H), 7.47(d, 1H, J=2.0, Ph-H), 8.44(d, 1H, J=5.4, pyriminyl-H), 9.58(s, 1H, NH) | C$_{17}$H$_{18}$N$_4$O$_2$S | 342.4 | 343 | 18.7$^a$ |
| 51 | 1.17(t, 3H, J=7.4, CH$_3$), 2.04(s, 3H, CH$_3$), 2.58(s, 3H, CH$_3$), 3.82(q, 2H, J=7.4, CH$_2$), 6.96(d, 1H, J=5.4, pyrimidinyl-H), 7.29(d, 1H, J=8.8, Ph-H), 7.53(dd, 1H, J=8.8, 2.4, Ph-H), 7.81(d, 1H, J=2.4, Ph-H), 8.44(d, 1H, J=5.4, pyrimidinyl-H), 9.67(s, 1H, NH) | C$_{17}$H$_{17}$ClN$_4$OS | 360.9 | 361 | 23.3$^a$ |

TABLE 2-continued

Analytical data for example compounds (refer Table 1)

| No. | $^1$H-NMR($d_6$-DMSO; 500 MHz) δ; coupling constants J in Hz | Structure Composition | FW | MS [M + H]$^+$ m/z | RP-HPLC $t_R$ (min) |
|---|---|---|---|---|---|
| 52 | 1.18(t, 3H, J=7.4, CH$_3$), 2.58(s, 3H, CH$_3$), 3.82(q, 2H, J=7.4, CH$_2$), 7.00(d, 1H, J=5.4, pyrimidinyl-H), 7.24(d, 2H, J=8.8, Ph-H), 7.81(d, 2H, J=8.8, Ph-H), 8.46(d, 1H, J=5.4, Ph-H), 9.79(s, 1H, NH) | C$_{16}$H$_{15}$N$_5$O$_3$S | 357.4 | 359 | 13.0$^b$ |
| 53 | 1.19(t, 3H, J=7.4, CH$_3$), 2.59(s, 3H, CH$_3$), 3.82(q, 2H, J=7.4, CH$_2$), 6.93(d, 1H, J=5.4, pyrimidinyl-H), 7.50(d, 2H, J=8.8, Ph-H), 7.66(d, 2H, J=8.8, Ph-H), 8.44(d, 1H, J=5.4, Ph-H), 9.67(s, 1H, NH) | C$_{16}$H$_{16}$N$_4$O$_4$S$_2$ | 392.5 | 391 | 11.4$^a$ |
| 54 | 1.19(t, 3H, J=7.4, CH$_3$), 2.61(s, 3H, CH$_3$), 3.81(q, 2H, J=7.4, CH$_2$), 6.90(d, 1H, J=5.4, pyrimidinyl-H), 7.19(dd, 1H, J=8.8, 1.9, Ph-H), 7.21(dd, 1H, J=8.8, 1.9, Ph-H), 7.71(dd, 1H, J=8.8, 1.9, Ph-H), 7.96(d, 1H, J=1.9, Ph-H), 9.65(s, 1H, NH) | C$_{16}$H$_{16}$N$_4$O$_4$S$_2$ | 392.5 | 391 | 11.4$^a$ |
| 55 | 2.64(s, 3H, CH$_3$), 2.91(s, 3H, CH$_3$), 3.39(s, 3H, CH$_3$), 4.28(s, 2H, CH$_2$), 6.93(d, 1H, J=5.5, pyrimidinyl-H), 7.06(d, 1H, J=8.0, Ph-H), 7.33(t, 1H, J=8.0, Ph-H), 7.64(d, 1H, J=8.0, Ph-H), 7.79(s, 1H Ph-H), 8.41(d, 1H, J=5.5, pyrimidinyl-H), 9.45(s, 1H, NH) | C$_{17}$H$_{19}$N$_5$O$_3$S$_2$ | 405.5 | 406 | 14.0$^a$ |
| 56 | 2.14(s, 3H, CH$_3$), 2.49(s, 3H, CH$_3$), 3.72(s, 3H, OCH$_3$), 6.64(dd, 1H, J=8.3, 2.4, Ph-H), 6.83(d, 1H, J=5.4, pyrimidinyl-H), 7.10(d, 1H, J=8.4, Ph-H), 7.12(d, 1H, J=2.4, Ph-H), 8.35(d, 1H, J=5.4, pyrimidinyl-H), 8.72(s, 1H, NH) | C$_{17}$H$_{18}$N$_4$O$_2$S | 342.4 | 343 | 16.9$^a$ |
| 57 | 2.54(s, 3H, CH$_3$), 3.28(s, 3H, CH$_3$), 4.47(d, 2H, J=6.0, CH$_2$), 6.93(m, 2H, Ph-H & pyrimidinyl-H), 7.25(m, 1H, Ph-H), 7.47(m, 2H, Ph-H), 7.52(m, 1H, Ph-H), 7.65(d, 1H, J=8.0, Ph-H), 7.71(s, 1H Ph-H), 7.91(m, 3H, Ph-H), 8.40(d, 1H, J=5.0, pyrimidinyl-H), 9.02(m, 1H, NH), 9.62(s, 1H, NH) | C$_{23}$H$_{21}$N$_5$O$_2$S | 431.5 | 432 | 13.5$^b$ |
| 58 | 2.58(s, 3H, CH$_3$), 3.31(s, 3H, CH$_3$), 4.33(s, 2H, CH$_2$), 6.96(m, 2H, Ph-H & pyrimidinyl-H), 7.32(t, 1H, J=8.0, Ph-H), 7.72(d, 1H, J=8.0, Ph-H), 7.74(s, 1H, Ph-H), 8.44(d, 1H, J=5.0, pyrimidinyl-H) | C$_{17}$H$_{16}$F$_3$N$_5$O$_3$S$_2$ | 459.5 | 460 | 18.9$^a$ |
| 59 | 2.29(s, 3H, CH$_3$), 2.99(s, 3H, CH$_3$), 3.73(s, 3H, CH$_3$), 4.62(d, 2H, J=6.0, CH$_2$), 7.36(d, 1H, J=5.5, pyrimidinyl-H), 7.61(d, 2H, J=8.5, Ph-H), 8.11(d, 2H, J=7.0, Ph-H), 8.68(m, 1H, NH), 8.85(d, 1H, J=5.5, pyrimidinyl-H) | C$_{18}$H$_{19}$N$_5$O$_2$S | 369.4 | 370. | 12.6$^a$ |
| 60 | 2.66(s, 3H, CH$_3$), 3.38(s, 3H, CH$_3$), 7.07(d, 1H, J=5.5, pyrimidinyl-H), 7.38(s, 2H, NH$_2$), 7.50(d, 1H, J=8.5, Ph-H), 7.56(t, 1H, J=8.0, Ph-H), 8.02(d, 1H, J=8.0, Ph-H), 8.35(s, 1H, Ph-H), 8.55(d, 1H, J=5.5, pyrimidinyl-H) | C$_{15}$H$_{15}$N$_5$O$_3$S$_2$ | 377.4 | 376 | 13.7$^a$ |
| 61 | 1.14(d, 6H, J=7.3Hz, CH$_3$), 2.50(s, 3H, CH$_3$), 2.48(s, 3H, CH$_3$), 3.74(s, 3H, OCH$_3$), 4.02(septet, 1H, J=7.3, CH), 6.80(d, 1H, J=5.4, pyrimidinyl-H), 7.27(1H, d, J=8.3, Ph-H), 7.55(dd, 1H, J=8.3, 2.0, Ph-H), 7.93(d, 1H, J=2.0, Ph-H), 8.08(s, 1H, NH), 8.33(d, 1H, J=5.4, pyrimidinyl-H), 8.93(s, 1H, NH) | C$_{20}$H$_{23}$N$_5$O$_2$S | 397.5 | 398 | 15.5$^a$ |
| 62 | 0.98(t, 3H, J=7.0, CH$_3$), 2.53(s, 3H, CH$_3$), 2.82(m, 2H, CH$_2$), 3.27(s, 3H, CH$_3$), 7.00(d, 1H, J=5.0, pyrimidinyl-H), 7.35(m, 1H, Ph-H), 7.48(m, 1H, Ph-H), 7.95(m, 1H, Ph-H), 8.26(s, 1H, Ph-H), 8.47(d, 1H, J=5.5, pyrimidinyl-H), 9.93(s, 1H, NH) | C$_{17}$H$_{19}$N$_5$O$_3$S$_2$ | 405.5 | 406 | 13.4$^b$ |
| 63 | 2.27(s, 3H, CH$_3$), 2.59(s, 3H, CH$_3$), 3.26(s, 3H, CH$_3$), 4.46(s, 2H, CH$_2$), 5.17(s, 1H, OH), 5.50(d, 1H, J=5.4, pyrimidinyl-H), 6.95(d, 1H, J=8.2, Ph-H), 7.20(d, 1H, J=5.4, pyrimidinyl-H), 7.34(s, 1H, Ph-H), 7.88(d, 1H, J=8.2, Ph-H), 11.95(s, 1H, NH) | C$_{17}$H$_{18}$N$_4$O$_2$S | 342.4 | 342 | 15.2$^a$ |

TABLE 2-continued

Analytical data for example compounds (refer Table 1)

| No. | $^1$H-NMR(d$_6$-DMSO; 500 MHz) δ; coupling constants J in Hz | Structure Composition | FW | MS [M + H]$^+$ m/z | RP-HPLC t$_R$ (min) |
|---|---|---|---|---|---|
| 64 | 2.07(s, 3H, CH$_3$), 2.57(s, 3H, CH$_3$), 3.31(s, 3H, CH$_3$), 7.01(d, 1H, J=5.4, pyrimidinyl-H), 7.65(s, 1H, Ph-H), 7.83(s, 1H, Ph-H), 7.94(s, 1H, Ph-H), 8.35(d, 1H, J=5.4, pyrimidinyl-H), 9.85(s, 1H, NH) | C$_{18}$H$_{16}$F$_3$N$_5$O$_2$S | 423.4 | 424 | 16.0[a] |
| 65 | 2.52(s, 3H, CH$_3$), 2.82(q, 2H, J=6, 12, CH$_2$), 3.10(s, 3H, CH$_3$), 3.23(m, 2H, CH$_2$), 7.00(d, 1H, J=5.5, pyrimidinyl-H), 7.43(t, 1H, J=6.0, Ph-H), 7.64(d, 2H, J=9.0, Ph-H), 7.87(d, 2H, J=9.0, Ph-H), 8.44(d, 1H, J=5.5, pyrimidinyl-H) | C$_{18}$H$_{21}$N$_5$O$_4$S$_2$ | 435.5 | 436 | 16.3[a] |
| 66 | 2.51(s, 3H, CH$_3$), 3.26(s, 3H, CH$_3$), 6.96(d, 1H, J=5.4, pyrimidinyl-H), 7.51(d, 1H, J=9.3, Ph-H), 7.83(dd, 1H, J=9.3, 2.5, Ph-H), 8.28(d, 1H, J=2.5, Ph-H), 8.37(d, 1H, J=5.4, pyrimidinyl-H), 9.93(s, 1H, NH) | C$_{16}$H$_{12}$ClF$_3$N$_4$OS | 400.8 | 401 | 16.3[a] |
| 67 | 2.47(2H, t, CH$_2$N, J=5.9), 2.54(3H, s, CH$_3$), 2.88(2H, t, CH$_2$O, J=5.9), 3.11(3H, s, OCH$_3$), 3.24(3H, s, CH$_3$), 6.89(1H, d, ArH, J=5.4), 7.23(1H, d, ArH, J=7.3), 7.37(1H, dd, ArH, J=7.8, 7.8), 7.55(1H, s, NH), 7.81(1H, d, ArH, J=7.8), 8.10(1H, s, ArH), 8.34(1H, d, ArH, J=5.4), 9.76(1H, s, NH) | C$_{18}$H$_{21}$N$_5$O$_4$S$_2$ | 435.5 | 436 | 15.8[a] |
| 68 | 2.53(s, 3H, CH$_3$), 3.24(s, 3H, CH$_3$), 7.10(d, 1H, J=5.4, pyrimidinyl-H), 7.47(s, 1H, Ph-H), 8.21(s, 1H, Ph-H), 8.38(s, 1H, Ph-H), 8.53(1H, d, J=5.4, pyrimidinyl-H), 10.17(s, 1H, NH) | C$_{16}$H$_{12}$BrF$_3$N$_4$OS | 445.3 | 446 | 23.4[a] |
| 69 | 2.54(s, 3H, CH$_3$), 3.07(m, 4H, CH$_2$), 3.22(s, 3H, CH$_3$), 3.30(m, 4H, CH$_2$), 6.87(m, 3H, Ph-H and pyrimidinyl-H), 7.26(m, 1H, NH), 7.55(d, 2H, J=8.0, Ph-H), 8.37(d, 1H, J=5.5, pyrimidinyl-H), 9.33(s, 1H, NH) | C$_{26}$H$_{28}$N$_6$OS | 472.6 | 473 | 11.2[b] |
| 70 | 2.57(s, 3H, CH$_3$), 3.29(s, 3H, CH$_3$), 7.18(d, 1H, J=5.4, pyrimidinyl-H), 8.05(d, 1H, J=8.8, Ph-H), 8.10(dd, 1H, J=8.8, 2.0, Ph-H), 8.54(d, 1H, J=2.0, Ph-H), 8.58(d, 1H, J=5.4, pyrimidinyl-H), 10.55(s, 1H, NH) | C$_{17}$H$_{12}$F$_3$N$_5$OS | 391.4 | 390 | 22.3[a] |
| 71 | 2.57(s, 3H, CH$_3$), 3.29(s, 3H, CH$_3$), 5.47(s, 2H, NH$_2$), 6.48(s, 1H, Ph-H), 6.95(d, 1H, J=5.4, pyrimidinyl-H), 7.06(s, 1H, Ph-H), 7.44(s, 1H, Ph-H), 8.44(d, 1H, J=5.4, pyrimidinyl-H), 9.65(s, 1H, NH) | C$_{16}$H$_{14}$F$_3$N$_6$OS | 381.4 | 382 | 16.3[a] |
| 72 | 2.52(s, 3H, CH$_3$), 2.71(q, 2H, J=6.5, 12.5, CH$_2$), 3.25(s, 3H, CH$_3$), 4.61(t, 2H, J=5.5, CH$_2$), 7.00(d, 1H, J=5.5, pyrimidinyl-H), 7.31(t, 1H, J=6.0, Ph-H), 7.65(d, 2H, J=8.5, Ph-H), 7.87(d, 2H, J=9.0, Ph-H), 8.44(d, 1H, J=5.5, pyrimidinyl-H) | C$_{17}$H$_{19}$N$_5$O$_4$S$_2$ | 421.5 | | 13.9[a] |
| 73 | 2.51(s, 3H, CH$_3$), 3.24(s, 3H, CH$_3$), 3.89(d, 2H, J=6.0, CH$_2$), 7.00(d, 1H, J=5.0, pyrimidinyl-H), 7.14–7.30(m, 5H, Ph-H), 7.65(d, 2H, J=9.0, Ph-H), 7.86(d, 2H, J=9.0, Ph-H), 8.44(d, 1H, J=5.0, pyrimidinyl-H) | C$_{22}$H$_{21}$N$_5$O$_3$S$_2$ | 467.6 | 468 | 20.1[a] |
| 74 | 0.96(s, 3H, CH$_3$), 0.97(S, 3H, CH$_3$), 2.57(s, 3H, CH$_3$), 3.29(s, 3H, CH$_3$), 7.00(d, 1H, J=5.0, pyrimidinyl-H), 7.37(m, 1H, Ph-H), 7.50(t, 1H, J=7.5, Ph-H), 7.93(m, 1H, Ph-H), 8.28(s, 1H, Ph-H), 8.47(d, 1H, J=5.5, pyrimidinyl-H), 9.93(s, 1H, NH) | C$_{18}$H$_{21}$N$_5$O$_3$S$_2$ | 419.5 | 420 | 15.1[b] |
| 75 | 2.64(s, 3H, CH$_3$), 2.89(q, 2H, J=12.2, CH$_2$), 3.36(s, 3H, CH$_3$), 3.43(m, 2H, CH$_2$), 7.07(d, 1H, J=5.5, pyrimidinyl-H), 7.43(m, 1H, Ph-H), 7.56(m, 1H, Ph-H), 8.03(m, 1H, Ph-H), 8.31(t, 1H, J=1.5, Ph-H), 8.54(d, 1H, J=5.5, pyrimidinyl-H) | C$_{17}$H$_{19}$N$_5$O$_4$S$_2$ | 421.5 | 422 | 13.6[a] |
| 76 | 2.53(s, 3H, CH$_3$), 2.76(d, 3H, J=4.9, CH$_3$), 3.29(s, 3H, CH$_3$), 5.32(d, 1H, J=4.9, CH$_3$), 6.72(d, 1H, J=8.8, Ph-H), 6.86(d, 1H, J=5.4, pyrimidinyl-H), 7.66(dd, 1H, J=8.8, 2.4, Ph-H), 7.89(d, 1H, J=2.4, Ph-H), 8.36(d, 1H, J=5.4, pyrimidinyl-H), 9.40(s, 1H, NH) | C$_{17}$H$_{16}$F$_3$N$_5$OS | 395.4 | 397 | 18.3[a] |

TABLE 2-continued

Analytical data for example compounds (refer Table 1)

| No. | $^1$H-NMR($d_6$-DMSO; 500 MHz) δ; coupling constants J in Hz | Structure Composition | FW | MS [M + H]$^+$ m/z | RP-HPLC $t_R$ (min) |
|---|---|---|---|---|---|
| 77 | 2.64(s, 3H, CH$_3$), 3.36(s, 3H, CH$_3$), 4.08(s, 2H, CH$_2$), 7.07(d, 1H, J=5.0, pyrmidinyl-H), 7.28–7.35(m, 5H, Ph-H), 7.45(d, 1H, J=8.0, Ph-H), 7.56(t, 1H, J=8.0, Ph-H), 8.03(d, 1H, J=8.5, Ph-H), 8.15(s, 1H, NH), 8.36(s, 1H, Ph-H), 8.55(d, 1H, J=5.5, pyrimidinyl-H) | C$_{22}$H$_{21}$N$_5$O$_3$S$_2$ | 467.6 | | 19.4$^a$ |
| 78 | 2.69(s, 3H, CH$_3$), 3.19(m, 4H, CH$_2$), 3.43(s, 3H, CH$_3$), 3.76(m, 4H, CH$_2$), 7.12(d, 1H, J=5.5, pyrmidinyl-H), 7.52(d, 1H, J=8.5, Ph-H), 8.12(d, 1H, J=8.5, Ph-H), 8.31(s, 1H, Ph-H), 8.59(d, 1H, J=5.0, pyrimidinyl-H) | C$_{20}$H$_{23}$N$_5$O$_4$S$_2$ | 461.6 | | 18.0$^a$ |
| 79 | 2.57(s, 3H, CH$_3$), 2.89(m, 4H, CH$_2$), 3.30(s, 3H, CH$_3$), 3.63(m, 4H, CH$_2$), 7.04(d, 1H, J=5.0, pyrmidinyl-H), 7.29(d, 1H, J=7.5, Ph-H), 7.58(t, 1H, J=8.0, Ph-H), 8.05(d, 1H, J=8.5, Ph-H), 8.23(s, 1H, Ph-H), 8.49(d, 1H, J=5.0, pyrimidinyl-H) | C$_{19}$H$_{21}$N$_5$O$_4$S$_2$ | 447.5 | | 17.4$^a$ |
| 80 | 2.80(s, 3H, CH$_3$), 3.54(s, 3H, CH$_3$), 4.19(m, 2H, CH$_2$), 7.24(d, 1H, J=5.5, pyrmidinyl-H), 7.64(d, 2H, J=8.5, Ph-H), 7.99(m, 2H, Ph-H), 8.46(brs, 2H, NH$_2$), 8.68(d, 1H, J=5.0, pyrimidinyl-H) | C$_{16}$H$_{17}$N$_5$OS | 327.4 | 328 | 10.8$^a$ |
| 81 | 2.33(s, 3H, CH$_3$), 2.56(s, 3H, CH$_3$), 3.30(s, 3H, CH$_3$), 7.03(d, 1H, J=5.4, pyrimidinyl-H), 8.22(d, 1H, J=2.4, pyridyl-H), 8.49(d, 1H, J=5.4, pyrimidinyl-H), 8.56(d, 1H, J=2.4, pyridyl-H), 9.90(s, 1H, NH) | C$_{15}$H$_{14}$ClN$_5$OS | 347.8 | 348 | 19.6$^a$ |
| 82 | 2.55(s, 3H, CH$_3$), 3.29(s, 3H, CH$_3$), 4.44(d, 2H, CH$_2$), 6.93(d, 1H, J=5.5, pyrimidinyl-H), 7.26(d, 2H, J=8.5, Ph-H), 7.60(t, 1H, J=6.5, pyridyl-H), 7.66(d, 2H, J=8.5, Ph-H), 8.00(t, 1H, J=7.5, pyridyl-H), 8.06(d, 1H, J=7.5, pyridyl-H), 8.40(d, 1H, J=5.5, pyrimidinyl-H), 8.65(d, 1H, J=5.0, pyridyl-H), 9.23(t, 1H, J=6.4, NH) | C$_{22}$H$_{20}$N$_6$O$_2$S | 433.4 | 433 | |
| 83 | 2.51(3H, s, CH$_3$), 3.25(3H, s, CH$_3$), 4.47(2H, d, CH$_2$, J=5.8), 6.68(1H, d, ArH, J=5.4), 7.32(1H, dd, ArH, J=7.8), 7.70(1H, d, ArH, J=7.8), 7.85(1H, s, ArH), 8.24(1H, d, ArH, J=5.4), 8.41(1H, d, ArH, J=7.8), 8.55(1H, s, NH) | C$_{15}$H$_{15}$N$_5$OS | 313.1 | 314 | 9.3$^a$ |
| 84 | 2.55(3H, s, CH$_3$), 3.15(3H, s, CH$_3$), 6.32(2H, s, NH$_2$), 6.34(1H, d, ArH, J=5.4), 8.11(1H, d, ArH, J=5.4) | C$_9$H$_{10}$N$_4$OS | 222.3 | 223 | 10.0$^a$ |
| 85 | 2.19(3H, s, COCH3), 2.67(3H, s, CH3), 3.23(3H, s, CH3), 7.15(1H, d, ArH, J=5.4), 8.57(1, d, ArH, J=5.4), 2.56(1H, s, NH) | C$_{11}$H$_{12}$N$_4$O$_2$S | 264.3 | 265 | 13.9$^a$ |

$^a$Gradient 0–60% MeCN over 20 min,
$^b$gradient 10–70% MeCN over 20 min.
$^c$Not determined, but FT-IR (RX-I, Perkin Elmer): 3271, 3171, 3087, 2945, 2824, 1651, 1564 cm$^{-1}$.

TABLE 3

Crystal data and structure refinement for compound 2.

A. CRYSTAL DATA

| | |
|---|---|
| Empirical formula | C$_{15}$H$_{13}$FN$_4$OS |
| Formula weight | 316.36 |
| Temperature | 150 K |
| Crystal system | Triclinic |
| Space group | P-1 |
| Unit cell dimensions | a = 6.9255(4) Å, α = 83.468(3)° |
| | b = 6.9912(4) Å, β = 82.448(3)° |
| | c = 14.7169(8) Å, γ = 78.519(3)° |
| Volume | 689.42(7) Å$^3$ |
| Number of reflections for cell | 4096 (3 < θ < 29 deg.) |
| Z | 2 |
| Density (calculated) | 1.524 Mg/m$^3$ |
| Absorption coefficient | 0.254 mm$^{-1}$ |
| F(000) | 328 |

B. DATA COLLECTION

| | |
|---|---|
| Crystal description | colourless lath |
| Crystal size | 0.38 × 0.16 × 0.16 mm |
| Theta range for data collection | 2.804 to 28.598° |
| Index ranges | −8 ≦ h ≦ 8, −9 ≦ k ≦ 9, −19 ≦ l ≦ 18 |
| Reflections collected | 6698 |
| Independent reflections | 3149 [R(int) = 0.02] |
| Scan type | ω |

TABLE 3-continued

Crystal data and structure refinement for compound 2.

| | |
|---|---|
| Absorption correction | Semi-empirical from equivalents ($T_{min}$ = 0.800, $T_{max}$ = 1.000) |
| C. SOLUTION AND REFINEMENT | |
| Solution | Patterson (shelxs) |
| Refinement type | Full-matrix least-squares on $F^2$ |
| Program used for refinement | CRYSTALS |
| Hydrogen atom placement | Geometric |
| Hydrogen atom treatment | Noref |
| Data/Parameters | 3148/200 |
| Goodness-of-fit on $F^2$ | 0.9661 |
| Conventional R [F > 4sigma(F)] | R1 = 0.0478 [2688 data] |
| Rw ($F^2$) | 0.1192 |
| Final maximum delta/sigma | 0.000778 |
| Weighting scheme | Sheldrick Weights |
| Largest diff. peak and hole | 0.30 and −0.26 e.Å$^{-3}$ |

TABLE 4

Atomic coordinates (×10$^4$) and equivalent isotropic displacement parameters (Å$^2$ × 10$^3$) for compound 2. U(eq) is defined as one third of the trace of the orthogonalized $U_{ij}$ tensor.

| Atom | x | y | z | U(eq) |
|---|---|---|---|---|
| S(1) | 1282(1) | 2788(1) | 10381(1) | 23 |
| C(2) | 1001(3) | 2262(3) | 11580(1) | 23 |
| O(2) | 309(3) | 3442(2) | 12141(1) | 32 |
| N(3) | 1684(3) | 289(3) | 11788(1) | 22 |
| C(31) | 1659(4) | −515(3) | 12755(2) | 27 |
| C(4) | 2394(3) | −793(3) | 11035(1) | 20 |
| C(41) | 3127(4) | −2941(3) | 11207(2) | 29 |
| C(5) | 2288(3) | 330(3) | 10219(1) | 20 |
| C(6) | 2800(3) | −90(3) | 9261(1) | 21 |
| C(7) | 3646(4) | −1916(3) | 8933(2) | 26 |
| C(8) | 4007(4) | −1960(3) | 7994(2) | 28 |
| N(9) | 3596(3) | −394(3) | 7384(1) | 27 |
| C(10) | 2780(3) | 1274(3) | 7763(1) | 22 |
| N(11) | 2372(3) | 1503(3) | 8667(1) | 22 |
| N(12) | 2290(3) | 2981(3) | 7216(1) | 26 |
| C(13) | 2508(3) | 3361(3) | 6248(1) | 24 |
| C(14) | 2209(4) | 5339(3) | 5911(2) | 27 |
| C(15) | 2364(4) | 5870(4) | 4971(2) | 30 |
| C(16) | 2825(4) | 4424(4) | 4384(2) | 30 |
| F(16) | 3016(3) | 4949(2) | 3456(1) | 44 |
| C(17) | 3116(4) | 2471(4) | 4687(2) | 33 |
| C(18) | 2943(4) | 1927(3) | 5628(2) | 29 |

TABLE 5

Bond lengths and angles for compound 2

| Bond | Length (Å) | Bond | Angle (deg.) |
|---|---|---|---|
| S(1)—C(5) | 1.751(2) | C(5)—S(1)—C(2) | 91.4(1) |
| S(1)—C(2) | 1.753(2) | N(3)—C(2)—O(2) | 125.2(2) |
| C(2)—N(3) | 1.380(3) | N(3)—C(2)—S(1) | 108.98(15) |
| C(2)—O(2) | 1.219(3) | O(2)—C(2)—S(1) | 125.79(17) |
| N(3)—C(4) | 1.394(3) | C(4)—N(3)—C(31) | 124.87(18) |
| N(3)—C(31) | 1.468(3) | C(4)—N(3)—C(2) | 115.53(17) |
| C(31)—H(313) | 1.000 | C(31)—N(3)—C(2) | 119.59(18) |
| C(31)—H(312) | 1.000 | H(313)—C(31)—H(312) | 109.479 |
| C(31)—H(311) | 1.000 | H(313)—C(31)—H(311) | 109.478 |
| C(4)—C(5) | 1.360(3) | H(312)—C(31)—H(311) | 109.475 |
| C(4)—C(41) | 1.490(3) | H(313)—C(31)—N(3) | 109.467 |
| C(41)—H(416) | 1.000 | H(312)—C(31)—N(3) | 109.465 |
| C(41)—H(415) | 1.000 | H(311)—C(31)—N(3) | 109.464 |
| C(41)—H(414) | 1.000 | C(5)—C(4)—C(41) | 128.95(19) |
| C(41)—H(413) | 1.000 | C(5)—C(4)—N(3) | 112.52(18) |
| C(41)—H(412) | 1.000 | C(41)—C(4)—N(3) | 118.53(18) |
| C(41)—H(411) | 1.000 | H(416)—C(41)—H(415) | 109.476 |

TABLE 5-continued

Bond lengths and angles for compound 2

| Bond | Length (Å) | Bond | Angle (deg.) |
|---|---|---|---|
| C(5)—C(6) | 1.456(3) | H(416)—C(41)—H(414) | 109.480 |
| C(6)—N(11) | 1.345(3) | H(415)—C(41)—H(414) | 109.476 |
| C(6)—C(7) | 1.405(3) | H(416)—C(41)—H(413) | 55.735 |
| C(7)—H(7) | 1.000 | H(415)—C(41)—H(413) | 141.065 |
| C(7)—C(8) | 1.374(3) | H(414)—C(41)—H(413) | 56.774 |
| C(8)—H(8) | 1.000 | H(416)—C(41)—H(412) | 141.066 |
| C(8)—N(9) | 1.344(3) | H(415)—C(41)—H(412) | 56.772 |
| N(9)—C(10) | 1.339(3) | H(414)—C(41)—H(412) | 55.733 |
| C(10)—N(12) | 1.370(3) | H(413)—C(41)—H(412) | 109.478 |
| C(10)—N(11) | 1.345(3) | H(416)—C(41)—H(411) | 56.773 |
| N(12)—H(12) | 1.000 | H(415)—C(41)—H(411) | 55.732 |
| N(12)—C(13) | 1.414(3) | H(414)—C(41)—H(411) | 141.065 |
| C(13)—C(18) | 1.393(3) | H(413)—C(41)—H(411) | 109.479 |
| C(13)—C(14) | 1.399(3) | H(412)—C(41)—H(411) | 109.474 |
| C(14)—H(14) | 1.000 | H(416)—C(41)—C(4) | 109.466 |
| C(14)—C(15) | 1.386(3) | H(415)—C(41)—C(4) | 109.465 |
| C(15)—H(15) | 1.000 | H(414)—C(41)—C(4) | 109.466 |
| C(15)—C(16) | 1.367(3) | H(413)—C(41)—C(4) | 109.466 |
| C(16)—C(17) | 1.371(3) | H(412)—C(41)—C(4) | 109.465 |
| C(16)—F(16) | 1.370(2) | H(411)—C(41)—C(4) | 109.465 |
| C(17)—H(17) | 1.000 | C(6)—C(5)—C(4) | 133.65(19) |
| C(17)—C(18) | 1.390(3) | C(6)—C(5)—S(1) | 114.82(15) |
| C(18)—H(18) | 1.000 | C(4)—C(5)—S(1) | 111.52(16) |
| | | N(11)—C(6)—C(7) | 120.19(19) |
| | | N(11)—C(6)—C(5) | 112.88(18) |
| | | C(7)—C(6)—C(5) | 126.93(19) |
| | | H(7)—C(7)—C(8) | 121.678 |
| | | H(7)—C(7)—C(6) | 121.678 |
| | | C(8)—C(7)—C(6) | 116.6(2) |
| | | H(8)—C(8)—N(9) | 117.745 |
| | | H(8)—C(8)—C(7) | 117.748 |
| | | N(9)—C(8)—C(7) | 124.5(2) |
| | | C(10)—N(9)—C(8) | 114.41(19) |
| | | N(12)—C(10)—N(11) | 113.15(18) |
| | | N(12)—C(10)—N(9) | 120.33(19) |
| | | N(11)—C(10)—N(9) | 126.52(19) |
| | | C(10)—N(11)—C(6) | 117.73(18) |
| | | H(12)—N(12)—C(13) | 114.731 |
| | | H(12)—N(12)—C(10) | 114.733 |
| | | C(13)—N(12)—C(10) | 130.54(19) |
| | | C(18)—C(13)—C(14) | 119.3(2) |
| | | C(18)—C(13)—N(12) | 124.8(2) |
| | | C(14)—C(13)—N(12) | 115.89(19) |
| | | H(14)—C(14)—C(15) | 119.751 |
| | | H(14)—C(14)—C(13) | 119.749 |
| | | C(15)—C(14)—C(13) | 120.5(2) |
| | | H(15)—C(15)—C(16) | 120.701 |
| | | H(15)—C(15)—C(14) | 120.700 |
| | | C(16)—C(15)—C(14) | 118.6(2) |
| | | C(17)—C(16)—F(16) | 118.7(2) |
| | | C(17)—C(16)—C(15) | 122.7(2) |
| | | F(16)—C(16)—C(15) | 118.6(2) |
| | | H(17)—C(17)—C(18) | 120.476 |
| | | H(17)—C(17)—C(16) | 120.480 |
| | | C(18)—C(17)—C(16) | 119.0(2) |
| | | H(18)—C(18)—C(17) | 120.045 |
| | | H(18)—C(18)—C(13) | 120.043 |
| | | C(17)—C(18)—C(13) | 119.9(2) |

TABLE 6

Anisotropic displacement parameters (Å$^2$ × 10$^3$) for compound 2. The anisotropic displacement factor exponent takes the form: $-2\pi^2$ [$h^2$ a*$^2$ $U_{11}$ + ... + 2 h k a* b* $U_{12}$].

| Atom | $U_{11}$ | $U_{22}$ | $U_{33}$ | $U_{23}$ | $U_{13}$ | $U_{12}$ |
|---|---|---|---|---|---|---|
| S (1) | 30 (1) | 18 (1) | 18 (1) | 0 (1) | −4 (1) | 0 (1) |
| C (2) | 26 (1) | 23 (1) | 20 (1) | −1 (1) | −4 (1) | −2 (1) |
| O (2) | 45 (1) | 27 (1) | 23 (1) | −7 (1) | −1 (1) | 1 (1) |
| N (3) | 27 (1) | 22 (1) | 18 (1) | 1 (1) | −5 (1) | −5 (1) |
| C (31) | 33 (1) | 30 (1) | 17 (1) | 3 (1) | −6 (1) | −5 (1) |
| C (4) | 22 (1) | 20 (1) | 20 (1) | −2 (1) | −4 (1) | −3 (1) |

TABLE 6-continued

Anisotropic displacement parameters ($Å^2 \times 10^3$) for compound 2. The anisotropic displacement factor exponent takes the form: $-2\pi^2$ [$h^2 a^{*2} U_{11} + \ldots + 2 h k a^* b^* U_{12}$].

| Atom | $U_{11}$ | $U_{22}$ | $U_{33}$ | $U_{23}$ | $U_{13}$ | $U_{12}$ |
|---|---|---|---|---|---|---|
| C (41) | 40 (1) | 21 (1) | 24 (1) | 1 (1) | −5 (1) | −1 (1) |
| C (5) | 21 (1) | 17 (1) | 21 (1) | −1 (1) | −4 (1) | −2 (1) |
| C (6) | 19 (1) | 24 (1) | 19 (1) | −1 (1) | −4 (1) | −3 (1) |
| C (7) | 29 (1) | 25 (1) | 21 (1) | −1 (1) | −4 (1) | 0 (1) |
| C (8) | 31 (1) | 25 (1) | 24 (1) | −5 (1) | −3 (1) | 3 (1) |
| N (9) | 30 (1) | 28 (1) | 19 (1) | −3 (1) | −2 (1) | 0 (1) |
| C (10) | 21 (1) | 25 (1) | 20 (1) | −2 (1) | −2 (1) | −4 (1) |
| C (11) | 25 (1) | 22 (1) | 18 (1) | −1 (1) | −5 (1) | −3 (1) |
| N (12) | 36 (1) | 23 (1) | 16 (1) | −1 (1) | −1 (1) | −2 (1) |
| C (13) | 24 (1) | 28 (1) | 18 (1) | 2 (1) | −1 (1) | −2 (1) |
| C (14) | 33 (1) | 27 (1) | 19 (1) | −2 (1) | 0 (1) | 1 (1) |
| C (15) | 35 (1) | 31 (1) | 21 (1) | 4 (1) | −1 (1) | 0 (1) |
| C (16) | 32 (1) | 38 (1) | 15 (1) | 2 (1) | −3 (1) | 0 (1) |
| F (16) | 62 (1) | 46 (1) | 16 (1) | 3 (1) | −4 (1) | 6 (1) |
| C (17) | 38 (1) | 36 (1) | 23 (1) | −5 (1) | −7 (1) | 0 (1) |
| C (18) | 35 (1) | 29 (1) | 21 (1) | −2 (1) | −5 (1) | −1 (1) |

TABLE 7

Hydrogen coordinates ($\times 10^4$) and isotropic displacement parameters ($Å^2 \times 10^3$) for compound 2.

| Atom | x | y | z | U(eq) |
|---|---|---|---|---|
| H(311) | 1079 | 555 | 13162 | 32 |
| H(312) | 3044 | −1086 | 12891 | 32 |
| H(313) | 836 | −1561 | 12868 | 32 |
| H(411) | 3010 | −3324 | 11885 | 34 |
| H(412) | 4548 | −3270 | 10944 | 34 |
| H(413) | 2316 | −3669 | 10907 | 34 |
| H(414) | 3585 | −3516 | 10606 | 34 |
| H(415) | 4258 | −3173 | 11589 | 34 |
| H(416) | 2031 | −3574 | 11540 | 34 |
| H(7) | 3970 | −3123 | 9361 | 30 |
| H(8) | 4617 | −3246 | 7749 | 32 |
| H(12) | 1677 | 4149 | 7559 | 30 |
| H(14) | 1879 | 6376 | 6351 | 32 |
| H(15) | 2144 | 7283 | 4728 | 35 |
| H(17) | 3447 | 1452 | 4238 | 39 |
| H(18) | 3131 | 509 | 5861 | 34 |

TABLE 8

Inhibition of protein kinases by example compounds (refer Table 1). Inhibition constants ($K_i$) were calculated according to Cheng, Y. -C.; Prusoff, W. H., Biochem. Pharmacol. 1973, 22, 3099–3108 based on experimentally determined $IC_{50}$ values and $K_{m, ATP}$ for the different kinases.

| | Kinase Inhibition $K_i$ (μM) | | | | | | |
|---|---|---|---|---|---|---|---|
| No. | CDK1 - cyclin B | CDK2 - cyclin E | CDK2 - cyclin A | CDK4 - cyclin D1 | CDK7 - cyclin H | CDK9 - cyclin T1 | Aurora A |
| 1 | 1.0 | 0.01 | 0.17 | 0.30 | 0.0028 | 0.0003 | 0.70 |
| 2 | | | | | | 0.0008 | 0.35 |
| 3 | | | | | | 0.0007 | |
| 4 | 0.46 | 0.13 | 0.20 | 1.6 | 4.1 | | |
| 6 | 0.26 | 0.38 | 0.19 | 0.57 | 0.92 | | |
| 7 | 0.13 | 0.043 | 0.025 | 0.54 | 0.62 | | |
| 8 | 0.75 | 0.75 | 0.20 | 0.53 | 0.86 | 0.041 | |
| 9 | 5.2 | 0.59 | 0.17 | 0.67 | 1.3 | | |
| 10 | 0.28 | 0.13 | 0.021 | 0.99 | 0.52 | | |
| 11 | 0.72 | 0.061 | 0.22 | 0.38 | 0.036 | 0.0004 | |
| 12 | 0.38 | 0.066 | | | | 0.024 | |
| 13 | 1.5 | 0.53 | 0.23 | 0.27 | 0.17 | 0.093 | |
| 14 | 0.70 | 0.35 | 0.84 | 2.1 | | 0.035 | |
| 15 | 0.60 | 0.58 | 0.46 | 9.6 | | 0.045 | |
| 16 | 0.40 | 0.0005 | 0.042 | 0.10 | 0.0068 | 0.0019 | |
| 17 | 6.9 | 0.26 | 0.18 | 0.19 | 0.51 | 0.077 | |
| 18 | 0.022 | 0.028 | 0.059 | 0.17 | 0.028 | 0.0012 | |
| 19 | | 1.7 | | | 5.1 | 1.8 | |
| 20 | | 6.5 | | | 0.91 | 0.085 | |
| 21 | 2.3 | 0.19 | 0.55 | | 0.22 | 0.17 | |
| 22 | 0.082 | 0.053 | 0.0005 | 1.3 | 0.0019 | 0.0072 | 0.11 |
| 23 | 0.29 | 0.016 | 0.062 | 0.87 | 0.0014 | 0.0003 | |
| 24 | 6.3 | 1.9 | 1.1 | 24 | | 0.37 | |
| 25 | | 2.7 | 23 | | | 4.4 | |
| 26 | 7.0 | 0.29 | 0.15 | 0.28 | 0.22 | 0.69 | |
| 27 | | 0.50 | 2.0 | 3.3 | 1.6 | 0.69 | 0.033 |
| 29 | | 0.033 | | 0.17 | 0.043 | 0.0070 | |
| 30 | 0.67 | 0.29 | 0.56 | 21 | 0.031 | 0.19 | |
| 31 | | | | | 0.43 | | |
| 32 | 0.50 | 0.068 | | | | 0.0065 | |
| 33 | 0.030 | 0.050 | 0.76 | 0.035 | 0.023 | 0.0024 | |
| 34 | 3.5 | 1.1 | 0.60 | | 0.23 | 1.8 | |
| 35 | 2.6 | 0.66 | 0.19 | 2.0 | 0.20 | 0.49 | |
| 37 | 9.9 | 8.6 | | | | | |
| 38 | 0.47 | 0.18 | 0.30 | 0.050 | 0.038 | 0.010 | 0.088 |
| 39 | 0.064 | 0.098 | 0.0086 | 0.15 | 0.60 | 0.014 | |
| 40 | 0.017 | 0.0032 | 0.011 | 0.23 | 0.071 | 0.0024 | |
| 41 | 0.049 | 0.012 | 0.023 | 0.13 | 0.29 | 0.0089 | |
| 42 | 0.58 | 0.034 | 0.22 | 0.77 | 0.38 | 0.019 | |
| 43 | | 0.0020 | | 0.13 | 0.019 | | |
| 44 | 0.086 | 0.062 | 0.099 | 0.036 | 0.019 | 0.0034 | 0.038 |
| 45 | 0.30 | 0.024 | 0.052 | 5.0 | 0.22 | 0.011 | 0.043 |

TABLE 8-continued

Inhibition of protein kinases by example compounds (refer Table 1). Inhibition constants ($K_i$) were calculated according to Cheng, Y. -C.; Prusoff, W. H., Biochem. Pharmacol. 1973, 22, 3099–3108 based on experimentally determined $IC_{50}$ values and $K_{m, ATP}$ for the different kinases.

| | Kinase Inhibition $K_i$ (μM) | | | | | |
|---|---|---|---|---|---|---|
| No. | CDK1 - cyclin B | CDK2 - cyclin E | CDK2 - cyclin A | CDK4 - cyclin D1 | CDK7 - cyclin H | CDK9 - cyclin T1 | Aurora A |
| 46 | | 0.57 | 0.40 | | 0.79 | 0.057 | 1.1 |
| 47 | 0.18 | 0.015 | 0.087 | 1.8 | 0.017 | 0.0030 | 0.053 |
| 48 | | | | | | 0.23 | |
| 49 | 0.93 | 1.3 | 3. | 0.0097 | 1.1 | 0.030 | 0.11 |
| 50 | 0.12 | 0.050 | 0.12 | | 0.14 | 0.080 | 0.032 |
| 51 | 2.1 | 0.27 | | | 0.97 | 0.19 | |
| 52 | 0.73 | 0.077 | 0.16 | 1.2 | 0.070 | 0.016 | 0.025 |
| 53 | | 0.18 | 0.59 | | | | |
| 55 | 0.16 | 0.039 | 0.042 | 0.11 | 0.11 | 0.0022 | 0.046 |
| 56 | | | | | 2.9 | 0.46 | 2.6 |
| 57 | 0.36 | 0.052 | 0.54 | 0.021 | 1.3 | 0.0016 | 0.16 |
| 58 | 1.1 | 0.10 | 0.60 | 5.1 | 0.096 | 0.0064 | 0.84 |
| 59 | 0.085 | 0.0016 | 0.16 | 0.097 | 0.21 | 0.0070 | 0.11 |
| 60 | 0.021 | 0.0034 | 0.021 | 0.022 | 0.039 | 0.0003 | 0.030 |
| 62 | 0.43 | 0.35 | 0.61 | 0.33 | 1.1 | 0.0048 | 0.41 |
| 64 | 0.87 | | | | 3.9 | 0.0057 | 0.17 |
| 65 | 0.0041 | 0.0001 | 0.0022 | | 0.94 | 0.014 | 0.53 |
| 66 | | 0.20 | | | 2.3 | 0.021 | |
| 67 | | | 1.3 | 1.4 | 0.36 | 0.0048 | 0.39 |
| 68 | | | | | | 0.14 | |
| 69 | 1.7 | 0.16 | 0.95 | 0.10 | 0.012 | 0.021 | 0.039 |
| 71 | 0.14 | | 0.28 | 0.17 | 0.073 | | 0.11 |
| 72 | 0.0054 | 0.0005 | 0.0029 | 0.83 | 1.2 | 0.011 | 0.51 |
| 73 | 1.1 | 0.080 | 0.65 | | | 0.38 | |
| 74 | | 1.4 | | 0.98 | 2.7 | 0.050 | 0.87 |
| 75 | 0.62 | 0.38 | 0.41 | 0.15 | 0.37 | 0.0095 | 0.25 |
| 76 | | 0.089 | | | 0.80 | 0.021 | 0.15 |
| 78 | | 2.1 | | | 1.2 | 0.027 | 1.1 |
| 79 | | 1.5 | | | 2.6 | | 1.4 |
| 80 | | | | | | | 0.38 |
| 81 | | | | | | | 0.50 |
| 82 | | | | | | | 0.063 |
| 83 | | 1.6 | | 1.3 | | 0.32 | |
| 84 | | | | | | 0.13 | |
| 85 | | | | | | 0.29 | |

TABLE 9

In vitro GSK3 and DYRKIA inhibitory activity of example compounds.

| | $IC_{50}$ (μM) | | |
|---|---|---|---|
| Compound No. | GSK3β | GSK3α | DYRK1A |
| 42 | 0.0385 | | |
| 43 | 0.0415 | | |
| 44 | 0.0178 | | |
| 45 | 0.0152 | | |
| 46 | 0.1005 | | |
| 47 | 0.0308 | | |
| 48 | 0.0619 | | |
| 49 | 0.38 | | |
| 50 | 0.102 | | |
| 51 | 0.5425 | | |
| 53 | 0.0435 | | |
| 54 | 0.1583 | | |
| 55 | 0.082 | | |
| 56 | 3.5 | | |
| 57 | 0.0178 | | |
| 58 | 0.0233 | | |
| 59 | 0.0183 | | |
| 60 | 0.0018 | | |
| 62 | 0.022 | 0.027 | 0.051 |
| 64 | 0.003 | 0.0024 | 0.077 |
| 65 | 0.009 | | |
| 66 | 0.015 | 0.032 | 0.356 |
| 67 | 0.023 | 0.0178 | 0.019 |
| 68 | 0.061 | 0.1358 | 0.073 |
| 69 | 0.096 | | |
| 70 | 0.0068 | 0.0036 | N.T. |
| 71 | 0.0053 | | |
| 72 | 0.0083 | | |
| 74 | 0.075 | | |
| 73 | 0.0665 | | |
| 75 | 0.025 | 0.031 | 0.026 |
| 76 | 0.0189 | 0.042 | 0.148 |
| 77 | 0.0709 | 0.0615 | N.T. |
| 78 | 0.1304 | | |
| 79 | 0.0356 | | |
| 80 | 0.0698 | | |
| 81 | 0.0032 | | |
| 82 | 0.0281 | | |

TABLE 10

Glycogen synthase activation in HEK293 cell, mouse adipocytes, and rat myotubes.

| Compound | HEK293 EC$_{50}$ (μM) | HEK293 Max FI (% to LiCl) | Mouse adipocytes EC$_{50}$ (μM) | Mouse adipocytes Max FI (% to LiCl) | Rat myotubes EC$_{50}$ (μM) | Rat myotubes Max FI (% to LiCl) |
|---|---|---|---|---|---|---|
| 62 | 0.684 ± 0.133 | 117 | 0.432 ± 0.179 | 234 | 1.611 ± 0.199 | 130 |
| 64 | 0.049 ± 0.07 | 107 | 0.148 ± 0.07 | 143 | 1.24 ± 0.61 | 152 |
| 67 | 3.72 ± 2.5 | 85 | 4.83 ± 4.6 | 177 | 10.48 ± 0.99 | 112 |
| 68 | 8.34 ± 1.88 | 96 | 9.55 ± 7.4 | 50 | N.D. | — |
| 75 | 5.17 ± 2.20 | 108 | 2.19 ± 0.40 | 181 | 8.49 ± 2.48 | 157 |
| 76 | 0.444 ± 0.178 | 88 | 1.11 ± 0.53 | 196 | N.D. | — |

TABLE 11

PEPCK gene expression in HEPG2 cells - qPCR assay.

| HEPG2 treatment | % of maximum stimulation |
|---|---|
| Dexamethasone/cAMP | 100 |
| Serum free medium | 13.24 ± 1.68 |
| 100 nM Insulin + Dex/cAMP | 44.09 ± 11.07 |
| 1 μM compound 64 + Dex/cAMP | 6.9 ± 1.5 |
| 0.1 μM compound 64 + Dex/cAMP | 11.4 ± 3.2 |
| 1 μM compound 64 + Dex/cAMP | 84.3 ± 12.3 |
| 10 μM compound 68 + Dex/cAMP | 60.7 ± 20.0 |
| 1 μM compound 67 + Dex/cAMP | 100.7 ± 38.2 |
| 10 μM compound 67 + Dex/cAMP | 17.4 ± 0.97 |
| 1 μM compound 75 + Dex/cAMP | 37.2 ± 0.37 |
| 10 μM compound 75 + Dex/cAMP | 17.1 ± 0.68 |

TABLE 12

Effect of example compounds on oral glucose tolerance in ZDF fa/fa rats.

| Compound | Time (min) | Average Blood levels (ng/mL) | SD | % Glucose decrease-AUC (0–180 min) | % Glucose Decrease AUC (−270–180 min) |
|---|---|---|---|---|---|
| 76 | 30 | 43.0 | 16.0 | 0.5 | 0 |
|    | 60 | 48.1 | 18.2 |     |   |
| 64 | 30 | 248.3 | 101.5 | 8 | 9 |
|    | 60 | 267.6 | 63.4 |   |   |
| 67 | 30 | 349.6 | 57.7 | 7.5 | 14 |
|    | 60 | 271.4 | 45.0 |     |    |
| 62 | 30 | 27.6 | 9.9 | 3.6 | 9 |
|    | 60 | 29.7 | 10.7 |    |   |
| 66 | 30 | 157.0 | 29.1 | 17* | 20 |
|    | 60 | 161.5 | 48.2 |     |    |
| 68 | 30 | 114.7 | 34.6 | 8.4* | 5 |
|    | 60 | 70.1 | 19.2 |      |   |
| 75 | 30 | N.D. |  | 6.4 | 13 |
|    | 60 | N.D. |  |     |    |

*$p < 0.05$.

The invention claimed is:

1. A compound of formula I, or a pharmaceutically acceptable salt thereof,

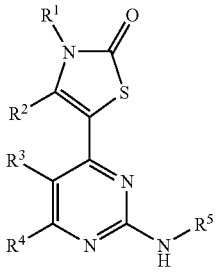

I wherein
$R^1$ and $R^5$ are each independently H, C(OR$^{j'}$) or a hydrocarbyl group optionally substituted by one or more $R^6$ groups;
$R^2$, $R^3$, and $R^4$ are each independently H, alkyl or alkenyl, each of which may be optionally substituted with one or more $R^7$ groups;
$R^6$ and $R^7$ are each independently halogen, NO$_2$, CN, (CH$_2$)$_m$OR$^a$, O(CH$_2$)$_n$OR$^b$, (CH$_2$)$_p$NR$^c$R$^d$, CF$_3$, COOR$^e$, CONR$^f$R$^g$, COR$^h$, SO$_3$H, SO$_2$R$^i$, SO$_2$NR$^j$R$^k$, (CH$_2$)$_q$NR$^{a'}$COR$^{g'}$, R$^{l'}$, (CH$_2$)$_r$NR$^{b'}$SO$_2$R$^{h'}$, SO$_2$NR$^{d'}$R$^{i'}$, SO$_2$NR$^{e'}$(CH$_2$)$_s$OR$^{c'}$, heterocycloalkyl or heteroaryl, wherein said heterocycloalkyl and heteroaryl may be optionally substituted by one or more substituents selected from aralkyl, sulfonyl, R$^m$ and COR$^n$;
$R^{g'}$, $R^{h'}$, $R^{i'}$ and $R^{j'}$ are each independently selected from alkyl, aryl, aralkyl and heteroaryl, each of which may be optionally substituted with one or more substituents selected from halogen, OH, NO$_2$, NH$_2$CF$_3$ and COOH;
m, p, q and r are each independently 0, 1, 2 or 3;
n and s are each independently 1, 2, or 3; and
$R^{a-n}$ and $R^{a'-f'}$ are each independently H or alkyl,
with the proviso that the compound is other than:
3,4-Dimethyl-5-[2-(3-nitro-phenylamino)-pyrimidin-4-yl]-3H-thiazol-2-one;
5-[2-(4-Fluoro-phenylamino)-pyrimidin-4-yl]-3,4-dimethyl-3H-thiazol-2-one;
5-[2-(4-Hydroxy-phenylamino)-pyrimidin-4-yl]-3,4-dimethyl-3H-thiazol-2-one;
5-[2-(4-Chloro-phenylamino)-pyrimidin-4-yl]-3,4-dimethyl-3H-thiazol-2-one;
5-[2-(4-Methoxy-phenylamino)-pyrimidin-4-yl]-3,4-dimethyl-3H-thiazol-2-one;

5-[2-(3-Hydroxy-phenylamino)-pyrimidin-4-yl]-3,4-dimethyl-3H-thiazol-2-one;

5-[2-(4-Dimethylamino-phenylamino)-pyrimidin-4-yl]-3,4-dimethyl-3H-thiazol-2-one;

5-[2-(4-Fluoro-3-nitro-phenylamino)-pyrimidin-4-yl]-3,4-dimethyl-3H-thiazol-2-one;

3,4-Dimethyl-5-[2-(4-methyl-3-nitro-phenylamino)-pyrimidin-4-yl]-3H-thiazol-2-one;

5-[2-(4-Fluoro-3-methyl-phenylamino)-pyrimidin-4-yl]-3,4-dimethyl-3H-thiazol-2-one;

5-[2-(3-Iodo-4-methyl-phenylamino)-pyrimidin-4-yl]-3,4-dimethyl-3H-thiazol-2-one;

5-[2-(4-Chloro-3-methyl-phenylamino)-pyrimidin-4-yl]-3,4-dimethyl-3H-thiazol-2-one;

5-[2-(4-Iodo-3-phenylamino)-pyrimidin-4-yl]-3,4-dimethyl-3H-thiazol-2-one.

2. A compound according to claim 1 wherein $R^1$ and $R^5$ are each independently H or a $C_{1-20}$ hydrocarbyl group optionally comprising up to six heteroatoms selected from N, O, and S, and which is optionally substituted by one, two or three $R^6$ groups.

3. A compound according to claim 1, wherein $R^5$ is aryl or heteroaryl, each of which may be optionally substituted by one or more $R^6$ groups.

4. A compound according to claim 3, wherein $R^5$ is phenyl or pyridinyl, each of which may be optionally substituted by one or more $R^6$ groups.

5. A compound according to claim 1, wherein $R^1$ is H or alkyl.

6. A compound according to claim 1, wherein $R^2$, $R^3$, and $R^4$ are each independently H, $C_1$-$C_6$ alkyl or $C_2$-$C_6$ alkenyl, each of which may be optionally substituted with one, two or three $R^7$ groups.

7. A compound according to claim 1, wherein $R^6$ and $R^7$ are each independently F, Cl, Br, I, $NO_2$, CN, OH, OMe, OEt, $CH_2OH$, $O(CH_2)_2OMe$, $NH_2$, NHMe, $NMe_2$, $CF_3$, COOH, $CONH_2$, CONHMe, $CONMe_2$, COMe, $SO_3H$, $SO_2Me$, $SO_2NH_2$, $SO_2NHMe$, $SO_2NMe_2$, morpholine, piperidine, piperazine, N-acetylpiperazine, N-methylpiperazine, triazole, or tetrazole.

8. A compound according to claim 1, wherein $R^3$ and $R^4$ are both H and $R^2$ is Me.

9. A compound according to claim 1, wherein said compound is of formula II, pharmaceutically acceptable salt thereof,

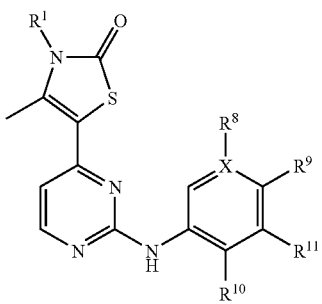

II wherein
$R^1$ is as defined in claim 1;
X is C; or X is N and $R^8$ is absent;
$R^8$, $R^9$, $R^{10}$ and $R^{11}$ are each independently H, halogen, $NO_2$, CN, $(CH_2)_mOR^a$, $O(CH_2)_nOR^b$, $(CH_2)_pNR^cR^d$, $CF_3$, $COOR^e$, $CONR^fR^g$, $COR^h$, $SO_3H$, $SO_2R^i$, $SO_2NR^jR^k$, $(CH_2)_qNR^{a'}COR^{g'}$, $R^{f'}$, $(CH_2)_rNR^{b'}SO_2R^{h'}$, $SO_2NR^{d'}R^{i'}$, $SO_2NR^{e'}(CH_2)_sOR^{c'}$, heterocycloalkyl or heteroaryl, wherein said heterocycloalkyl and heteroaryl may be optionally substituted by one or more substituents selected from aralkyl, sulfonyl, $R^m$ and $COR^n$.

10. A compound according to claim 9 wherein
$R^1$ is H or alkyl;
$R^8$ is H, $NO_2$, $OR^p$, halogen, $CF_3$, CN, $COR^q$, alkyl, $NR^rR^s$, $O(CH_2)_nOR^t$;
$R^9$ is H, $OR^u$, halogen, alkyl, $NR^vR^w$, heterocycloalkyl optionally substituted with one or more substituents selected from $R^m$ and $COR^n$;
t is 0, 1, 2 or 3;
$R^{10}$ is H, alkyl or $NR^xR^y$; and
$R^{p-y}$ are each independently H or alkyl.

11. A compound according to claim 1, wherein $R^1$ is H, Me, Et or 3-methylbutyl.

12. A compound according to claim 10, wherein:
$R^8$ is H, $NO_2$, OH, Me, I, $CF_3$, CN, $CH_2OH$, $CO_2H$, $CO_2Me$ or $NH_2$;
$R^9$ is H, F, OH, I, Cl, Br, OMe, $NMe_2$, morpholine, Me, N-methylpiperazine, N-acetylpiperazine or piperazine; and
$R^{10}$ is H, Me or $NMe_2$.

13. A compound according to claim 9, wherein X is N and $R^8$ is absent.

14. A compound according to claim 9, wherein X is C.

15. A compound according to claim 1, which is selected from the following:

5-[2-(4-Bromo-phenylamino)-pyrimidin-4-yl]-3,4-dimethyl-3H-thiazol-2-one;

3,4-Dimethyl-5-[2-(4-morpholin-4-yl-phenylamino)-pyrimidin-4-yl]-3H-thiazol-2-one;

3,4-Dimethyl-5-{2-[4-(4-methyl-piperazin-1-yl)-phenylamino]-pyrimidin-4-yl}-3H-thiazol-2-one;

3-[4-(3,4-Dimethyl-2-oxo-2,3-dihydro-thiazol-5-yl)-pyrimidin-2-ylamino]-benzonitrile;

5-{2-[4-(4-Acetyl-piperazin-1-yl)-phenylamino]-pyrimidin-4-yl}-3,4-dimethyl-3H-thiazol-2-one;

5-[2-(4-Chloro-3-hydroxymethyl-phenylamino)-pyrimidin-4-yl]-3,4-dimethyl-3H-thiazol-2-one;

3,4-Dimethyl-5-[2-(3-trifluoromethyl-phenylamino)-pyrimidin-4-yl]-3H-thiazol-2-one;

3,4-Dimethyl-5-[2-(2-methyl-5-nitro-phenylamino)-pyrimidin-4-yl]-3H-thiazol-2-one;

3,4-Dimethyl-5-[2-(4-methyl-3-trifluoromethyl-phenylamino)-pyrimidin-4-yl]-3H-thiazol-2-one;

5-[2-(4-Dimethylamino-3-nitro-phenylamino)-pyrimidin-4-yl]-3,4-dimethyl-3H-thiazol-2-one;

3-Ethyl-4-methyl-5-[2-(3-nitro-phenylamino)-pyrimidin-4-yl]-3H-thiazol-2-one;

2-Chloro-5-[4-(3-ethyl-4-methyl-2-oxo-2,3-dihydro-thiazol-5-yl)-pyrimidin-2-ylamino]-benzoic acid;

2-Chloro-5-[4-(3-ethyl-4-methyl-2-oxo-2,3-dihydro-thiazol-5-yl)-pyrimidin-2-ylamino]-benzoic acid methyl ester;

5-[2-(4-Dimethylamino-phenylamino)-pyrimidin-4-yl]-3-ethyl-4-methyl-3H-thiazol-2-one;

3-Ethyl-4-methyl-5-[2-(4-morpholin-4-yl-phenylamino)-pyrimidin-4-yl]-3H-thiazol-2-one;

3-Ethyl-4-methyl-5-[2-(4-methyl-3-nitro-phenylamino)-pyrimidin-4-yl]-3H-thiazol-2-one;

5-[2-(4-Dimethylamino-3-nitro-phenylamino)-pyrimidin-4-yl]-3-ethyl-4-methyl-3H-thiazol-2-one;

4-Methyl-3-(3-methyl-butyl)-5-[2-(3-nitro-phenylamino)-pyrimidin-4-yl]-3H-thiazol-2-one;

5-[2-(4-Chloro-phenylamino)-pyrimidin-4-yl]-4-methyl-3-(3-methyl-butyl)-3H-thiazol-2-one;
5-[2-(6-Chloro-pyridin-3-ylamino)-pyrimidin-4-yl]-3,4-dimethyl-3H-thiazol-2-one;
3-Ethyl-5-[2-(6-methoxy-pyridin-3-ylamino)-pyrimidin-4-yl]-4-methyl-3H-thiazol-2-one;
5-[2-(6-Chloro-pyridin-3-ylamino)-pyrimidin-4-yl]-4-methyl-3-(3-methyl-butyl)-3H-thiazol-2-one;
5-[2-(6-Methoxy-pyridin-3-ylamino)-pyrimidin-4-yl]-4-methyl-3-(3-methyl-butyl)-3H-thiazol-2-one;
5-[2-(2-Dimethylamino-5-nitro-phenylamino)-pyrimidin-4-yl]-3,4-dimethyl-3H-thiazol-2-one;
3,4-Dimethyl-5-[2-(4-piperazin-1-yl-phenylamino)-pyrimidin-4-yl]-3H-thiazol-2-one;
5-[2-(3-Amino-4-methyl-phenylamino)-pyrimidin-4-yl]-3,4-dimethyl-3H-thiazol-2-one;
4-Methyl-5-[2-(3-nitro-phenylamino)-pyrimidin-4-yl]-3H-thiazol-2-one;
4-Methyl-5-[2-(4-methyl-3-nitro-phenylamino)-pyrimidin-4-yl]-3H-thiazol-2-one;
N-{3-[4-(3,4-Dimethyl-2-oxo-2,3-dihydro-thiazol-5-yl)-pyrimidin-2-ylamino]-benzyl}-acetamide;
3-Ethyl-5-[2-(3-hydroxy-phenylamino)-pyrimidin-4-yl]-4-methyl-3H-thiazol-2-one;
5-[2-(3-Chloro-4-piperazin-1-yl-phenylamino)-pyrimidin-4-yl]-3,4-dimethyl-3H-thiazol-2-one;
3-Ethyl-5-[2-(4-fluoro-phenylamino)-pyrimidin-4-yl]-4-methyl-3H-thiazol-2-one;
5-[2-(4-Chloro-phenylamino)-pyrimidin-4-yl]-3-ethyl-4-methyl-3H-thiazol-2-one;
3-Ethyl-5-[2-(3-hydroxy-4-methyl-phenylamino)-pyrimidin-4-yl]-4-methyl-3H-thiazol-2-one;
5-[2-(4-Chloro-3-trifluoromethyl-phenylamino)-pyrimidin-4-yl]-3-ethyl-4-methyl-3H-thiazol-2-one;
5-{2-[3-(4-Acetyl-piperazin-1-yl)-phenylamino]-pyrimidin-4-yl}-3,4-dimethyl-3H-thiazol-2-one;
3-Ethyl-5-[2-(3-methoxy-phenylamino)-pyrimidin-4-yl]-4-methyl-3H-thiazol-2-one;
5-[2-(4-Chloro-3-methyl-phenylamino)-pyrimidin-4-yl]-3-ethyl-4-methyl-3H-thiazol-2-one;
3-Ethyl-4-methyl-5-[2-(4-nitro-phenylamino)-pyrimidin-4-yl]-3H-thiazol-2-one;
4-[4-(3-Ethyl-4-methyl-2-oxo-2,3-dihydro-thiazol-5-yl)-pyrimidin-2-ylamino]-benzenesulfonic acid;
3-[4-(3-Ethyl-4-methyl-2-oxo-2,3-dihydro-thiazol-5-yl)-pyrimidin-2-ylamino]-benzenesulfonic acid;
N-{3-[4-(3,4-Dimethyl-2-oxo-2,3-dihydro-thiazol-5-yl)-pyrimidin-2-ylamino]-benzyl}-methane-sulfonamide;
5-[2-(5-Methoxy-2-methyl-phenylamino)-pyrimidin-4-yl]-3,4-dimethyl-3H-thiazol-2-one
N-{3-[4-(3,4-Dimethyl-2-oxo-2,3-dihydro-thiazol-5-yl)-pyrimidin-2-ylamino]-benzyl}-benzamide;
N-{3-[4-(3,4-Dimethyl-2-oxo-2,3-dihydro-thiazol-5-yl)-pyrimidin-2-ylamino]-benzyl}-C,C,C-trifluoro-methanesulfonamide;
N-{4-[4-(3,4-Dimethyl-2-oxo-2,3-dihydro-thiazol-5-yl)-pyrimidin-2-ylamino]-benzyl}-acetamide;
3-[4-(3,4-Dimethyl-2-oxo-2,3-dihydro-thiazol-5-yl)-pyrimidin-2-ylamino]-benzenesulfonamide;
3-[4-(3,4-Dimethyl-2-oxo-2,3-dihydro-thiazol-5-yl)-pyrimidin-2-ylamino]-N-isopropyl-4-methyl-benzamide;
3-[4-(3,4-Dimethyl-2-oxo-2,3-dihydro-thiazol-5-yl)-pyrimidin-2-ylamino]-N-ethyl-benzenesulfonamide;
5-[2-(5-Hydroxymethyl-2-methyl-phenylamino)-pyrimidin-4-yl]-3,4-dimethyl-3H-thiazol-2-one;
N-{3-[4-(3,4-Dimethyl-2-oxo-2,3-dihydro-thiazol-5-yl)-pyrimidin-2-ylamino]-5-trifluoromethyl-phenyl}-acetamide;
4-[4-(3,4-Dimethyl-2-oxo-2,3-dihydro-thiazol-5-yl)-pyrimidin-2-ylamino]-N-(2-methoxy-ethyl)-benzenesulfonamide;
5-[2-(4-Chloro-3-trifluoromethyl-phenylamino)-pyrimidin-4-yl]-3,4-dimethyl-3H-thiazol-2-one;
3-[4-(3,4-Dimethyl-2-oxo-2,3-dihydro-thiazol-5-yl)-pyrimidin-2-ylamino]-N-(2-methoxy-ethyl)-benzenesulfonamide;
5-[2-(3-Bromo-5-trifluoromethyl-phenylamino)-pyrimidin-4-yl]-3,4-dimethyl-3H-thiazol-2-one;
5-{2-[4-(4-Benzyl-piperazin-1-yl)-phenylamino]-pyrimidin-4-yl}-3,4-dimethyl-3H-thiazol-2-one;
4-[4-(3,4-Dimethyl-2-oxo-2,3-dihydro-thiazol-5-yl)-pyrimidin-2-ylamino]-2-trifluoromethyl-benzonitrile;
5-[2-(3-Amino-5-trifluoromethyl-phenylamino)-pyrimidin-4-yl]-3,4-dimethyl-3H-thiazol-2-one;
4-[4-(3,4-Dimethyl-2-oxo-2,3-dihydro-thiazol-5-yl)-pyrimidin-2-ylamino]-N-(2-hydroxy-ethyl)-benzenesulfonamide;
N-Benzyl-4-[4-(3,4-dimethyl-2-oxo-2,3-dihydro-thiazol-5-yl)-pyrimidin-2-ylamino]-benzenesulfonamide;
3-[4-(3,4-Dimethyl-2-oxo-2,3-dihydro-thiazol-5-yl)-pyrimidin-2-ylamino]-N-isopropyl-benzenesulfonamide;
3-[4-(3,4-Dimethyl-2-oxo-2,3-dihydro-thiazol-5-yl)-pyrimidin-2-ylamino]-N-(2-hydroxy-ethyl)-benzenesulfonamide;
3,4-Dimethyl-5-[2-(3-methylamino-5-trifluoromethyl-phenylamino)-pyrimidin-4-yl]-3H-thiazol-2-one;
N-Benzyl-3-[4-(3,4-dimethyl-2-oxo-2,3-dihydro-thiazol-5-yl)-pyrimidin-2-ylamino]-benzenesulfonamide;
3,4-Dimethyl-5-{2-[4-methyl-3-(morpholine-4-sulfonyl)-phenylamino]-pyrimidin-4-yl}-3H-thiazol-2-one;
3,4-Dimethyl-5-{2-[3-(morpholine-4-sulfonyl)-phenylamino]-pyrimidin-4-yl}-3H-thiazol-2-one;
5-[2-(4-Aminomethyl-phenylamino)-pyrimidin-4-yl]-3,4-dimethyl-3H-thiazol-2-one;
5-[2-(6-Chloro-5-methyl-pyridin-3-ylamino)-pyrimidin-4-yl]-3,4-dimethyl-3H-thiazol-2-one;
Pyridine-2-carboxylic acid 4-[4-(3,4-dimethyl-2-oxo-2,3-dihydro-thiazol-5-yl)-pyrimidin-2-ylamino]-benzylamide;
3,4-Dimethyl-5-{2-[(pyridin-3-ylmethyl)-amino]-pyrimidin-4-yl}-3H-thiazol-2-one;
5-(2-Amino-pyrimidin-4-yl)-3,4-dimethyl-3H-thiazol-2-one;
N-[4-(3,4-Dimethyl-2-oxo-2,3-dihydro-thiazol-5-yl)-pyrimidin-2-yl]-acetamide.

16. A pharmaceutical composition comprising a compound according to claim 1, admixed with a pharmaceutically acceptable diluent, excipient or carrier.

17. A method of treating rheumatoid arthritis, comprising administering to a subject in need thereof, a compound according to claim 1, in an amount sufficient to treat rheumatoid arthritis, such that the subject is treated for rheumatoid arthritis.

18. The method according to claim 17 wherein the compound is administered in an amount sufficient to inhibit at least one PLK enzyme.

19. The method according to claim 18, wherein the PLK enzyme is PLK1.

20. The method according to claim 17 wherein the compound is administered in an amount sufficient to inhibit at least one CDK enzyme.

21. The method according to claim 20, wherein the CDK enzyme is CDK1, CDK2, CDK3, CDK4, CDK6, CDK7, CDK8 and/or CDK9.

22. The method according to claim 17 wherein the compound is administered in an amount sufficient to inhibit aurora kinase.

23. A method of treating diabetes, comprising administering to a subject in need thereof, a compound according to claim 1, in an amount sufficient to treat diabetes, such that the subject is treated for diabetes.

24. The method according to claim 23, wherein the diabetes is Type II diabetes.

25. The method according to claim 23, wherein the compound is administered in an amount sufficient to inhibit GSK.

26. The method according to claim 25, wherein the compound is administered in an amount sufficient to inhibit GSK3β.

27. A process for preparing a compound of formula I as defined in claim 1, said process comprising reacting a compound of formula X with a compound of formula XI to form a compound of formula I,

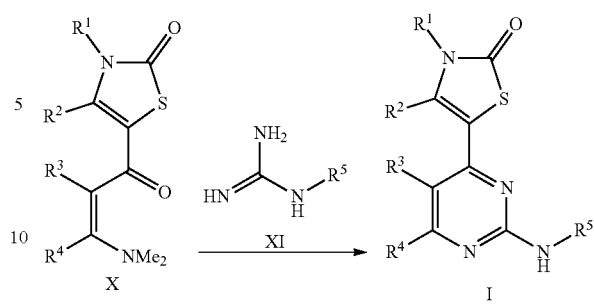

28. A method of treating a CDK-dependent leukemia, said method comprising administering to a subject in need thereof a therapeutically effective amount of a compound according to claim 1.

* * * * *